(12) United States Patent  
Kandimalla et al.

(10) Patent No.: US 8,188,261 B2  
(45) Date of Patent: May 29, 2012

(54) STABILIZED IMMUNE MODULATORY RNA (SIMRA) COMPOUNDS

(75) Inventors: Ekambar Kandimalla, Southboro, MA (US); Tao Lan, Arlington, MA (US); Daqing Wang, Bedford, MA (US); Lakshmi Bhagat, Framingham, MA (US); Sudhir Agrawal, Shrewsbury, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 492 days.

(21) Appl. No.: 12/168,641

(22) Filed: Jul. 7, 2008

(65) Prior Publication Data

US 2009/0053205 A1     Feb. 26, 2009

Related U.S. Application Data

(60) Provisional application No. 60/948,529, filed on Jul. 9, 2007, provisional application No. 60/957,195, filed on Aug. 22, 2007, provisional application No. 60/981,161, filed on Oct. 19, 2007, provisional application No. 61/015,284, filed on Dec. 20, 2007.

(51) Int. Cl.
      *C07H 21/04*          (2006.01)
(52) U.S. Cl. ............... 536/24.5; 536/24.31; 536/24.1; 514/44
(58) Field of Classification Search .................. None
      See application file for complete search history.

(56) References Cited

U.S. PATENT DOCUMENTS

| | | | |
|---|---|---|---|
| 5,912,332 | A | 6/1999 | Agrawal et al. |
| 2001/0044119 | A1 | 11/2001 | Ghadiri et al. |
| 2007/0105801 | A1 | 5/2007 | Agrawal et al. |
| 2007/0142315 | A1 | 6/2007 | Forsbach et al. |
| 2008/0171712 | A1 | 7/2008 | Kandimalla et al. |

FOREIGN PATENT DOCUMENTS

| | | |
|---|---|---|
| WO | WO98/32462 | 7/1998 |
| WO | WO03/086280 | 10/2003 |

OTHER PUBLICATIONS

DE Spaner et al. Oncogene 2008, 27: 208-217.*
Katsargyris et al. Expert Opinion Therapeutic Targets 2008, 12(11): 1329-1346.*
Tokunaga et al.; "Antitumor Activity of Deoxyribonucleic Acid Fraction From *Mycobacterium bovis* BCG. I. Isolation, Physicochemical Characterization, and Antitumor Activity <1,2>"; J. Natl. Cancer Inst. 1984, 72:955-962.
Shimada et al.; "In Vivo Augmentation of Natural Killer Cell Activity with a Deoxyribonucleic Acid Fraction of BCG"; Jpn. H. Cancer Res., 1986, 77:808-816.
Yamamoto et al.; "In Vitro Augmentation of Natural Killer Cell Activity and Production of Interferon—α /βand—γ with Deoxyribonucleic Acid Fraction from *Mycobacterium bovis* BCG"; Jpn. J. Cancer Res., 1988 79:866-873.
Messina et al.; "Stimulation of In Vitro Murine Lymphocyte Proliferation by Bacterial DNA"; J. Immunolo., 1991, 147:1759-1764.
Zhao et al.; "Effect of Difference Chemically Modified Oligodeoxynucleotides on Immune Stimulation"; Biochem. Pharmacol. 1996, 26:173-182.
Hemmi et al.; "A Toll-like receptor recognizes bacterial DNA"; Nature 2000, 408:740-745.
Zhao et al.; "Modulation of Oligonucleotide-Induced Immune Stimulation by Cyclodextrin Analogs"; Biochem Pharmacol. 1996, 52:1537-1544.
Zhao et al.; "Pattern and Kinetics of Cytokine Production Following Administration of Phosphorothioate Oligonucleotides in Mice"; Antisense Nucleic Acid Drug Dev. 1997, 7:495-502.
Zhao et al.; "Site of Chemical Modifications on CpG Containing Phosphorothioate Oligodeoxynucleotide Modulates its Immunostimulatory Activity"; Bioorg. Med. Chem. Lett. 1999, 9:3453-3458.
Zhao et al.; "Immunostimulatory Activity of CpG Containing Phosphorothioate Oligodeoxynucleotide is Modulated by Modi® cation of a Single Deoxynucleoside"; Bioorg. Med. Chem. Lett. 2000, 10:1051-1054.
Yu et al.; "Accessible 50-End of CpG-Containing Phosphorothioate Oligodeoxynucleotides is Essential for Immunostimulatory Activity"; Bioorg. Med. Chem. Lett. 2000, 10:2585-2588.
Yu et al.; "Modulation of Immunostimulatory Activity of CpG Oligonucleotides by Site-Specific Deletion of Nucleobases"; Bioorg. Med. Chem. Lett. 2001, 11:2263-2267.
Kandimalla et al.; "Effect of Chemical Modifications of Cytosine and Guanine in a CpG-Motif of Oligonucleotides: Structure-Immunostimulatory Activity Relationships"; Bioorg. Med. Chem. 2001, 9:807-813.
Kandimalla et al.; "Immunomodulatory Oligonucleotides Containing a Cytosine-Phosphate-2'-deoxy-7-deazaguanosine Motif as Potent Toll-Like Receptor 9 Agonists"; Proc Natl. Acad. Sci. USA, 2005, 102:6925-6930.
Kandimalla et al.; "A dinucleotide motif in oligonucleotides shows potent immunomodulatory activity and overrides species-specific recognition observed with CpG motif"; Proc Natl Acad. Sci USA, 2003, 100:14303-14308.
Cong et al.; "Self-stabilized CpG DNAs optimally activate human B cells and plasmacytoid dendritic cells"; Biochem Biophys Res Commun. 2003, 310:1133-1139.
Kandimalla et al.; "Secondary Structures in CpG Oligonucleotides Affect Immunostimulatory Activity"; Biochem Biophys Res Commun. 2003, 306:948-953.
Kandimalla et al.; "Divergent Synthetic Nucloetide Motif Recognition Pattern: Design and Development of Potent Immunomodulatory Oligodeoxyribonucleotide Agents with Distinct Cytokine Induction Profiles"; Nucleic Acids Res. 2003, 31:2393-2400.
Yu et al.; "Requirement of Nucleobase Proximal to CpG Dinucleotide for Immunostimulatory Activity of Synthetic CpG DNA"; Bioorg. Med. Chem. 2003, 11:459-464.

(Continued)

*Primary Examiner* — Kimberly Chong
(74) *Attorney, Agent, or Firm* — Wood, Phillips, Katz, Clark & Mortimer

(57) ABSTRACT

The invention relates to the therapeutic use of novel stabilized oligoribonucleotides as immune modulatory agents for immune therapy applications. Specifically, the invention provides novel RNA-based oligoribonucleotides with improved nuclease and RNase stability and that have immune modulatory activity through TLR7 and/or TLR8.

5 Claims, 53 Drawing Sheets

OTHER PUBLICATIONS

Bhagat et al.; "CpG Penta- and Hexadeoxyribonucleotides as Potent Immunomodulatory Agents"; Biochem Biophys Res Commun. 2003, 300:853-861.

Yu et al.; "'Immunomers'-Novel 3'-3'-Linked CpG Oligodeoxyribonucleotides as Potent Immunomodulatory Agents"; Nucleic Acids Res. 2002, 30:4460-4469.

Yu et al.; "Design, Synthesis, and Immunostimulatory Properties of CpG DNAs Containing Alkyl-Linker Substitutions: Role of Nucleosides in the Flanking Sequences"; J. Med. Chem. 2002, 45:4540-4548.

Yu et al.; "Potent CpG Oligonucleotides Containing Phosphodiester Linkages: In Vitro and In Vivo Immunostimulatory Properties"; Biochem Biophys Res. Commun. 2002, 297:83-90.

Kandimalla et al.; "Conjugation of Ligand at the 5"—End of CpG DNA Affects Immunostimulatory Activity"; Bioconjug. Chem. 2002, 13:966-974.

Yu et al.; "Immunostimulatory Properties of Phosphorothioate CpG DNA Containing Both 3'-5'-and 2'-5-Internucleotide Linkages"; Nucleic Acids Res. 2002, 30:1613-1619.

Yu et al.; "Immunostimulatory Activity of CpG Oligonucleotides Containing Non-Ionic Methylphosphonate Linkages"; Bioorg. Med. Chem. 2001, 9:2803-2808.

Yu et al.; "Accessible 5'-End of CpG-Containing Phosphorothioate Oligodeoxynucleotides is Essential for Immunostimulatory Activity"; Bioorg. Med. Chem. Lett. 2000, 10:2585-2588.

Putta et al.; "Novel Oligodeoxynucleotide Agonists of TLR9 Containing N3-Me-dC or N1-Me-dG Modifications"; Nucleic Acids Res. 2006, 34:3231-3238.

Diebold et al.; "Innate Antiviral Responses by Means of TLR7-Mediated Recognition of Single-Stranded RNA"; Science, 2004, 303:1529-1531.

Hemmi et al.; "Small Anti-Viral Compounds Activate Immune Cells Via the TLR7 MyD88-Dependent Signaling Pathway"; Nat. Immunol., 2002, 3:196-200.

Jurk et al.; "Human TLR7 or TLR8 Independently Confer Responsiveness to the Antiviral Compound R-848"; Nat. Immunol., 2002, 3:499.

Lee et al.; "Molecular Basis for the Immunostimulatory Activity of Guanine Nucleoside Analogs: Activation of Toll-like receptor 7"; Proc. Natl. Acad. Sci. USA, 2003, 100:6646-6651.

Schon et al.; "The Small Antitumoral Immune Response Modifier Imiquimod Interacts with Adenosine Receptor Signaling in a TLR7- and TLR8-Independent Fashion"; J. Invest Dermatol., 2006, 126:1338-1347.

Heil et al.; "Species-Specific Recognition of Single-Stranded RNA via Toll-like Receptor 7 and 8"; Science, 2004, 303:1524-1529.

Kariko et al.; "Suppression of RNA Recognition by Toll-like Receptors: The Impact of Nucleoside Modification and the Evolutionary Origin of RNA"; Immunity, 2005, 23;165-175.

Ma et al.; "Cationic lipids enhance siRNA-mediated interferon response in mice"; Biochem Biophys Res. Commun., 2005, 330:755-759.

* cited by examiner

Cytokines/chemokines induced by TLR7/8 agonists in human mDC cultures

Before incubation in serum  After incubation in serum

STABILIZED IMMUNE MODULATORY RNA (SIMRA) COMPOUNDS

RELATED APPLICATIONS

This application claims the benefit of U.S. Provisional Application Ser. No. 60/948,529, filed on Jul. 9, 2007; U.S. Provisional Application Ser. No. 60/957,195, filed on Aug. 22, 2007; U.S. Provisional Application Ser. No. 60/981,161, filed on Oct. 19, 2007; and U.S. Provisional Application Ser. No. 61/015,284, filed on Dec. 20, 2007. The contents of these applications are incorporated herein by reference in their entirety.

BACKGROUND OF THE INVENTION

1. Field of the Invention

The invention relates generally to the field of immunology and immunotherapy applications using oligoribonucleotides as immune modulatory agents. More particularly, the invention relates to immune modulatory RNA compositions and methods of use thereof for modulating the immune response through Toll-like receptor 8 (TLR8), Toll-like receptor 7 (TLR7) and TLR8.

2. Summary of the Related Art

The immune response involves both an innate and an adaptive response based upon the subset of cells involved in the response. For example, the T helper (Th) cells involved in classical cell-mediated functions such as delayed-type hypersensitivity and activation of cytotoxic T lymphocytes (CTLs) are Th1 cells, whereas the Th cells involved as helper cells for B-cell activation are Th2 cells. The type of immune response is influenced by the cytokines and chemokines produced in response to antigen exposure. Cytokines provide a means for controlling the immune response by affecting the balance of T helper 1 (Th1) and T helper 2 (Th2) cells, which directly affects the type of immune response that occurs. If the balance is toward higher numbers of Th1 cells, then a cell-mediated immune response occurs, which includes activation of cytotoxic T cells (CTLs). When the balance is toward higher numbers of Th2 cells, then a humoral or antibody immune response occurs. Each of these immune response results in a different set of cytokines being secreted from Th1 and Th2 cells. Differences in the cytokines secreted by Th1 and Th2 cells may be the result of the different biological functions of these two T cell subsets.

Th1 cells are involved in the body's innate response to antigens (e.g. viral infections, intracellular pathogens, and tumor cells). The initial response to an antigen can be the secretion of IL-12 from antigen presenting cells (e.g. activated macrophages and dendritic cells) and the concomitant activation of Th1 cells. The result of activating Th1 cells is a secretion of certain cytokines (e.g. IL-2, IFN-gamma and other cytokines) and a concomitant activation of antigen-specific CTLs. Th2 cells are known to be activated in response to bacteria, parasites, antigens, and allergens and may mediate the body's adaptive immune response (e.g. immunoglobulin production and eosinophil activation) through the secretion of certain cytokines (e.g. IL-3, IL-4, IL-5, IL-6, IL-9, IL-10, IL-13 and other cytokines) and chemokines. Secretion of certain of these cytokines may result in B-cell proliferation and an increase in antibody production. In addition, certain of these cytokines may stimulate or inhibit the release of other cytokines (e.g IL-10 inhibits IFN-γ secretion from Th1 cells and IL-12 from dendritic cells). Ultimately, the balance between Th1 and Th2 cells and the cytokines and chemokines released in response to selected stimulus can have an important role in how the body's immune system responds to disease. For example, IFN-α may inhibit hepatitis C, and MIP-1α and MIP-1 (also known as CCL3 and CCL4 respectively) may inhibit HIV-1 infection. Optimal balancing of the Th1/Th2 immune response presents the opportunity to use the immune system to treat and prevent a variety of diseases.

The Th1 immune response can be induced in mammals for example by introduction of bacterial or synthetic DNA containing unmethylated CpG dinucleotides, which immune response results from presentation of specific oligonucleotide sequences (e.g. unmethylated CpG) to receptors on certain immune cells known as pattern recognition receptors (PRRs). Certain of these PRRs are Toll-like receptors (TLRs).

TLRs are intimately involved in inducing the innate immune response in response to microbial infection. In vertebrates, TLRs consist of a family of ten proteins (TLR1 to TLR10) that are known to recognize pathogen associated molecular patterns. Of the ten, TLR3, 7, 8, and 9 are known to localize in endosomes inside the cell and recognize nucleic acids (DNA and RNA) and small molecules such as nucleosides and nucleic acid metabolites. TLR3 and TLR9 are known to recognize nucleic acid such as dsRNA and unmethylated CpG dinucleotide present in viral and bacterial and synthetic DNA, respectively. Bacterial DNA has been shown to activate the immune system and to generate antitumor activity (Tokunaga T et al., J. Natl. Cancer Inst. (1984) 72:955-962; Shimada S, et al., Jpn. H cancer Res, 1986, 77, 808-816; Yamamoto S, et al., Jpn. J. Cancer Res., 1986, 79, 866-73; Messina, J, et al., J. Immunolo. (1991) 147:1759-1764). Other studies using antisense oligonucleotides containing CpG dinucleotides have shown stimulation of an immune response (Zhao Q, et al., Biochem. Pharmacol. 1996, 26, 173-82). Subsequent studies showed that TLR9 recognizes unmethylated CpG motifs present in bacterial and synthetic DNA (Hemmi H, et al., Nature. (2000) 408:740-5). Other modifications of CpG-containing phosphorothioate oligonucleotides can also affect their ability to act through TLR9 and modulate the immune response (see, e.g., Zhao et al., Biochem. Pharmacol. (1996) 51:173-182; Zhao et al., Biochem Pharmacol. (1996) 52:1537-1544; Zhao et al., Antisense Nucleic Acid Drug Dev. (1997) 7:495-502; Zhao et al., Bioorg. Med. Chem. Lett. (1999) 9:3453-3458; Zhao et al., Bioorg. Med. Chem. Lett. (2000) 10:1051-1054; Yu et al., Bioorg. Med. Chem. Lett. (2000) 10:2585-2588; Yu et al., Bioorg. Med. Chem. Lett. (2001) 11:2263-2267; and Kandimalla et al., Bioorg. Med. Chem. (2001) 9:807-813). In addition, structure activity relationship studies have allowed identification of synthetic motifs and novel DNA-based structures that induce specific immune response profiles that are distinct from those resulting from unmethylated CpG dinucleotides. (Kandimalla E R, et al., Proc Natl Acad Sci USA. (2005) 102:6925-30. Kandimalla E R, et al., Proc Natl Acad Sci USA. (2003) 100:14303-8. Cong Y P, et al., Biochem Biophys Res Commun. (2003) 310:1133-9. Kandimalla E R, et al., Biochem Biophys Res Commun. (2003) 306:948-53. Kandimalla E R, et al., Nucleic Acids Res. (2003) 31:2393-400. Yu D, et al., Bioorg Med Chem. (2003) 11:459-64. Bhagat L, et al., Biochem Biophys Res Commun. (2003) 300:853-61. Yu D, et al., Nucleic Acids Res. (2002) 30:4460-9. Yu D, et al., J Med Chem. (2002) 45:4540-8. Yu D, et al., Biochem Biophys Res Commun. (2002) 297:83-90. Kandimalla E R, et al., Bioconjug Chem. (2002) 13:966-74. Yu D, K et al., Nucleic Acids Res. (2002) 30:1613-9. Yu D, et al., Bioorg Med. Chem. (2001) 9:2803-8. Yu D, et al., Bioorg Med Chem Lett. (2001) 11:2263-7. Kandimalla E R, et al., Bioorg Med Chem. (2001) 9:807-13. Yu D, et al., Bioorg Med Chem Lett. (2000) 10:2585-8, Putta M R, et al., Nucleic Acids Res. (2006) 34:3231-8). However, until recently, natural ligands for TLR7 and TLR8 were unknown.

It has been shown that TLRs 7 and 8 recognize viral and synthetic single-stranded RNAs and small molecules, including a number of nucleosides (Diebold, S. S., et al., Science v: 303, 1529-1531 (2004). Diebold et al. (Science, 303:1529-1531 (2004)) show that the IFN-α response to influenza virus requires endosomal recognition of influenza genomic RNA and signaling by means of TLR7 and MyD88 and identify ssRNA as a ligand for TLR7. Certain synthetic compounds, the imidazoquinolones, imiquimod (R-837) and resiquimod (R-848) are ligands of TLR7 and TLR8 (Hemmi H et al., (2002) Nat Immunol 3:196-200; Jurk M et al., (2002) Nat Immunol 3:499). In addition, certain guanosine analogs, such as 7-deaza-G, 7-thia-8-oxo-G (TOG), and 7-allyl-8-oxo-G (loxoribine), have been shown to activate TLR7 at high concentrations (Lee J et al., Proc Natl Acad Sci USA. 2003, 100:6646-51). However, these small molecules, eg. imiquimod, are also known to act through other receptors (Schon M P, et al., (2006) J. Invest Dermatol., 126, 1338-47)

The lack of any known specific ssRNA motif for TLR7 or TLR8 recognition and the potentially wide range of stimulatory ssRNA molecules suggest that TLR7 and TLR8 can recognize both self and viral RNA. Recently it was shown that certain GU-rich oligoribonucleotides are immunostimulatory and act through TLR7 and TLR8 (Heil et al. Science, 303: 1526-1529 (2004); Lipford et al. WO03/086280; Wagner et al. WO98/32462) when complexed with N-[1-(2,3-Dioleoyloxy)propyl]-N,N,N trimethylammoniummethylsulfate (DOTAP) or other lipid agents. However, RNA molecules have been used for many years, for example as ribozymes and, more recently, siRNA and microRNA, and RNA employed as ribozymes, siRNA, and microRNA contain GU dinucleotides. In addition, a number these RNA molecules have been shown to elicit immune responses through TLR stimulation in the presence of lipids (Kariko et al., Immunity (2005) 23:165-75; Ma Z et al., Biochem Biophys Res Commun., (2005) 330, 755-9). However, the instability of these RNA molecules has hindered progress in using and applying these molecules in many areas (e.g. prevention and treatment of human disease).

Oligonucleotides and oligodeoxynucleotides containing a ribose or deoxyribose sugar have been used in a wide variety of fields, including but not limited to diagnostic probing, PCR priming, antisense inhibition of gene expression, siRNA, microRNA, aptamers, ribozymes, and immunotherapeutic agents based on Toll-like Receptors (TLRs). More recently, many publications have demonstrated the use of oligodeoxynucleotides as immune modulatory agents and their use alone or as adjuvants in immunotherapy applications for many diseases, such as allergy, asthma, autoimmunity, cancer and infectious disease.

The fact that DNA oligonucleotides are recognized by TLR9, while RNA oligonucleotides are recognized by TLR7 and/or TLR8 is most likely due to differences in the structural conformations between DNA and RNA. However, the chemical differences between DNA and RNA also make DNA far more chemically and enzymatically stable than RNA.

RNA is rapidly degraded by ubiquitous extracellular ribonucleases (RNases) which ensure that little, if any, self-ssRNA reaches the antigen-presenting cells. Exonuclease degradation of nucleic acids is predominantly of 3'-nuclease digestion with a smaller percentage through 5'-exonuclease action. In addition to exonuclease digestion, RNA can also be degraded by endonuclease activity of RNAses. RNA-based molecules have so far had to be complexed with lipids to provide stability against nucleases.

While providing an essential function of preventing autoimmune reactivity, these ribonucleases also present a substantial problem for any synthetic ssRNA molecule designed to be exploited for immunotherapy, as ribonucleases will rapidly degrade both synthetic and natural ssRNA. To overcome this hurdle, protection of ssRNA molecules from degradation has been attempted by encapsulating the ssRNA in lipsomes, condensing it with polyethylenimine, or complexing it to molecules such as N-[1-(2,3 dioleoyloxy)-propyl]-N,N,N-trimethylammonium methyl-sulfate (DOTAP). However, these protective measures are secondary measures applied to a still unstable ssRNA, and the effects of these protective measures on the in vivo efficacy and immune modulatory activity of ssRNA (natural or synthetic) remain unclear.

Agrawal et al. (Ser. No. 11/697,422) describe a novel class of SIMRA compositions. However, a challenge remains to develop additional compounds that retain the naked RNA such that it continues to be recognized as a ligand for TLR7 and/or TLR8, while improving its stability such that it can be made to be a useful in vivo molecule. Ideally, this challenge might be met through the design of inherently stable RNA-based molecules that can act as new immunotherapic agents, which will find use in a number of clinically relevant applications, such as improving the effects of vaccination when co-administered or treating and/or preventing diseases when invoking or enhancing an immune response is beneficial, for example cancer, autoimmune disorders, airway inflammation, inflammatory disorders, infectious diseases, skin disorders, allergy, asthma or diseases caused by pathogens.

BRIEF SUMMARY OF THE INVENTION

In a first aspect, the invention provides novel stabilized immune modulatory RNA ("SIMRA") compounds, further defined below, and their use for inducing and/or enhancing an immune response. The novel chemical entities according to the invention provide immune response inducing and/or enhancing compounds that are substantially more effective at inducing an immune response and substantially less susceptible to degradation. The methods according to the invention enable using SIMRA to modify the cytokine and/or chemokine profile for immunotherapy applications.

In one embodiment of the first aspect, the invention provides a SIMRA compound as an agonist for TLR8.

In another embodiment of the first aspect, the invention provides a SIMRA compound as an agonist for TLR7 and TLR8.

In a further embodiment of the first aspect, the invention provides a SIMRA compound as an agonist for TLR7.

In a further embodiment of the first aspect, the invention provides a SIMRA compound as an adjuvant.

In a second aspect, the invention provides pharmaceutical compositions. These compositions comprise any one of the SIMRA compositions of the invention and a physiologically acceptable or pharmaceutically acceptable carrier.

In a third aspect, the invention provides a method for generating an immune response in a vertebrate, the method comprising administering to the vertebrate at least one of the SIMRA compounds according to the invention in a pharmaceutically effective amount.

In a fourth aspect, the invention provides a method for therapeutically treating a vertebrate having a disease or disorder where inducing and/or enhancing an immune response would be beneficial, for example cancer, autoimmune disorders, airway inflammation, inflammatory disorders, infectious diseases, skin disorders, allergy, asthma or diseases caused by pathogens, such method comprising administering to the patient having such a disorder or disease at least one of the SIMRA compounds according to the invention in a pharmaceutically effective amount.

In a fifth aspect, the invention provides a method for preventing a disease or disorder in a vertebrate where inducing and/or enhancing an immune response would be beneficial, for example cancer, an autoimmune disorder, airway inflammation, inflammatory disorders, infectious disease, skin disorders, allergy, asthma or diseases caused by a pathogen, such method comprising administering to a vertebrate that is susceptible to such a disorder or disease at least one of the SIMRA compounds according to the invention in a pharmaceutically effective amount.

In a sixth aspect, the invention provides a method of isolating cells capable of producing cytokine or chemokines (e.g. immune cells, PBMCs), culturing such cells under standard cell culture conditions, ex vivo treating such cells with at least one of the SIMRA compounds of the invention such that the isolated cells produce or secrete increased levels of cytokines or chemokines, and administering or re-administering the treated cells to a patient in need of cytokine or chemokine therapy for the prevention or treatment of disease.

In a further embodiment of this aspect of the invention, the patient in need of cytokine or chemokine therapy for prevention or treatment of disease is administered the isolated, SIMRA-treated cells in combination with one or more SIMRA compounds.

BRIEF DESCRIPTION OF THE DRAWINGS

SIMRA compounds of the invention were synthesized according to Example 1.

FIGS. 4D-4AA depict cytokine and chemokine concentrations from human PBMCs that were treated and analyzed according to example 3. Briefly, the PBMCs were isolated from freshly obtained healthy human volunteer's blood and cultured with increasing concentrations of TLR7/8 agonists for 24 hr, and supernatants were collected and analyzed by Luminex multiplex assay cytokine and chemokine levels. The data demonstrate that administration of a SIMRA according to the invention generates a distinct, dose-dependent, TLR-mediated cytokine and chemokine profile.

DETAILED DESCRIPTION OF THE PREFERRED EMBODIMENTS

Figure 1:
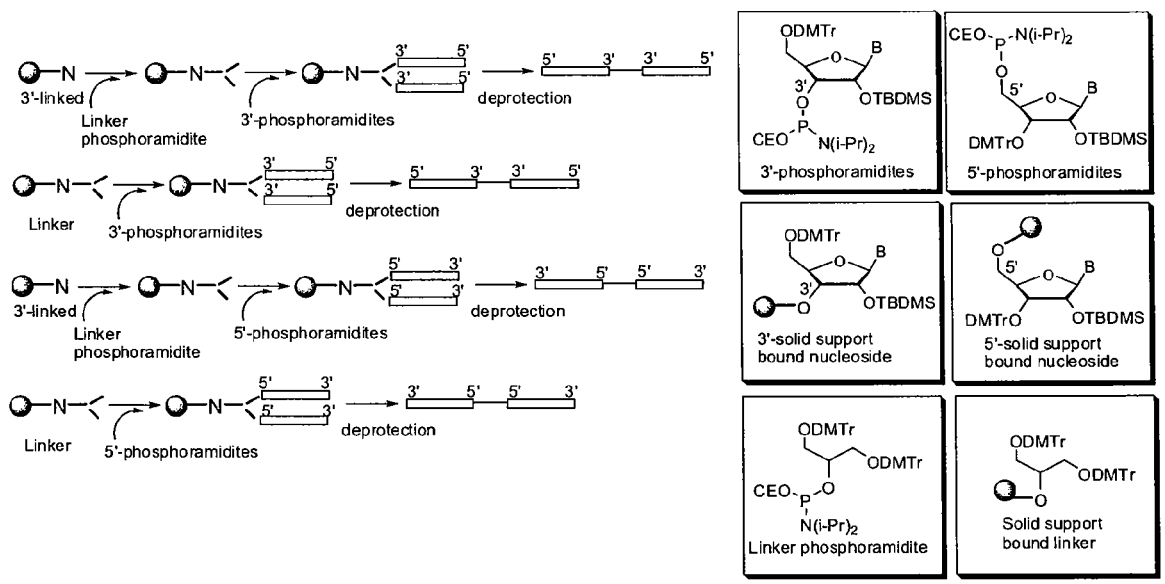
FIG. 1 is a synthetic scheme for the parallel synthesis of SIMRA compounds of the invention. DMTr=4,4'-dimethoxytrityl; CE=cyanoethyl.
Figure 2A:
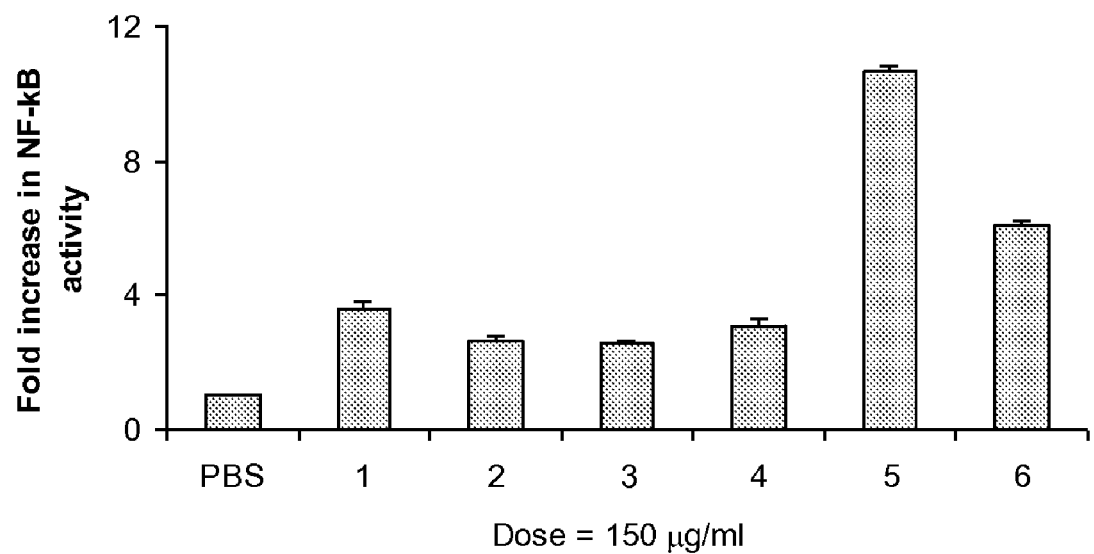
FIG. 2A depicts NF-κB activity in HEK293 cells expressing human TLR8 that were treated and analyzed according to example 2. Briefly, the HEK293 cells were stimulated with 150 μg/ml of agonists of TLR8 for 18 hr, and the levels of NF-κB were determined using SEAP (secreted form of human embryonic alkaline phosphatase) assay. The data demonstrate that administration of a SIMRA according to the invention generates a distinct TLR-mediated immune response profile.
Figure 2B:
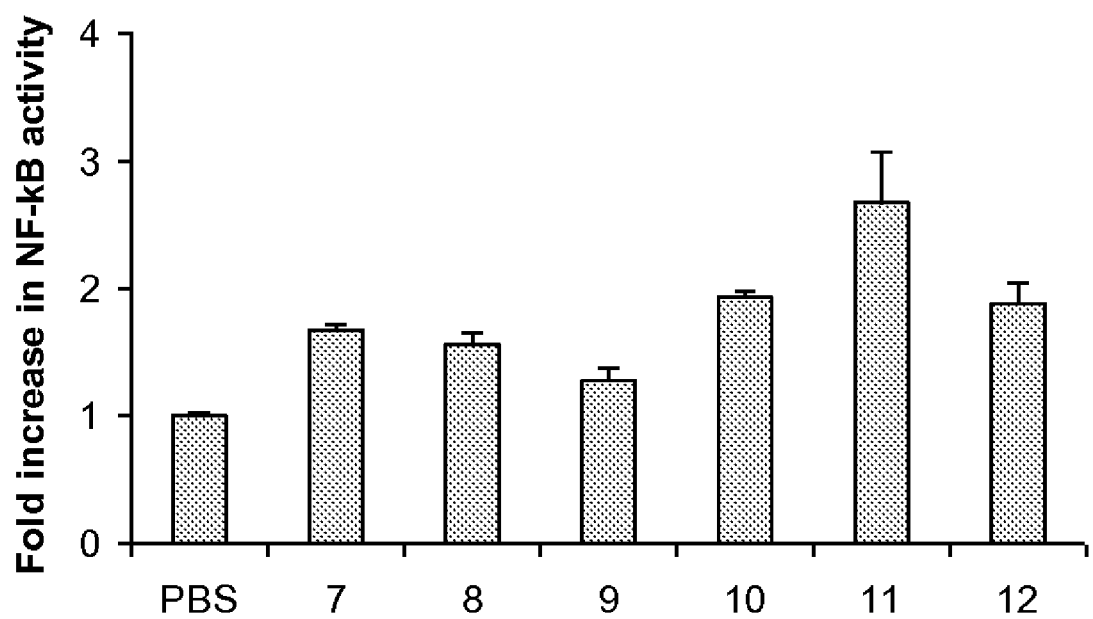
FIG. 2B depicts NF-κB activity in HEK293 cells expressing human TLR8 that were treated and analyzed according to example 2. Briefly, the HEK293 cells were stimulated with 150 μg/ml of agonists of TLR8 for 20 hr and the levels of NF-κB were determined using SEAP assay. The data demonstrate that administration of a SIMRA according to the invention generates a distinct TLR-mediated immune response profile.
Figure 2C:
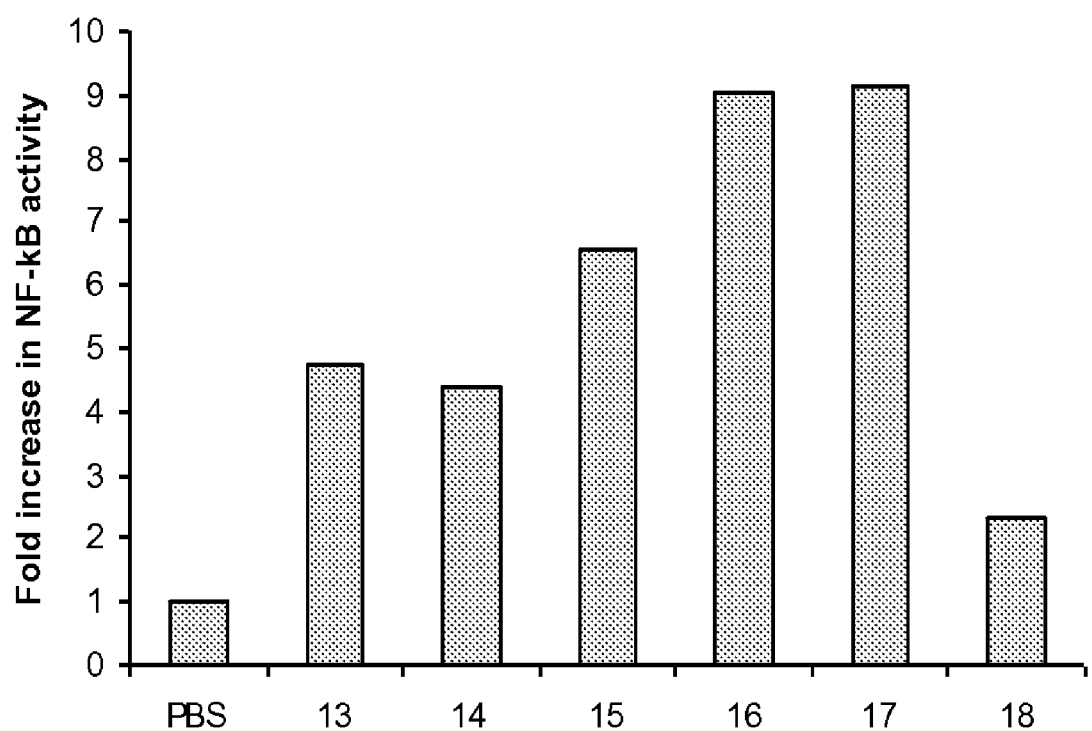
FIG. 2C-2E depict NF-κB activity in HEK293 cells expressing human TLR8 that were treated and analyzed according to example 2. Briefly, the HEK293 cells were stimulated with 150 μg/ml of agonists of TLR8 for 18 hr, and the levels of NF-κB were determined using SEAP assay. The data demonstrate that administration of a SIMRA according to the invention generates a distinct TLR-mediated immune response profile.
Figure 2D:
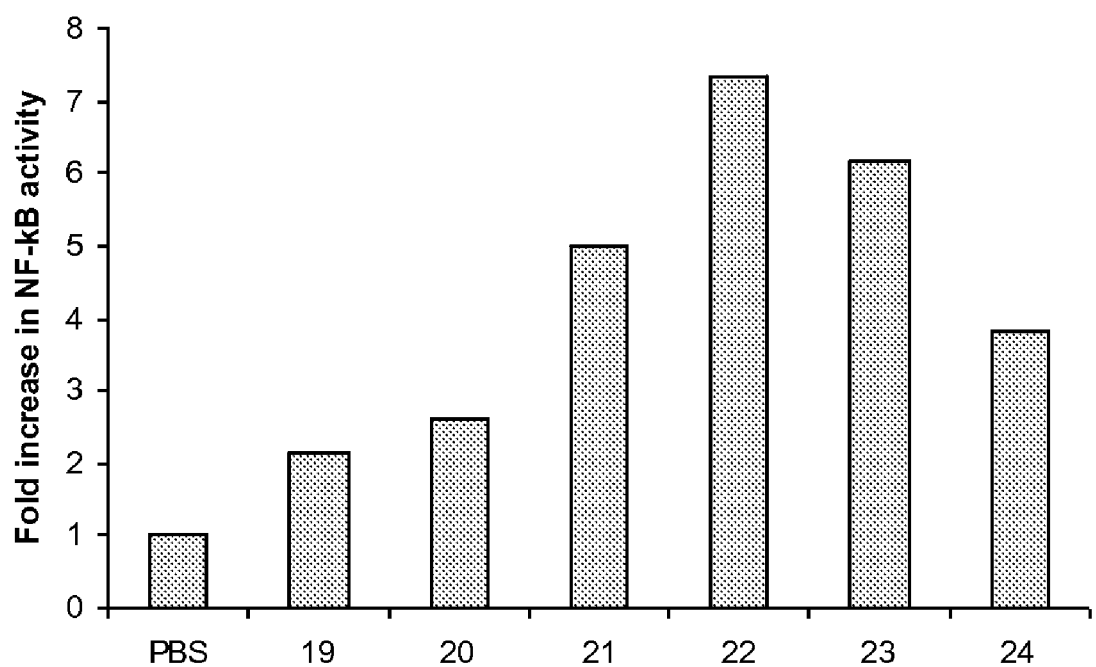
Figure 2E:
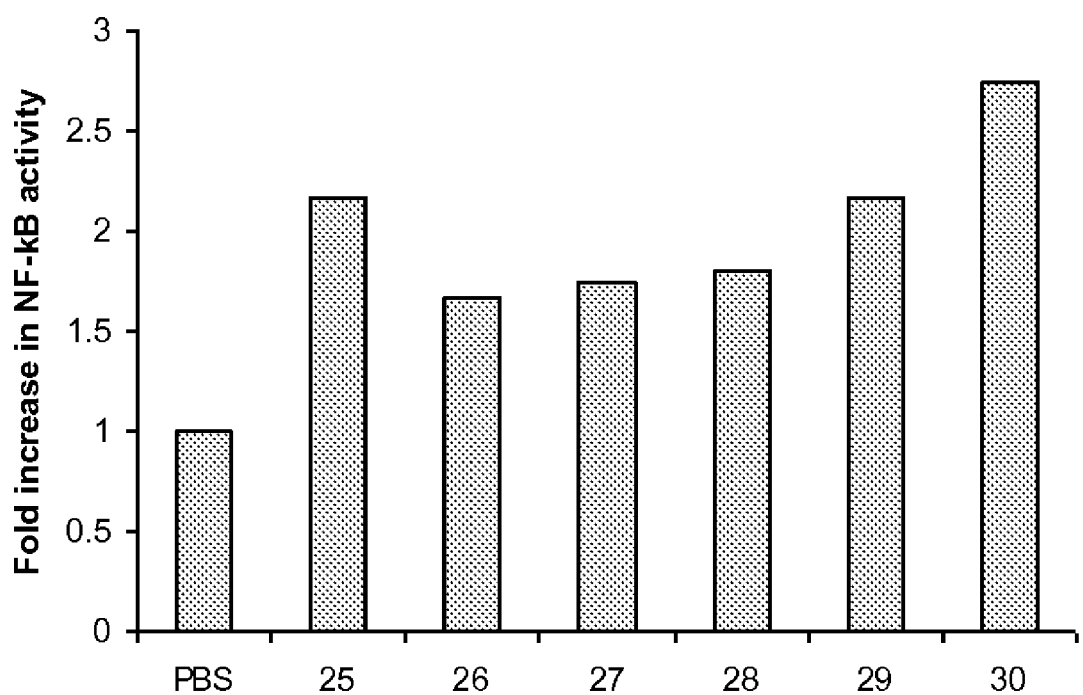
Figure 2F:
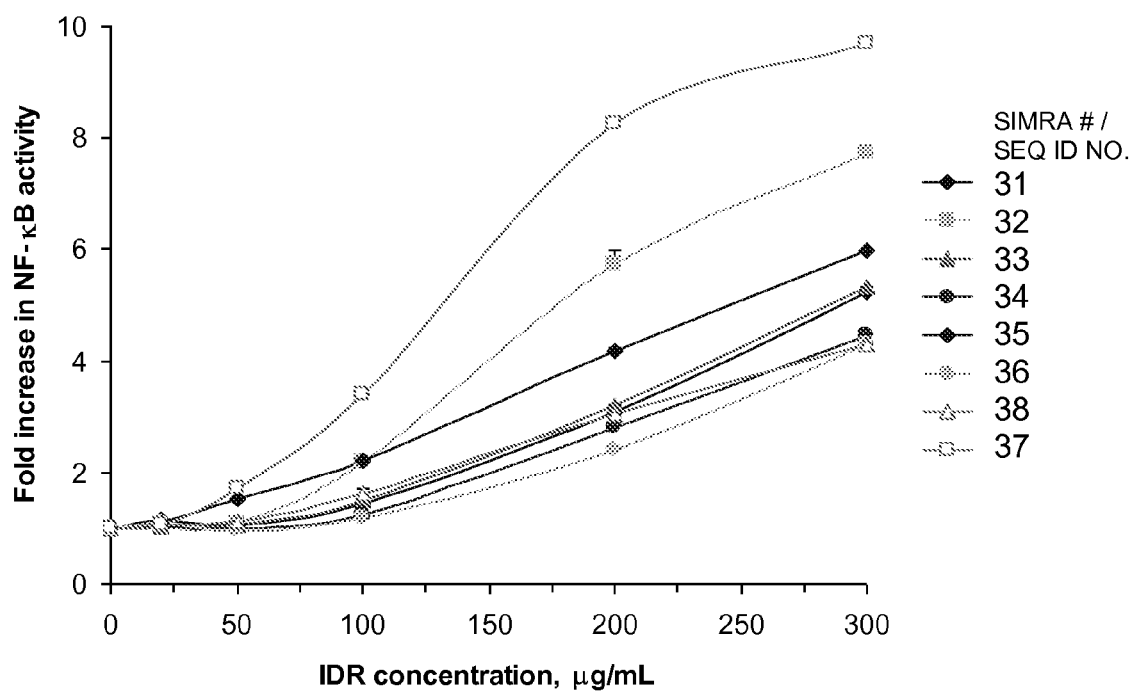
FIG. 2F depicts NF-κB activity in HEK293 cells expressing human TLR8 that were treated and analyzed according to example 2. Briefly, HEK293 cells expressing human TLR8 were stimulated with 0, 20, 50, 100, 200, or 300 μg/ml of agonists for 18 hr. The levels of NF-κB were determined using SEAP assay. The data demonstrate that administration of a SIMRA according to the invention generates a distinct TLR-mediated immune response profile.
Figure 2G:
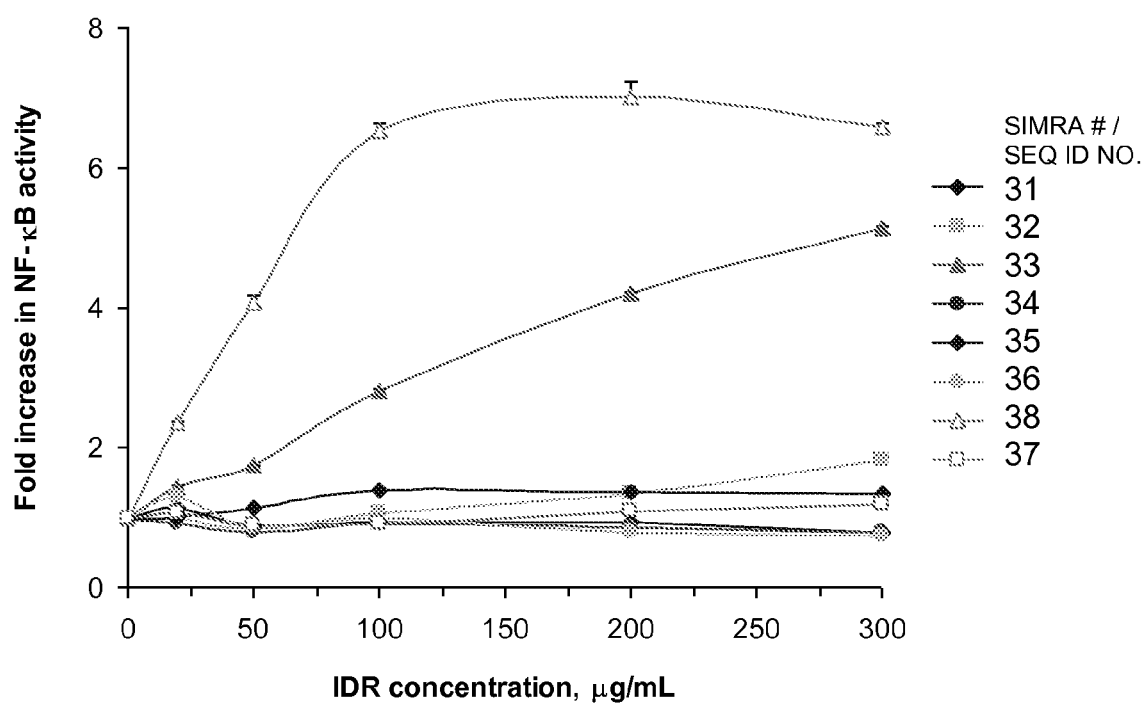
FIG. 2G depicts NF-κB activity in HEK293 cells expressing human TLR7 that were treated and analyzed according to example 2. Briefly, HEK293 cells expressing human TLR7 were stimulated with 0, 20, 50, 100, 200, or 300 μg/ml of agonists for 18 hr. The levels of NF-κB were determined using SEAP assay. The data demonstrate that administration of a SIMRA according to the invention generates a distinct TLR-mediated immune response profile.
Figure 2H:
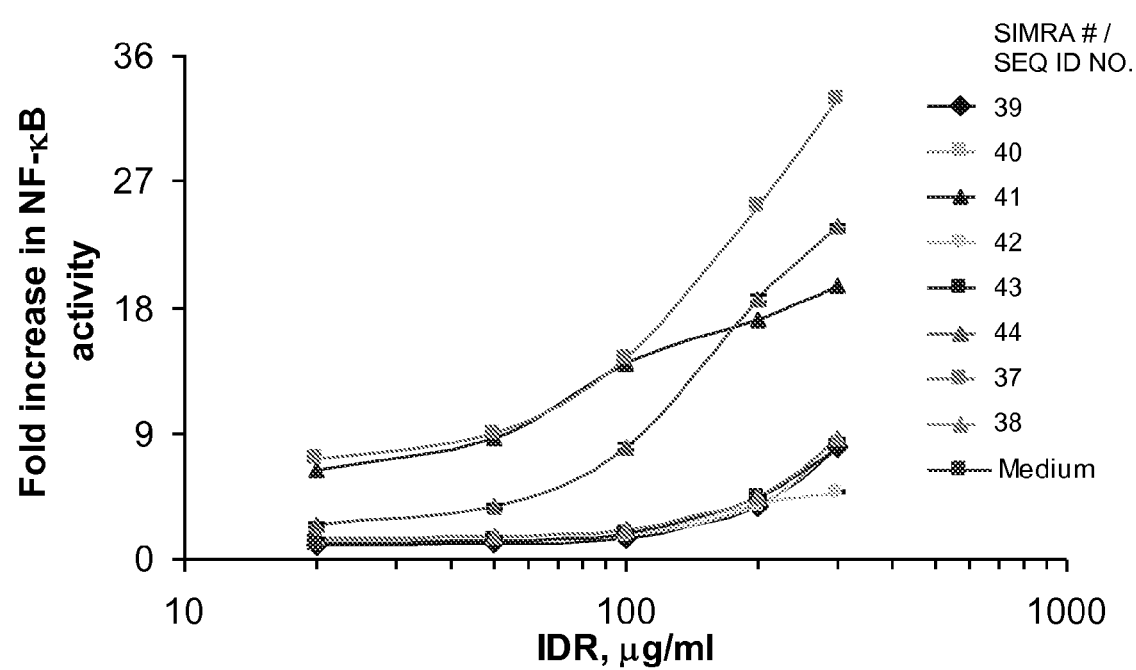
FIGS. 2H, 2J and 2L depict NF-κB activity in HEK293 cells expressing human TLR8 that were treated and analyzed according to example 2. Briefly, HEK293 cells expressing human TLR8 were stimulated with 0, 20, 50, 100, 200, or 300 μg/ml of agonists for 18 hr. The levels of NF-κB were determined using SEAP assay. The data demonstrate that administration of a SIMRA according to the invention generates a distinct TLR-mediated immune response profile.
Figure 2I:
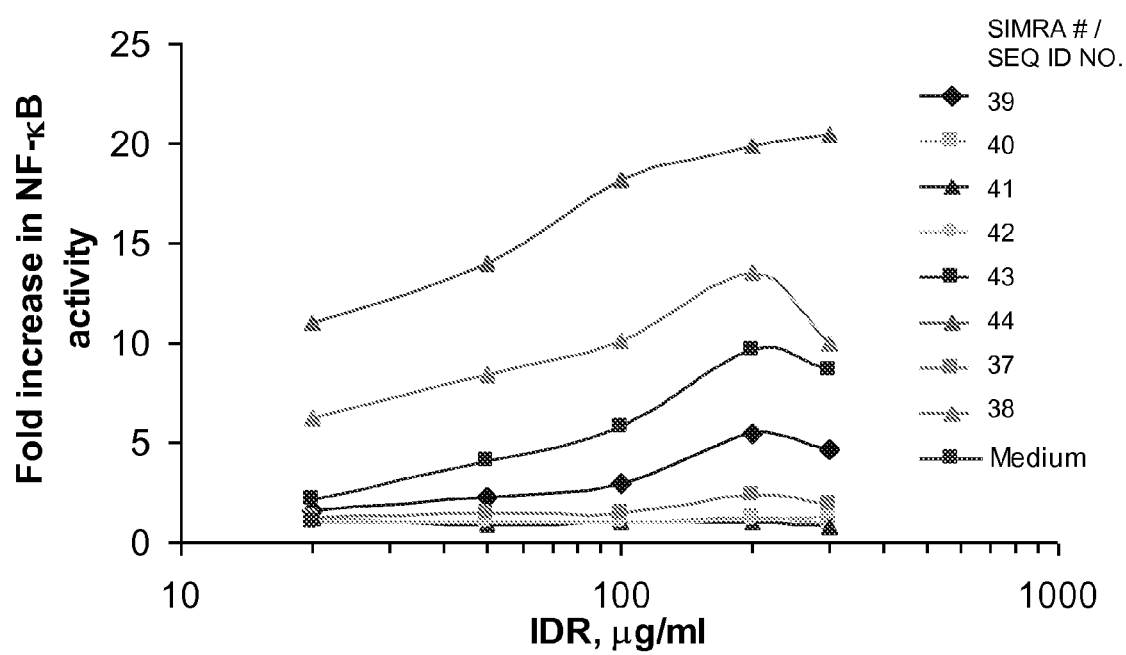
FIGS. 2I, 2K and 2M depict NF-κB activity in HEK293 cells expressing human TLR7 that were treated and analyzed according to example 2. Briefly, HEK293 cells expressing human TLR7 were stimulated with 0, 20, 50, 100, 200, or 300 μg/ml of agonists for 18 hr. The levels of NF-κB were determined using SEAP assay. The data demonstrate that administration of a SIMRA according to the invention generates a distinct TLR-mediated immune response.
Figure 2J:
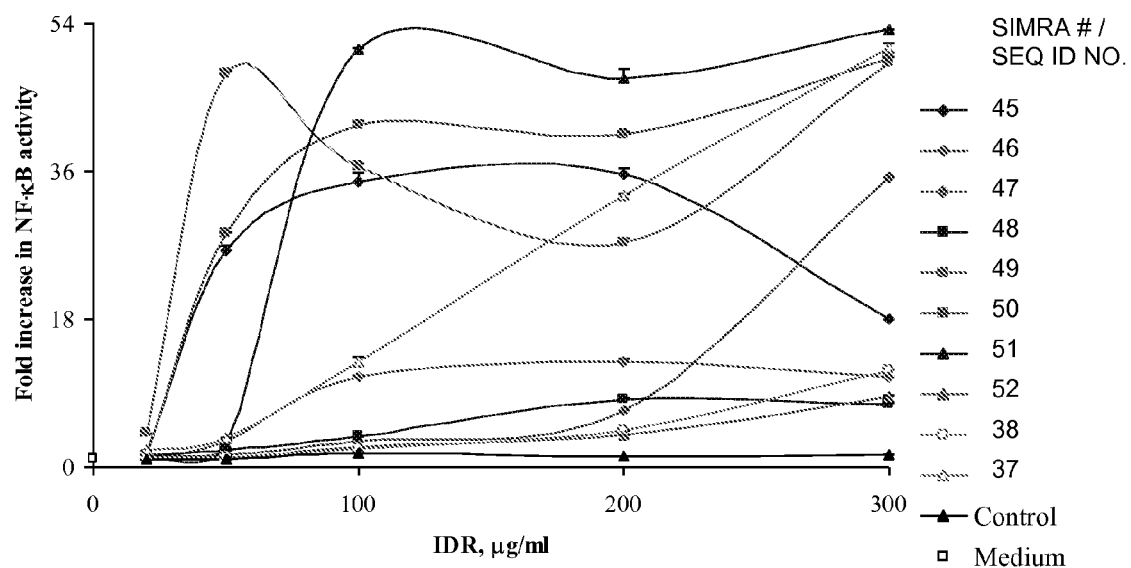
Figure 2K:
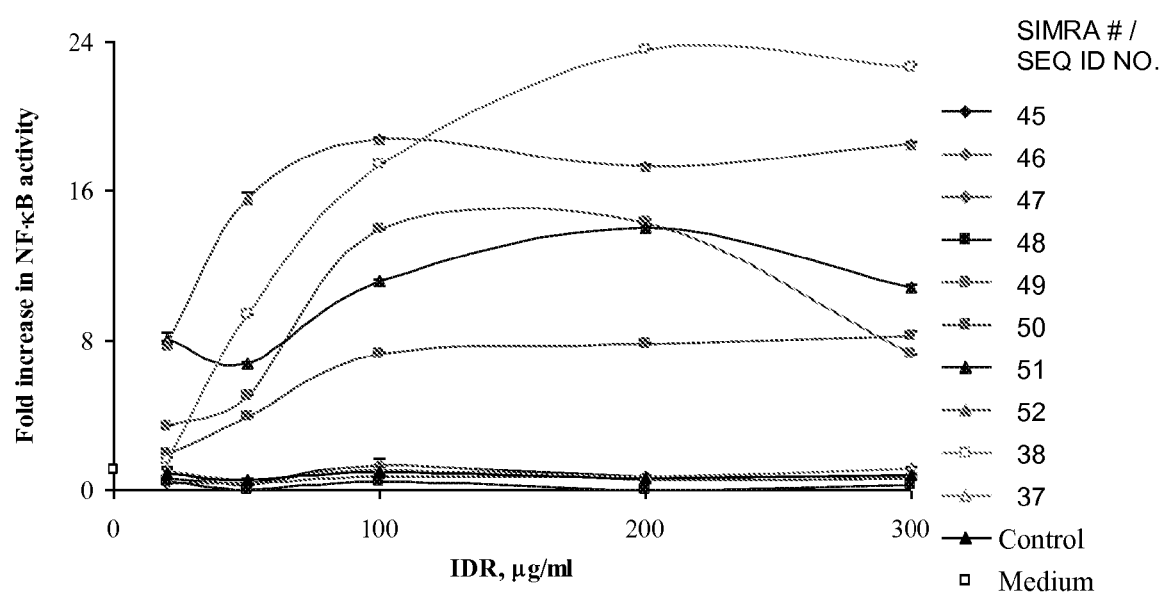
Figure 2L:
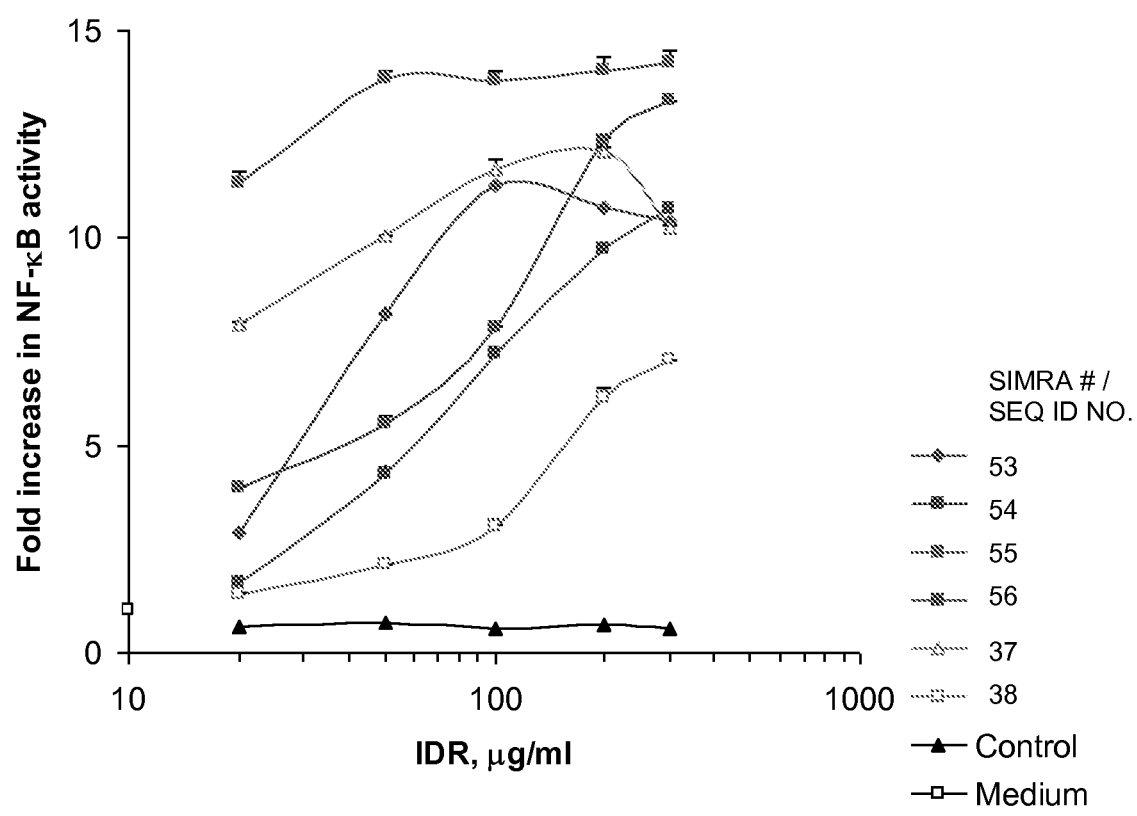
Figure 2M:
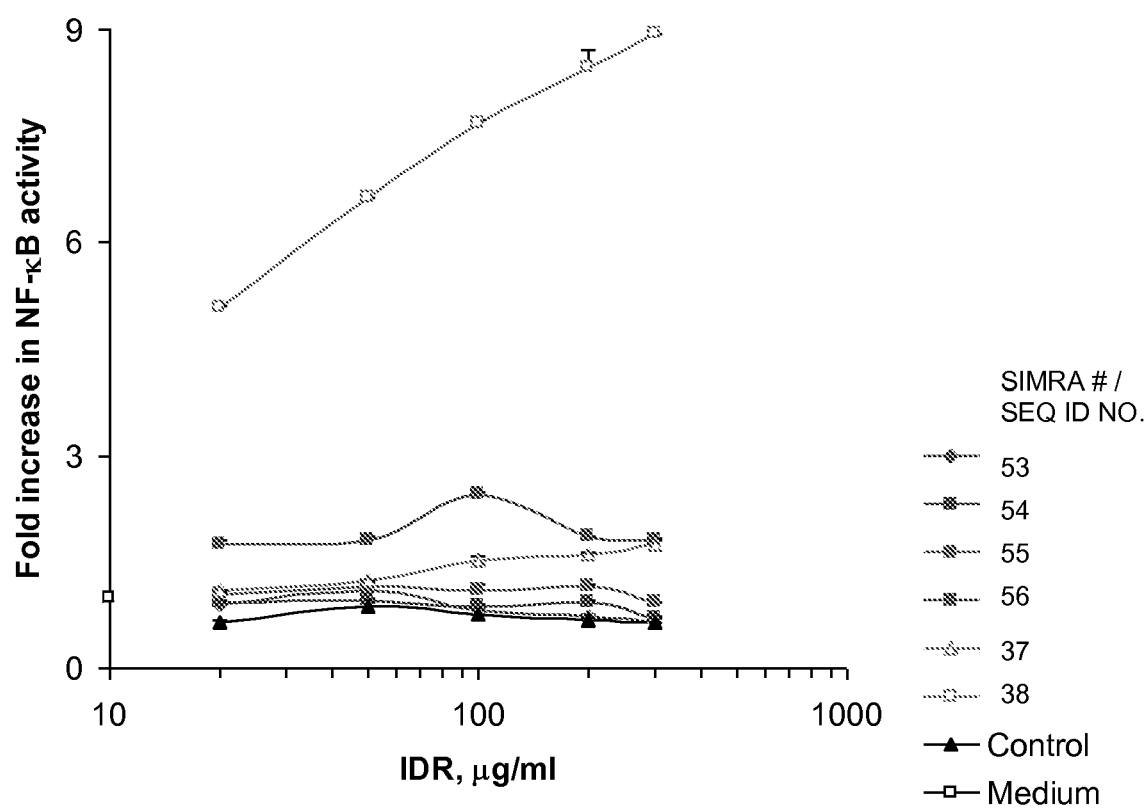
Figure 3A:
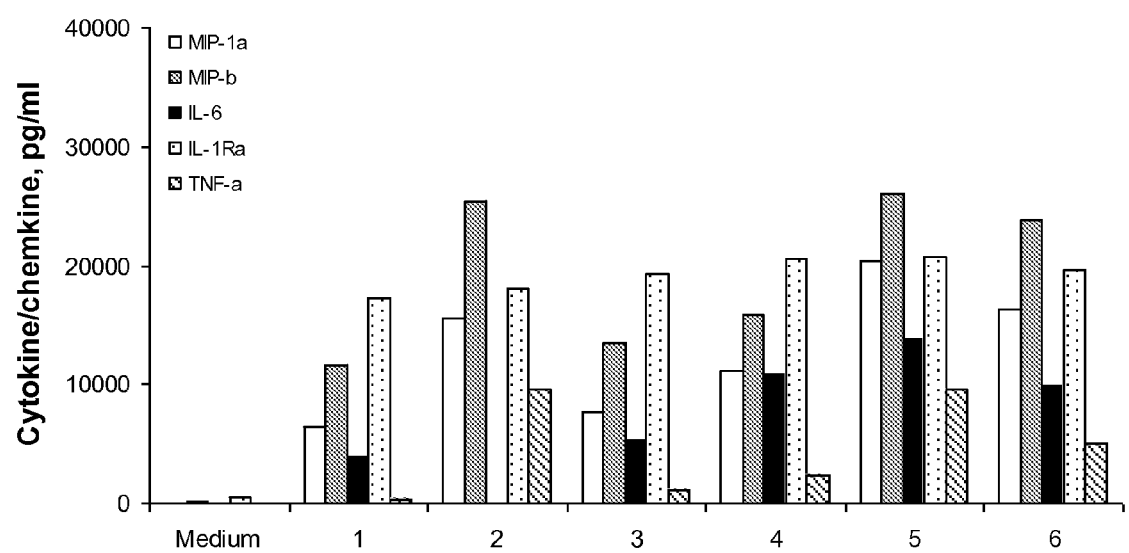
FIGS. 3A-3C depict cytokine and chemokine concentrations from human PBMCs that were treated and analyzed according to example 3. Briefly, the PBMCs were isolated from freshly obtained healthy human volunteer's blood and cultured with 50 μg/ml dose of TLR7/8 agonists for 24 hr, and supernatants were collected and analyzed by Luminex multiplex assay cytokine and chemokine levels. The data demonstrate that administration of a SIMRA according to the invention generates a distinct TLR-mediated cytokine and chemokine profile.
Figure 3B:
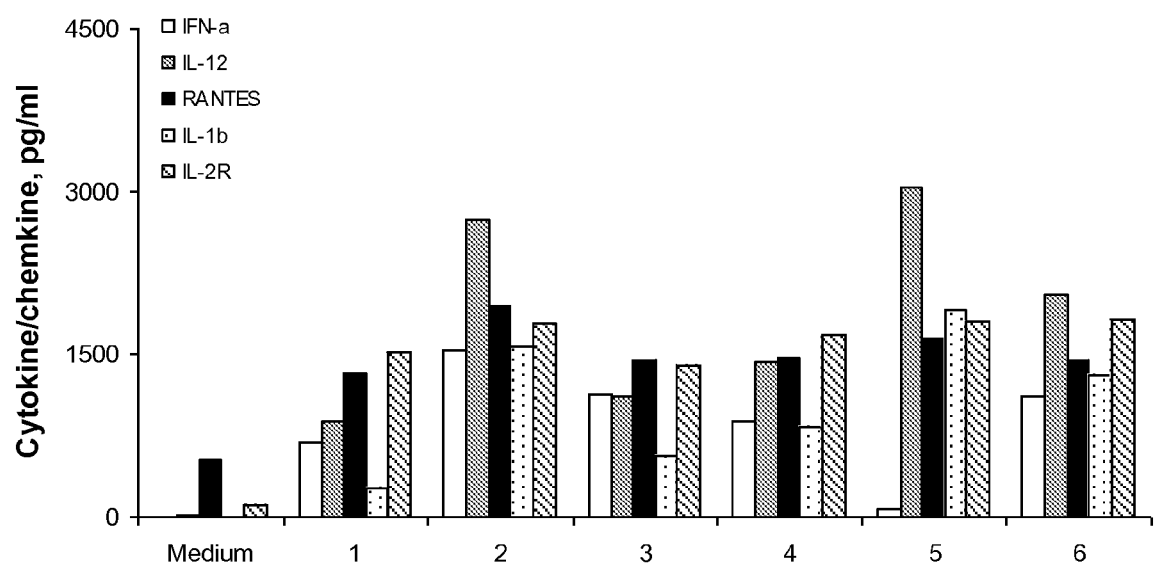
Figure 3C:
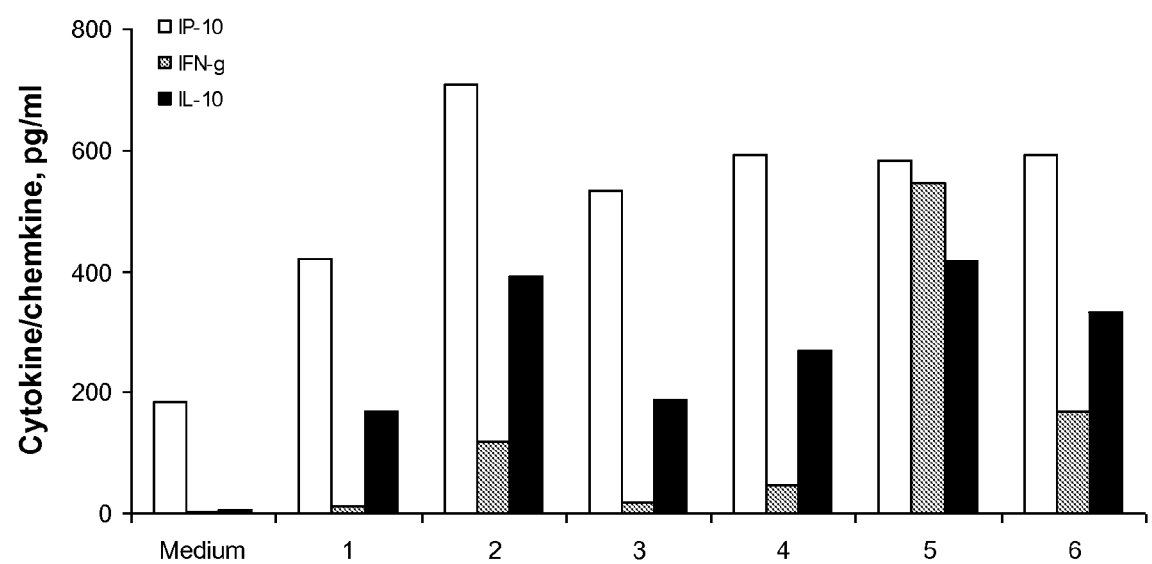
Figure 4A:
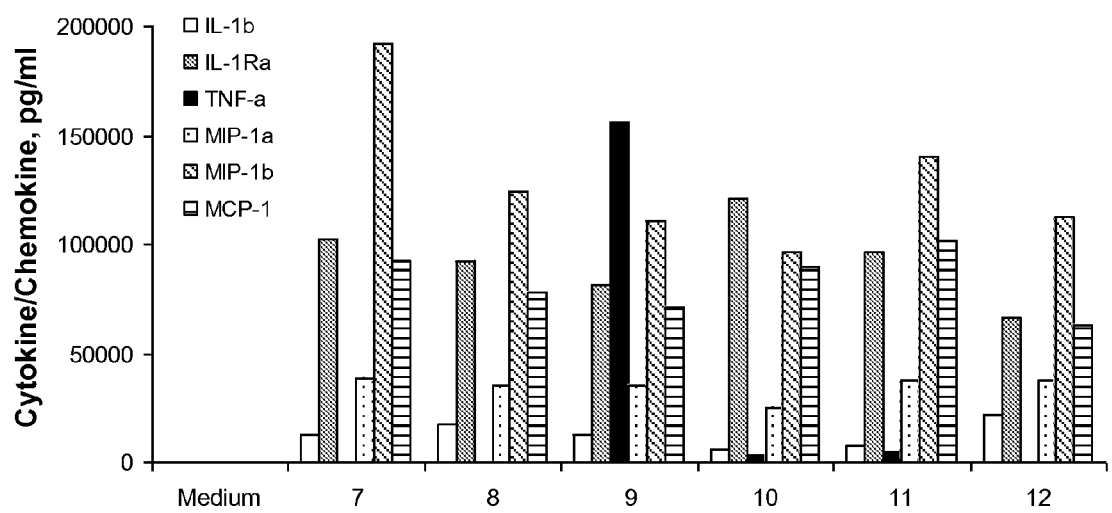
FIGS. 4A-4C depict cytokine and chemokine concentrations from human PBMCs that were treated and analyzed according to example 3. Briefly, the PBMCs were isolated from freshly obtained healthy human volunteer's blood and cultured with 200 μg/ml dose of TLR7/8 agonists for 24 hr, and supernatants were collected and analyzed by Luminex multiplex assay cytokine and chemokine levels. The data demonstrate that administration of a SIMRA according to the invention generates a distinct TLR-mediated cytokine and chemokine profile.
Figure 4B:
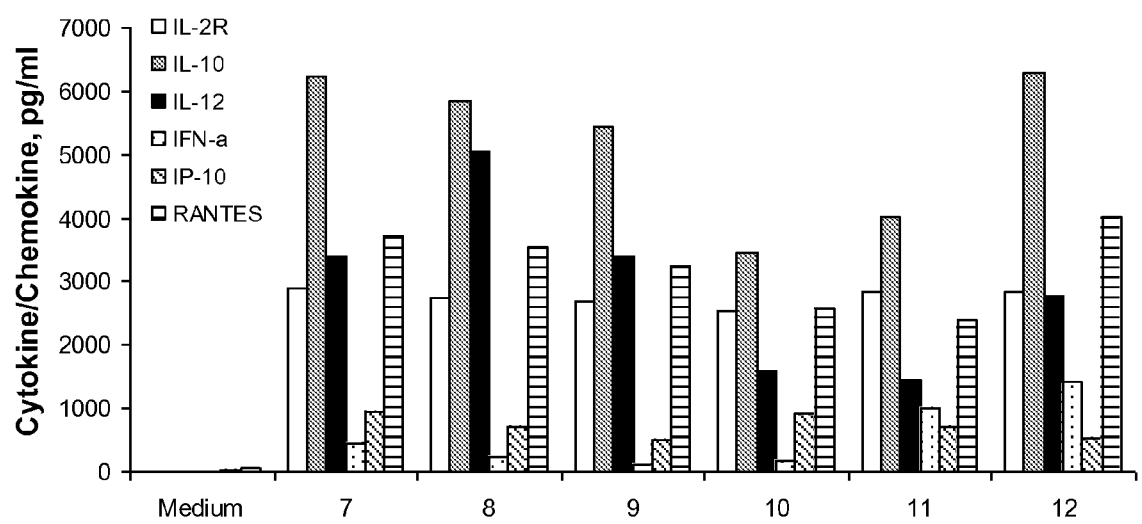
Figure 4C:
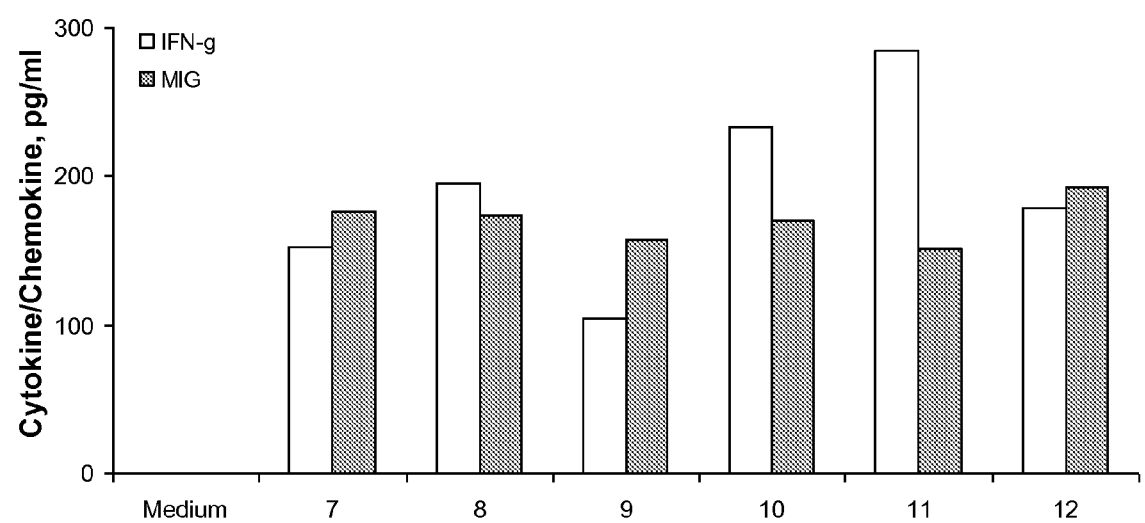
Figures 4D, 4E, 4F, 4G, 4H, 4I:
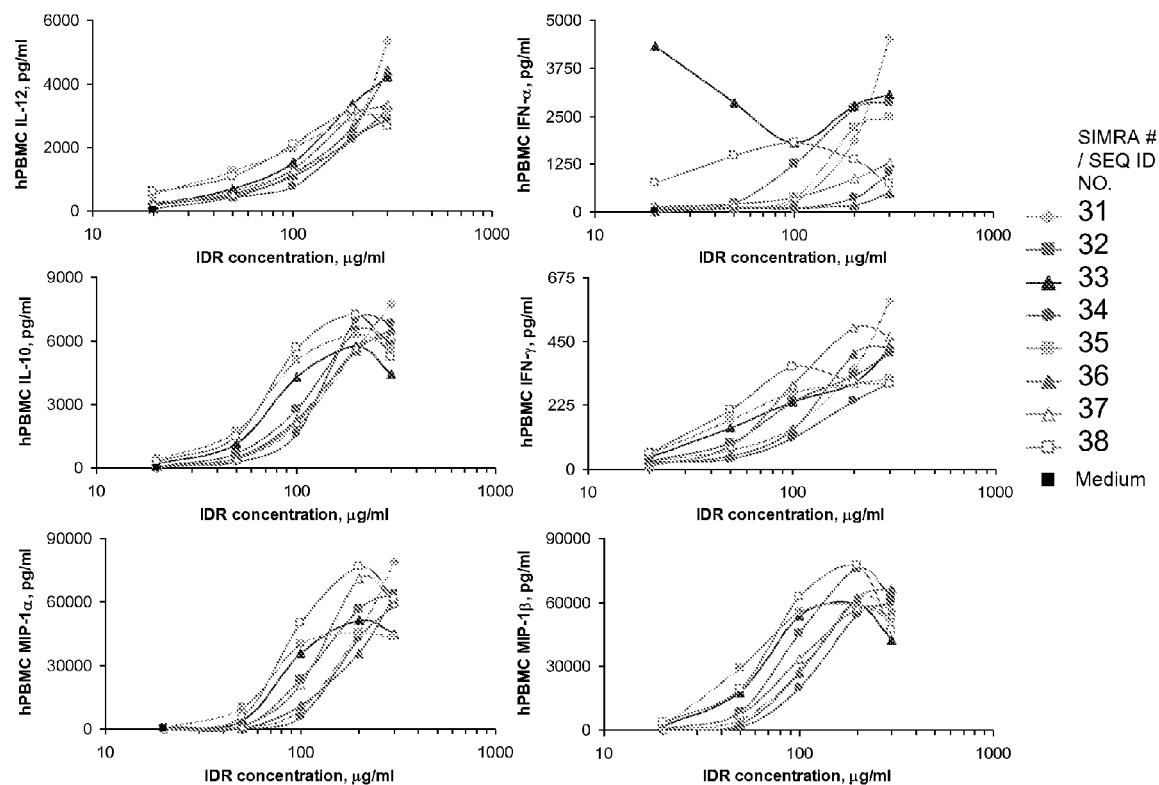
Figures 4J, 4K, 4L, 4M, 4N, 4O:
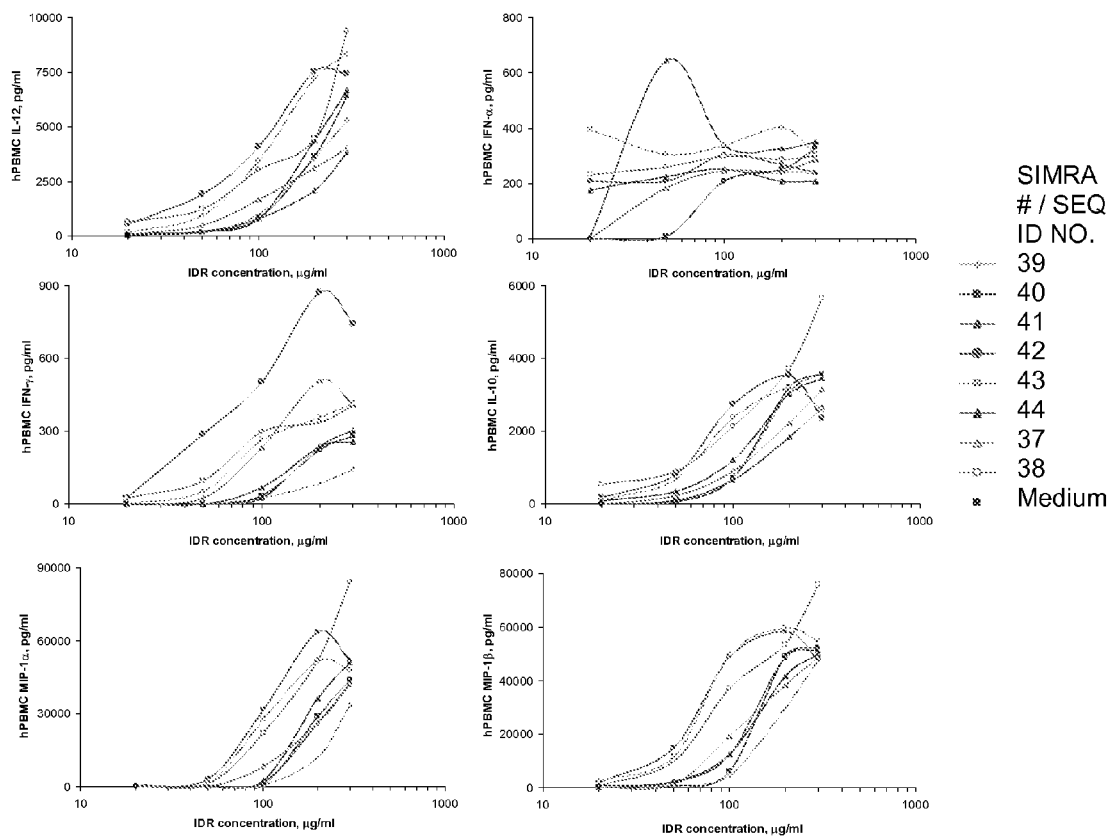
Figures 4P, 4Q, 4R, 4S, 4T, 4U:
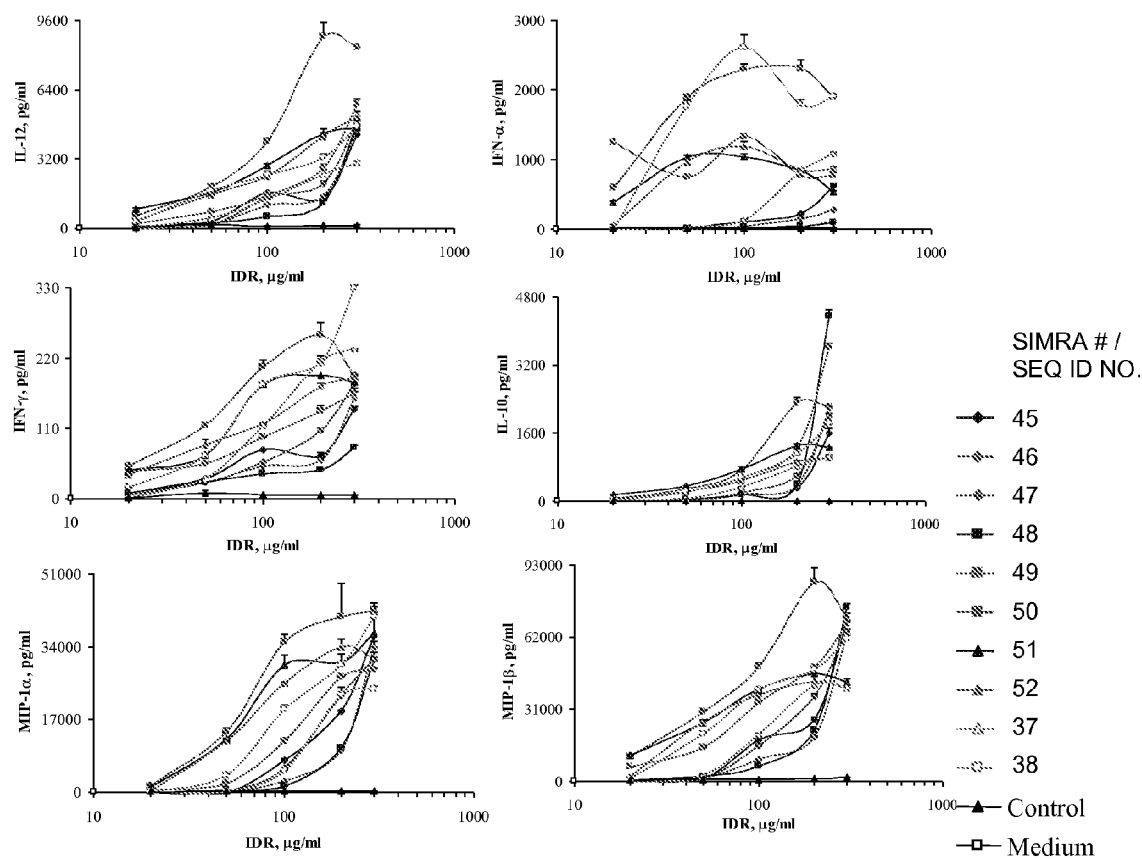
Figures 4A, 4V:
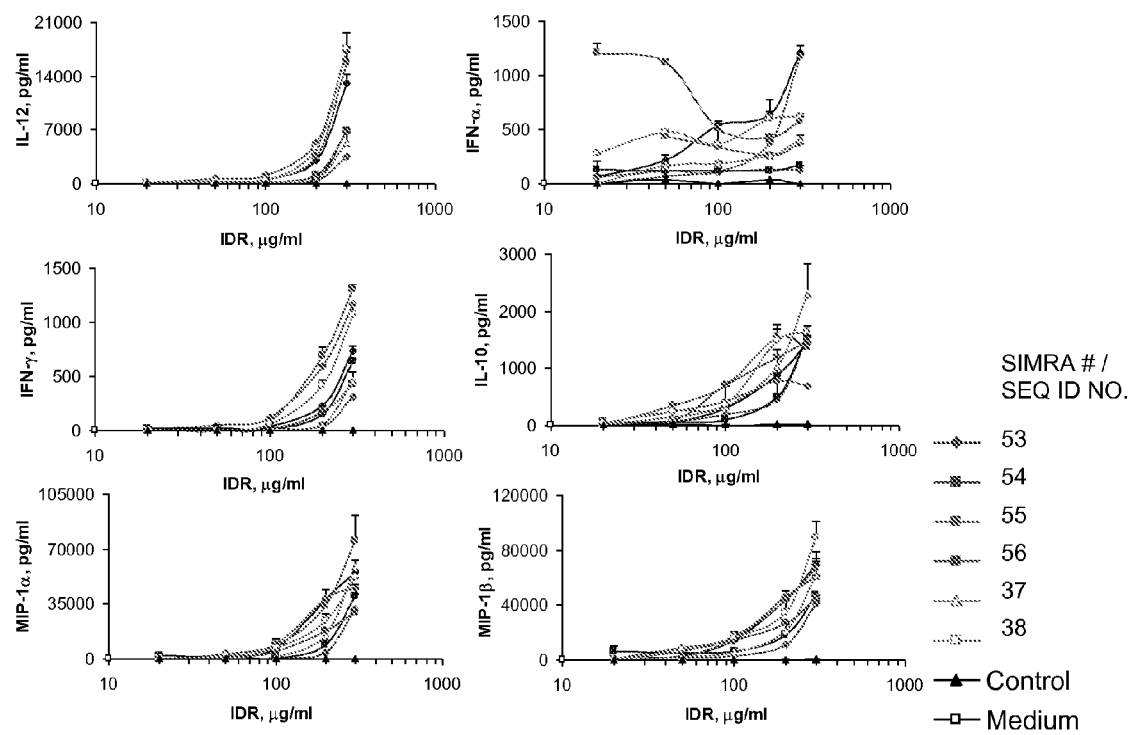
Figure 5A:
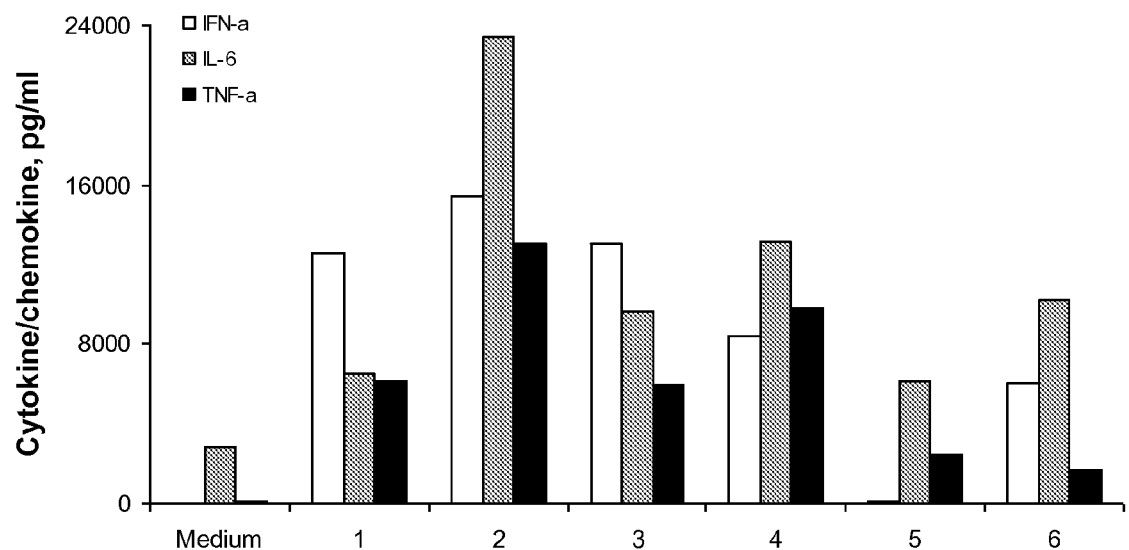
FIGS. 5A-5C depict cytokine and chemokine concentrations from human plasmacytoid dendritic cells (pDCs) that were isolated, treated, and analyzed according to example 3. Briefly, the pDCs were isolated from freshly obtained healthy human volunteer's blood PBMCs and cultured with 50 μg/ml dose of TLR7/8 agonists for 24 hr, and supernatants were collected and analyzed by Luminex multiplex assay for cytokine and chemokine levels. The data demonstrate that administration of a SIMRA according to the invention generates a distinct TLR-mediated cytokine and chemokine profile.
Figure 5B:
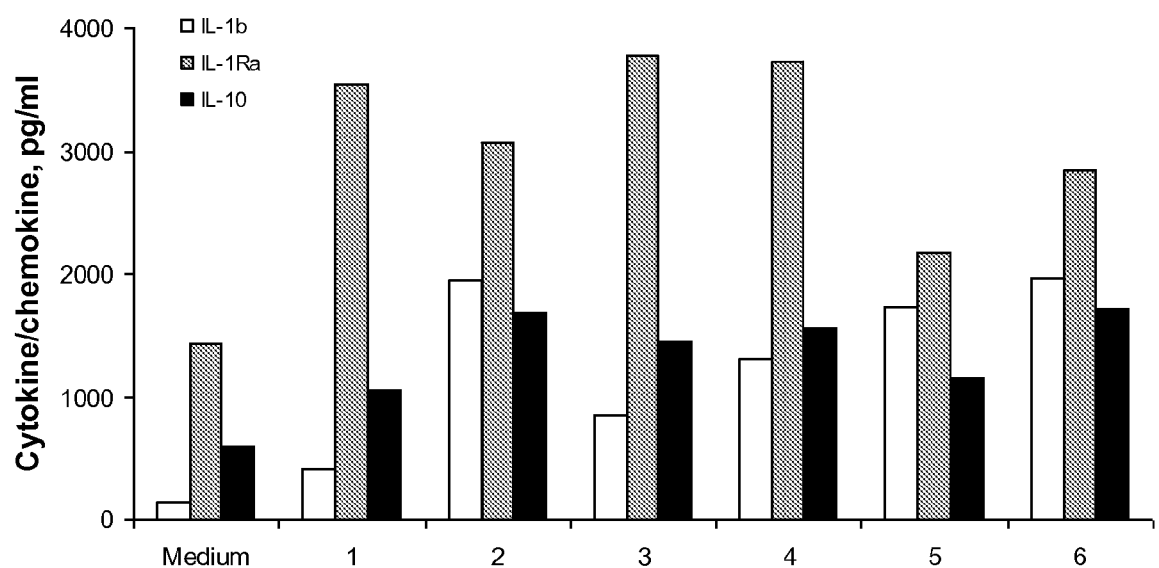
Figure 5C:
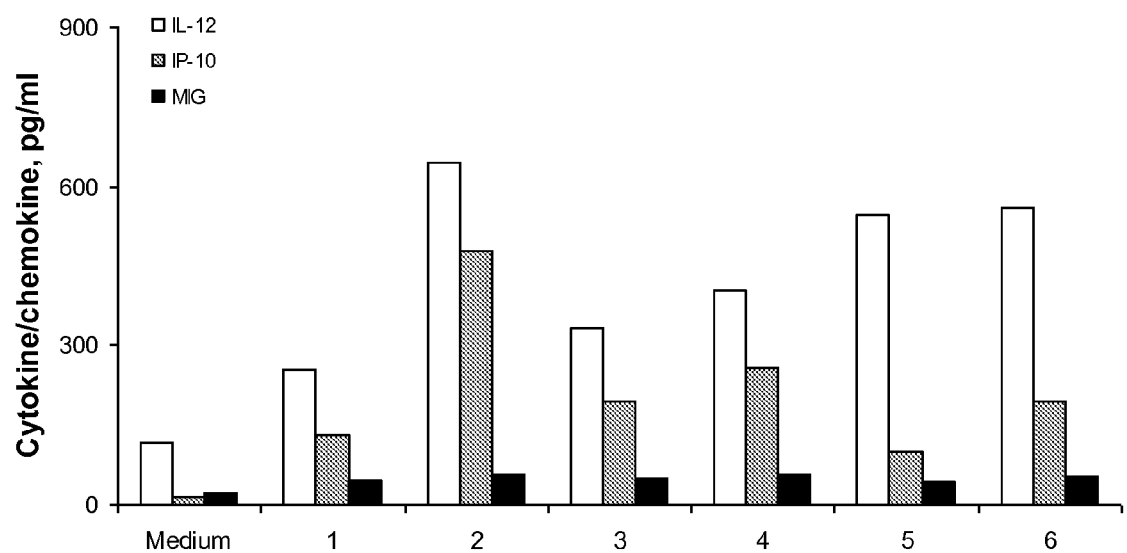
Figure 5D:
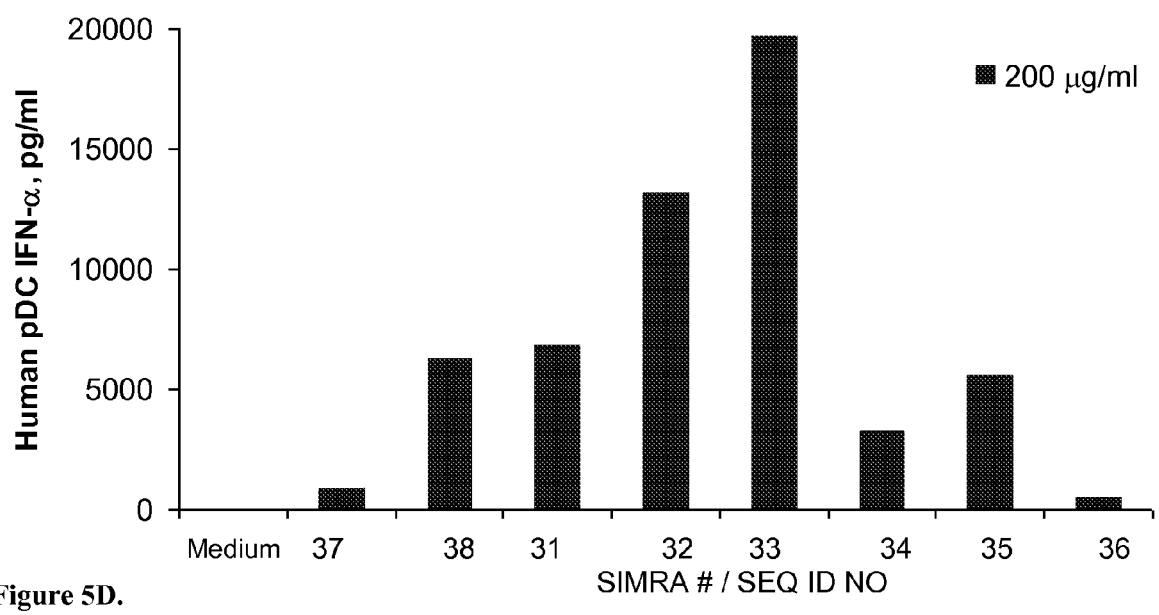
FIG. 5D depicts cytokine and chemokine concentrations from human plasmacytoid dendritic cells (pDCs) that were isolated, treated, and analyzed according to example 3. Briefly, the pDCs were isolated from freshly obtained healthy human volunteer's blood PBMCs and cultured with a 50 µg/ml or 200 µg/ml dose of TLR7/8 agonists for 24 hr, and supernatants were collected and analyzed by Luminex multiplex assay for cytokine and chemokine levels. The data demonstrate that administration of a SIMRA according to the invention generates a distinct TLR-mediated cytokine and chemokine profile.
Figure 6A:
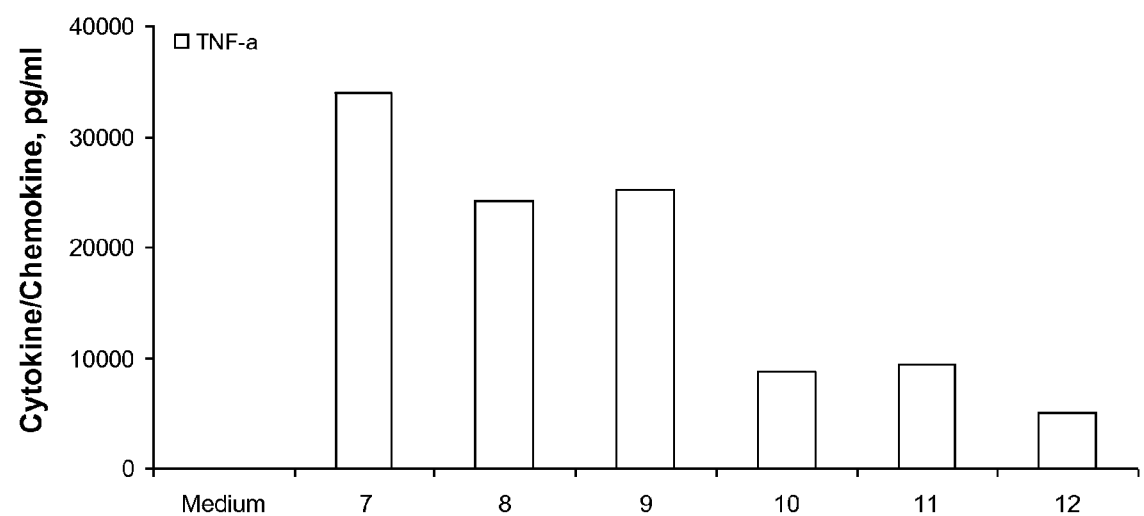
FIGS. 6A, 6B, 6C, 6E and 6F depict cytokine and chemokine concentrations from human plasmacytoid dendritic cells (pDCs) that were treated and analyzed according to example 3. Briefly, the pDC were isolated from freshly obtained healthy human volunteer's blood PBMCs and cultured with 200 µg/ml dose of TLR7/8 agonists for 24 hr, and supernatants were collected and analyzed by Luminex multiplex assay for cytokine and chemokine levels. The data demonstrate that administration of a SIMRA according to the invention generates a distinct TLR-mediated cytokine and chemokine profile.
Figure 6B:
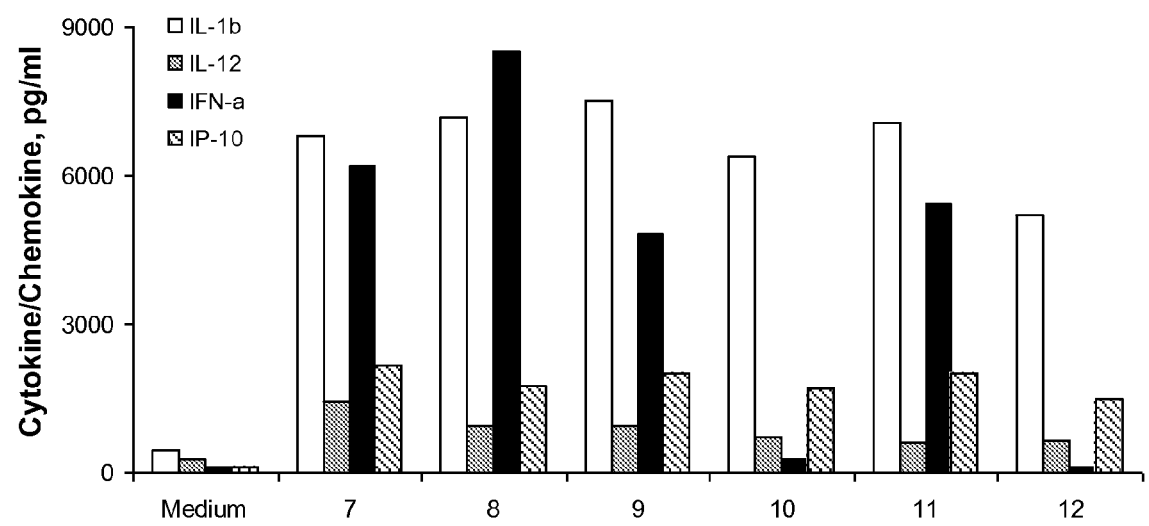
Figure 6C:
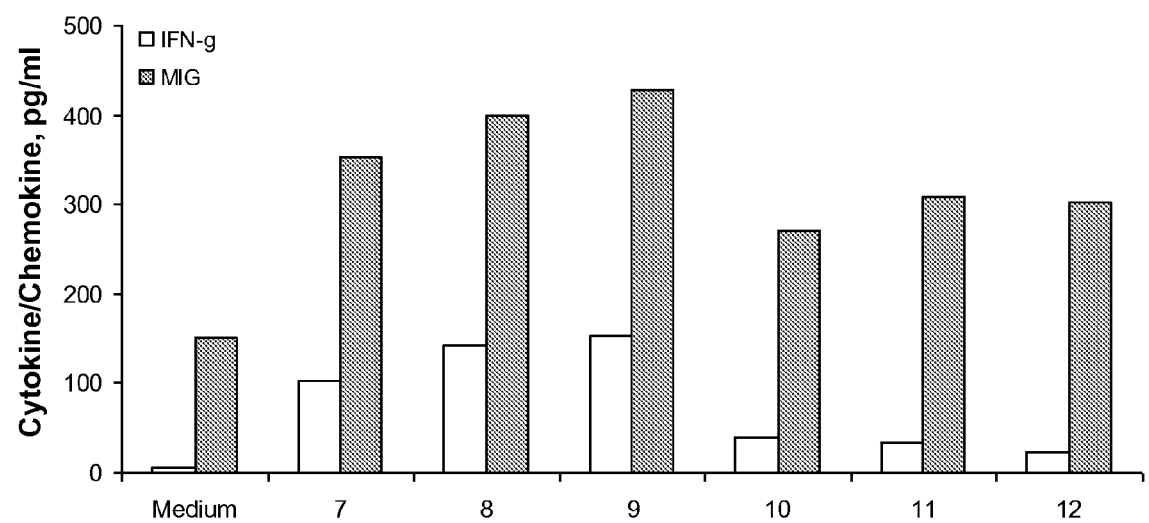
Figure 6D:
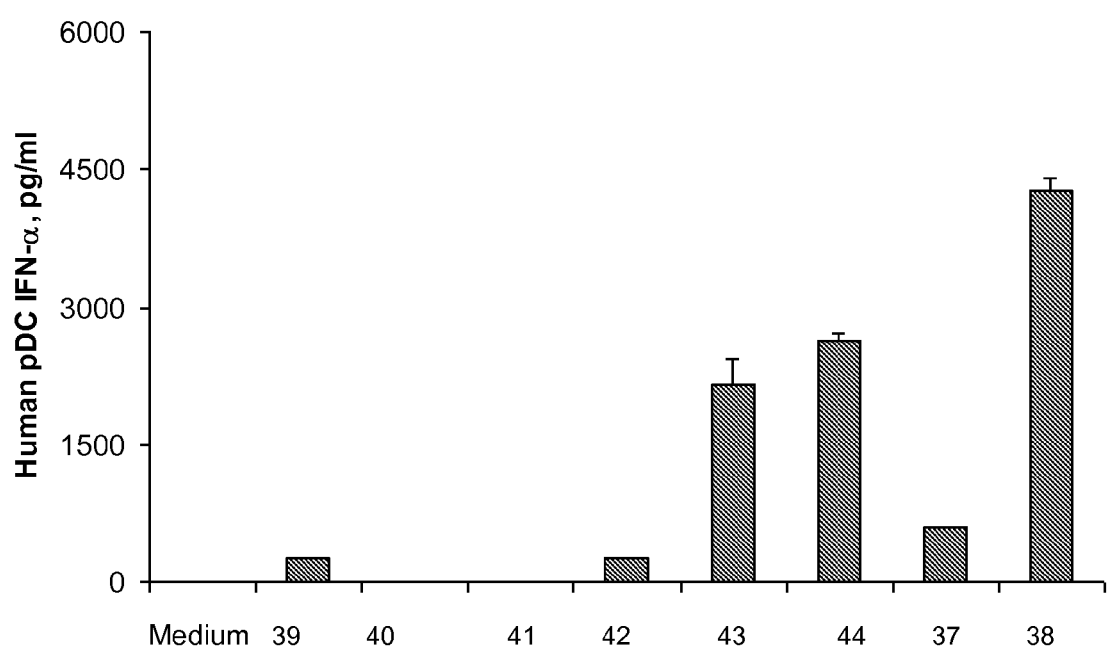
FIG. 6D depicts cytokine and chemokine concentrations from human plasmacytoid dendritic cells (pDCs) that were treated and analyzed according to example 3. Briefly, the pDC were isolated from freshly obtained healthy human volunteer's blood PBMCs and cultured with 100 µg/ml dose of TLR7/8 agonists for 24 hr, and supernatants were collected and analyzed by Luminex multiplex assay for cytokine and chemokine levels. The data demonstrate that administration of a SIMRA according to the invention generates a distinct TLR-mediated cytokine and chemokine profile.
Figure 6E:
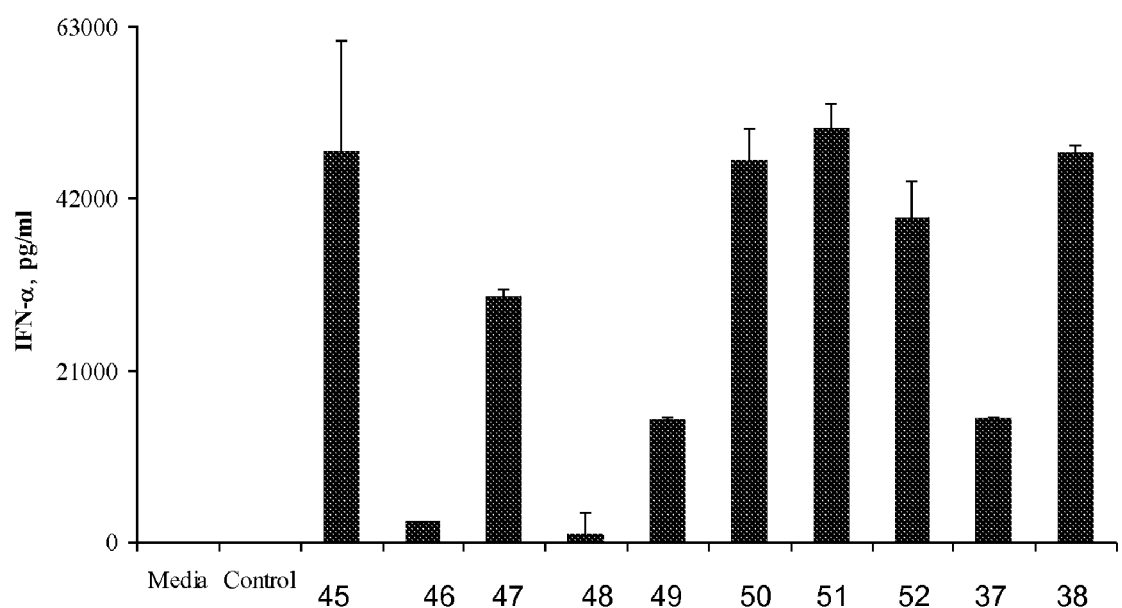
Figure 6F:
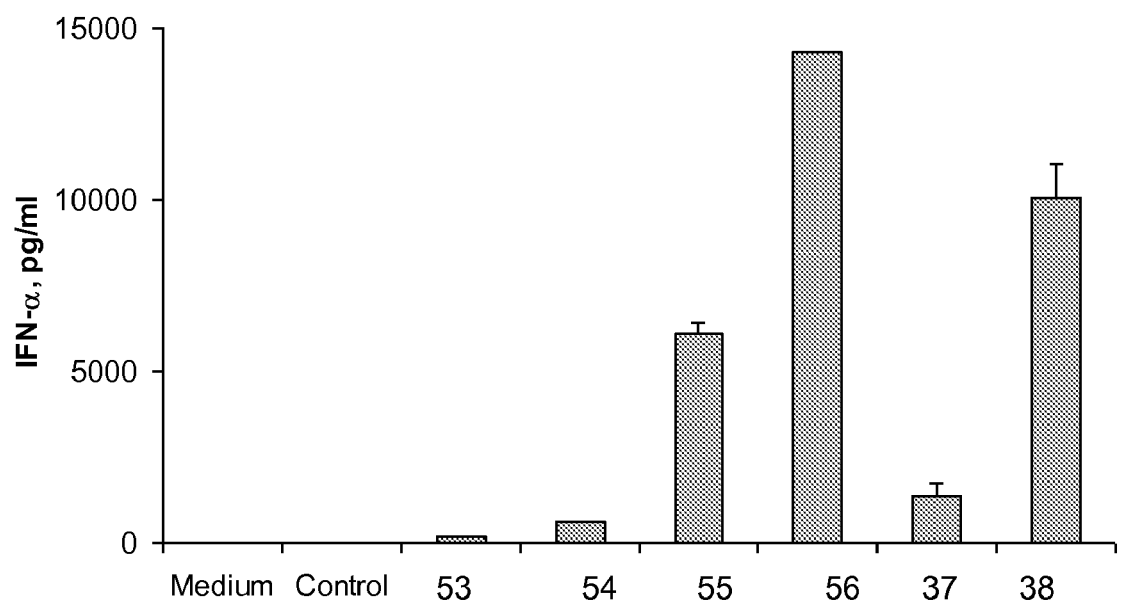
Figure 7A:
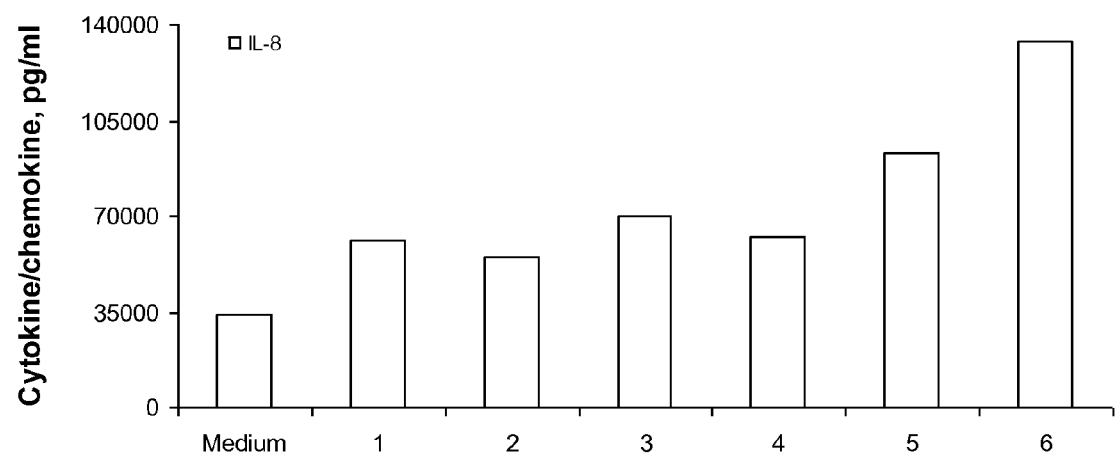
FIGS. 7A-7C depict cytokine and chemokine concentrations from human myeloid dendritic cells (mDCs) that were treated and analyzed according to example 3. Briefly, the mDCs were isolated from freshly obtained healthy human volunteer's blood PBMCs and cultured with 50 µg/ml dose of TLR7/8 agonists for 24 hr, and supernatants were collected and analyzed by Luminex multiplex assay for cytokine and chemokine levels. The data demonstrate that administration of a SIMRA according to the invention generates a distinct TLR-mediated cytokine and chemokine profile.
Figure 7B:
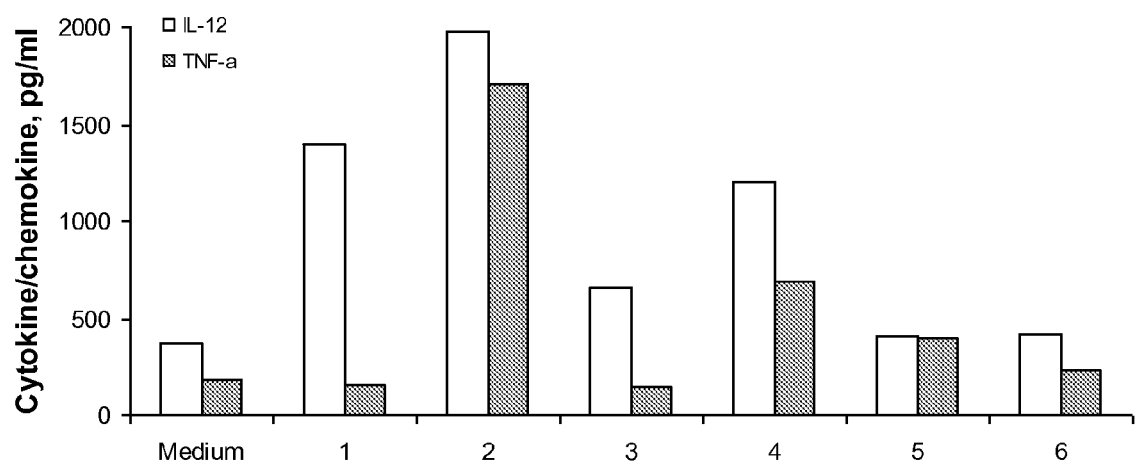
Figure 7C:
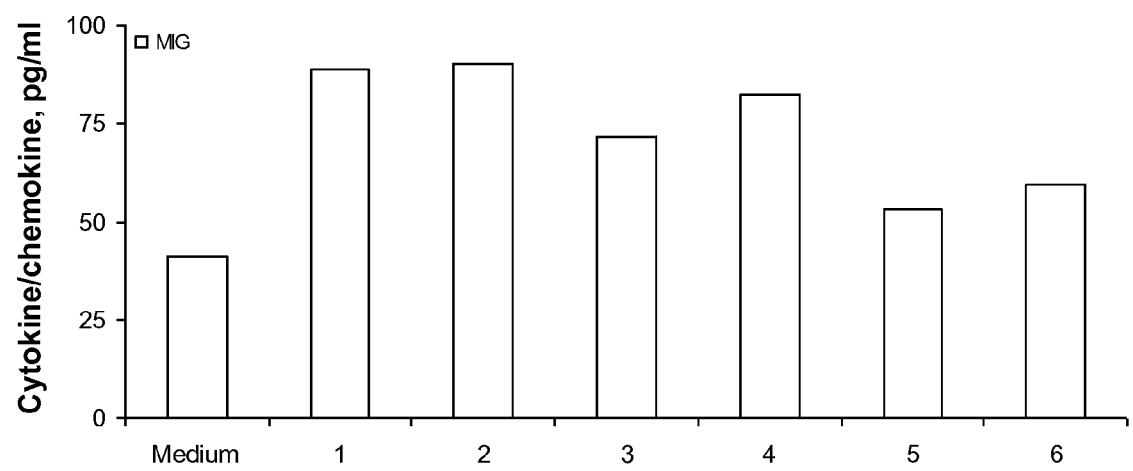
Figure 8A:
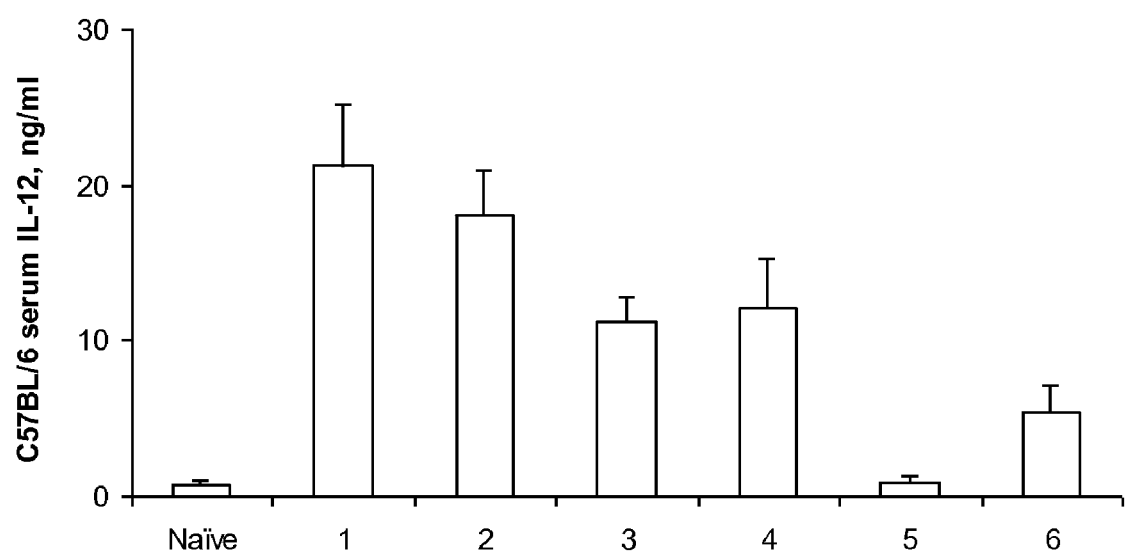
FIGS. 8A and 8B depict serum cytokine induction in C57BL/6 mice (n=3) 2 hours after they were treated and analyzed according to example 4. Briefly, the C57BL/6 mice were injected subcutaneously with 25 mg/kg dose of TLR7/8 agonists, and 2 hours after administration of the agonist, serum was analyzed for cytokine and chemokine levels, and IL-12 levels are presented. The data demonstrate that in vivo administration of a SIMRA according to the invention generates a distinct TLR-mediated cytokine and chemokine profile.
Figure 8B:
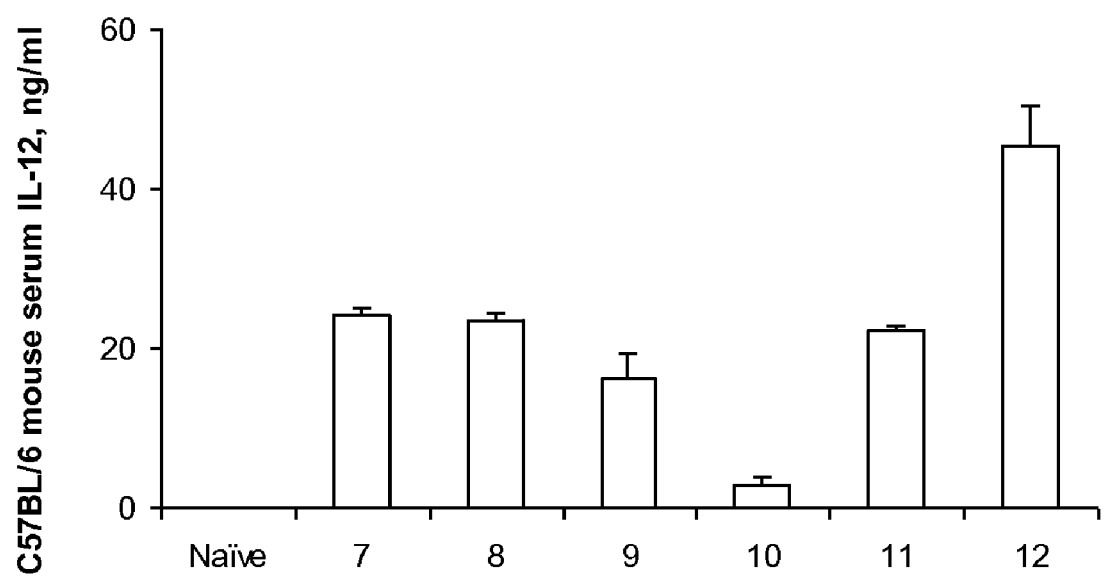
Figure 9A:
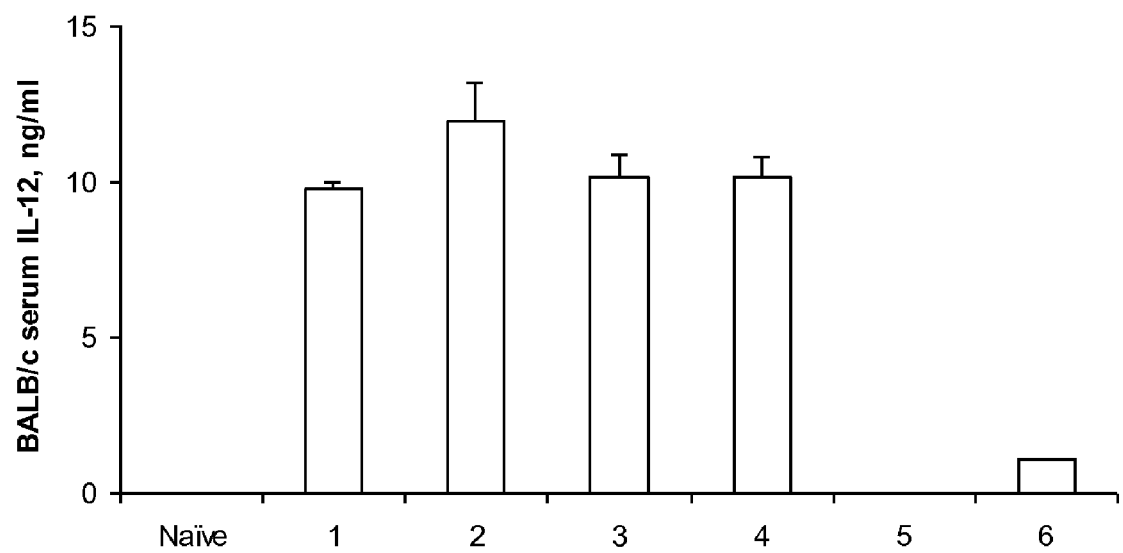
FIGS. 9A and 9B depict serum cytokine induction in BALB/c mice (n=3) 2 hours after they were treated and analyzed according to example 4. Briefly, the BALB/c mice injected subcutaneously with 25 mg/kg dose of TLR7/8 agonists, and 2 hours after administration of the agonist, serum was analyzed for cytokine and chemokine levels, and IL-12 levels are presented. The data demonstrate that in vivo administration of a SIMRA according to the invention generates a distinct TLR-mediated cytokine and chemokine profile.
Figure 9B:
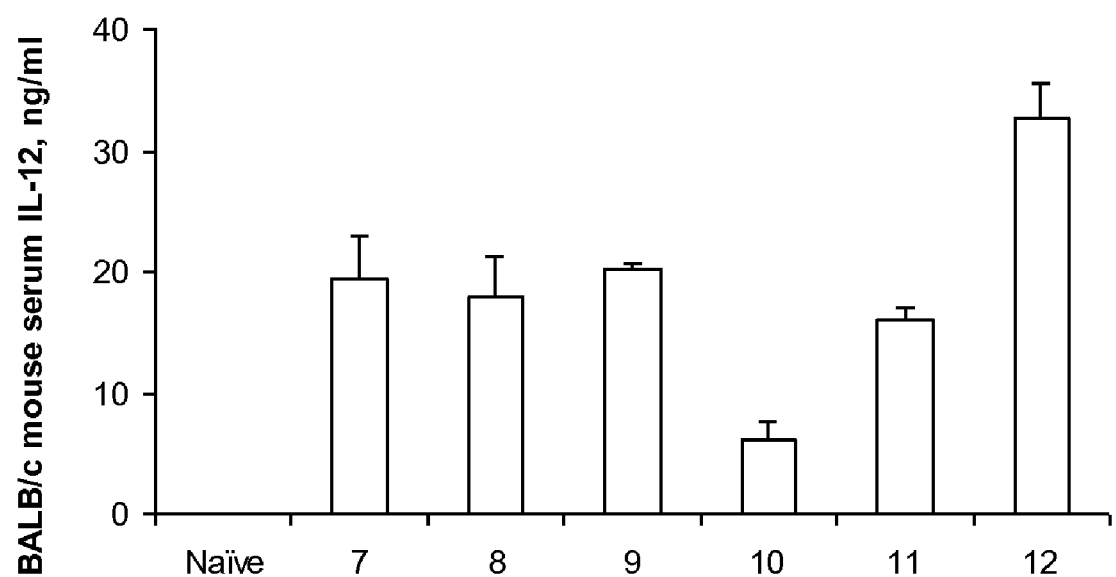
Figure 9C:
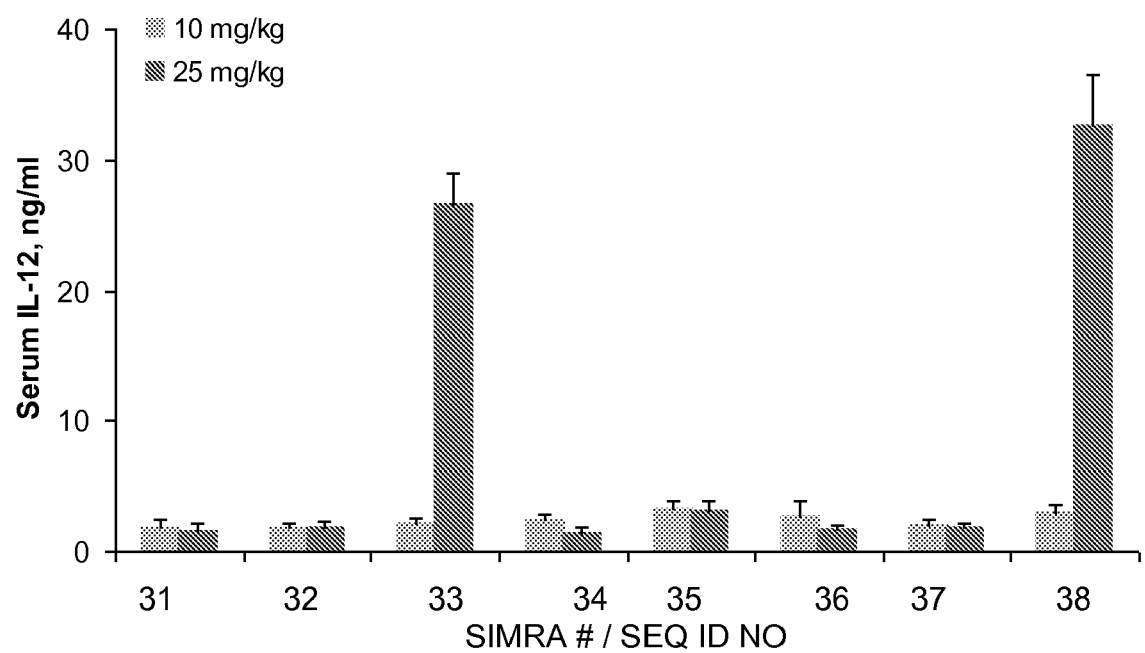
FIGS. 9C-9F depict serum cytokine induction in BALB/c mice (n=3) 2 hours after they were treated and analyzed according to example 4. Briefly, the BALB/c mice injected subcutaneously with 10 mg/kg or 25 mg/kg dose of TLR7/8 agonists, and 2 hours after administration of the agonist, serum was analyzed for cytokine and chemokine levels, and IL-12 levels are presented. The data demonstrate that in vivo administration of a SIMRA according to the invention generates a distinct TLR-mediated cytokine and chemokine profile.
Figure 9D:
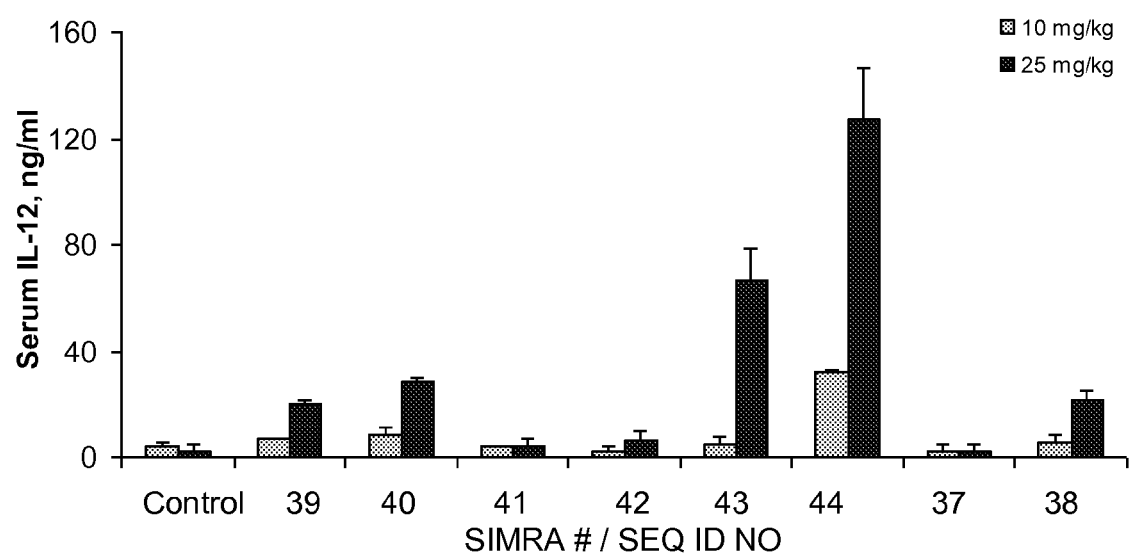
Figure 9E:
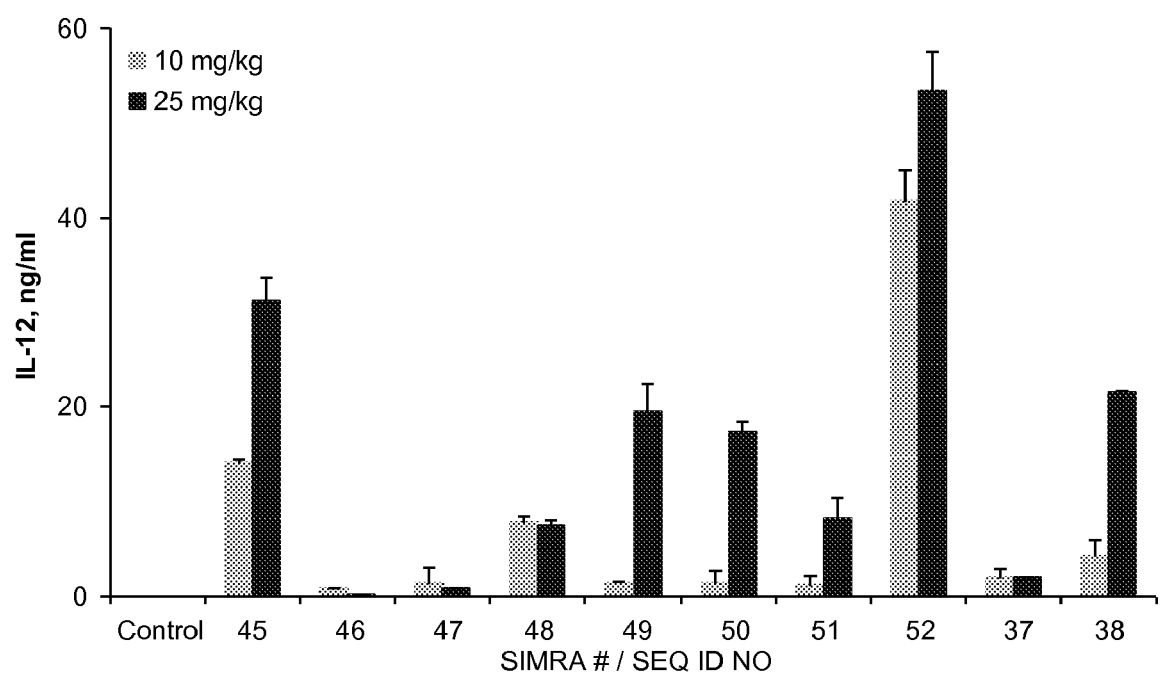
Figure 9F:
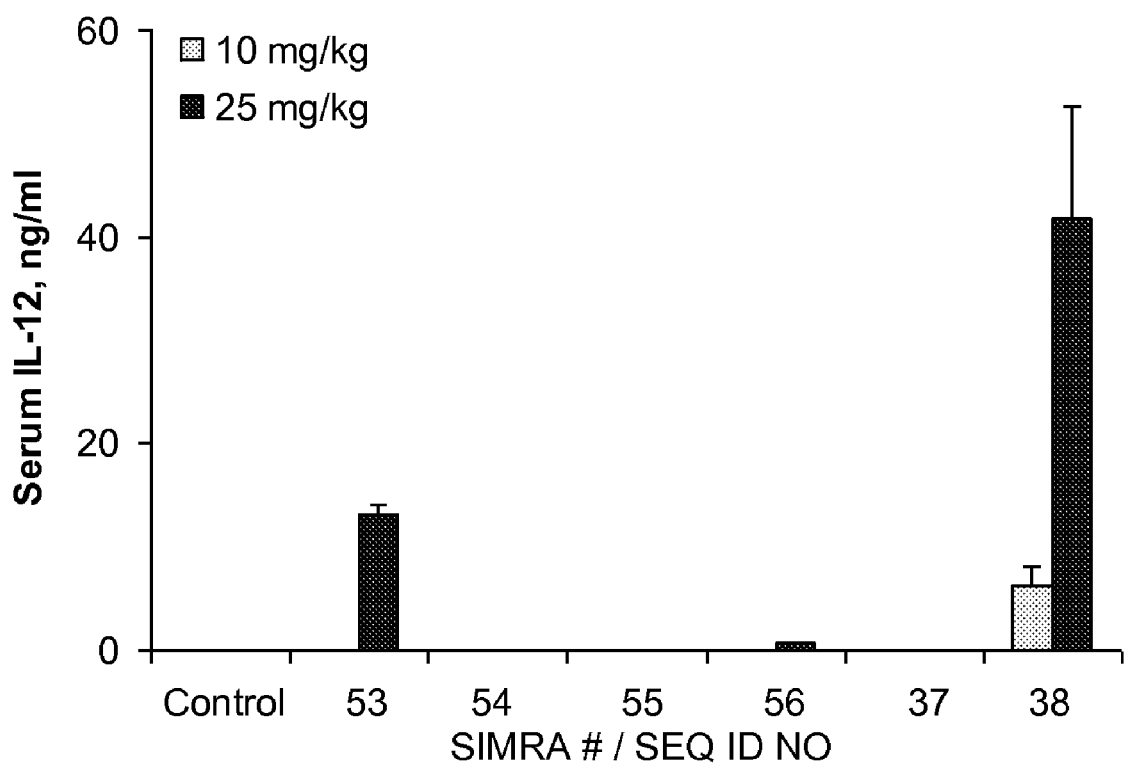
Figure 10A:
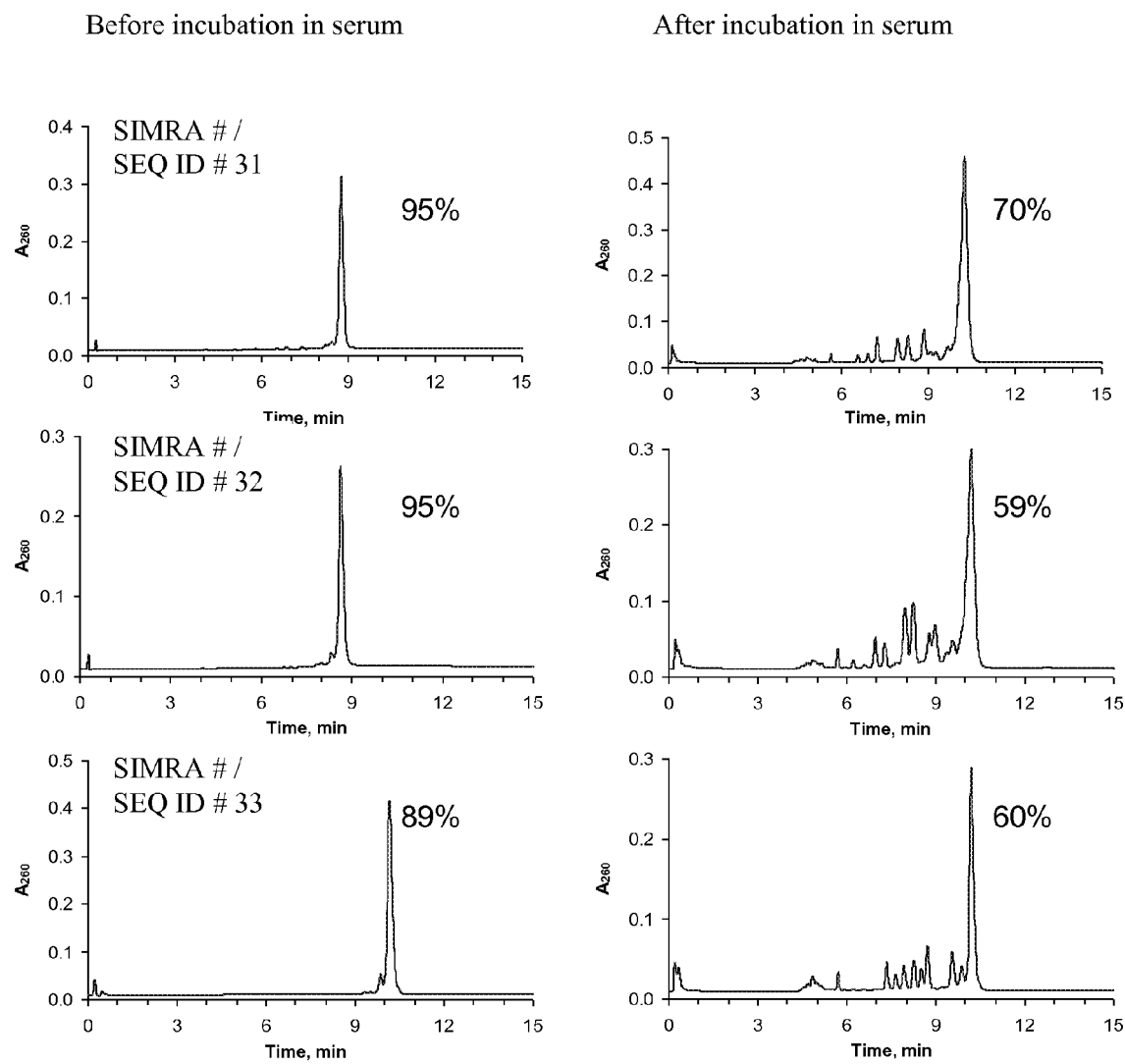
FIGS. 10A-10H depict serum stability of exemplar SIMRA compounds from Table 2 that were treated according to example 5. Briefly, approximately 0.5 OD of exemplar SIMRA compounds were individually incubated in 1% human serum in PBS for 30 minute at 37° C. At the end of the 30 minute incubation, the SIMRA compound was analyzed on anion-exchange HPLC to determine the percentage of full-length SIMRA compound that remained as compared to the amount of SIMRA compound present before serum treatment.
Figure 10B:
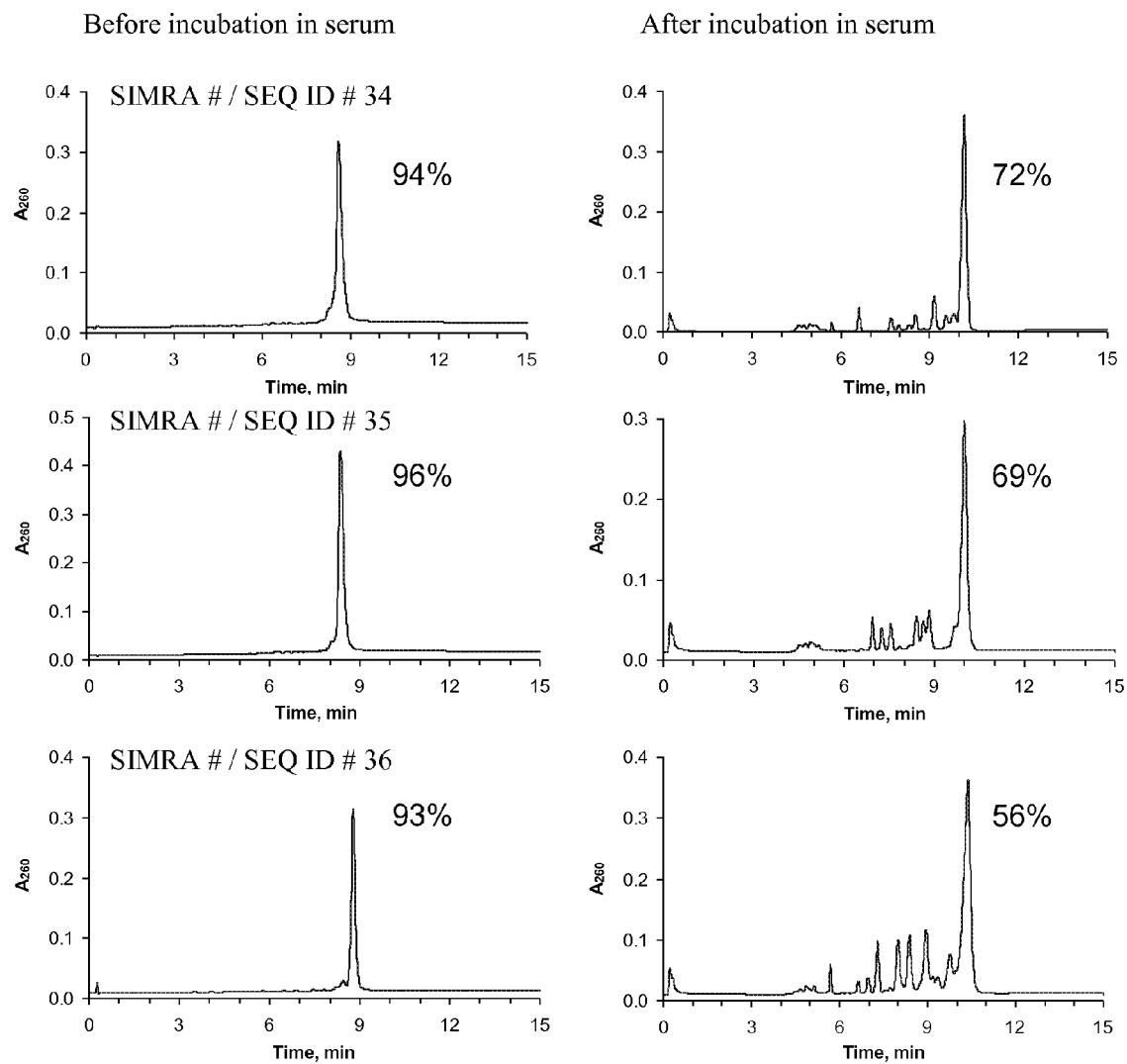
Figure 10C:
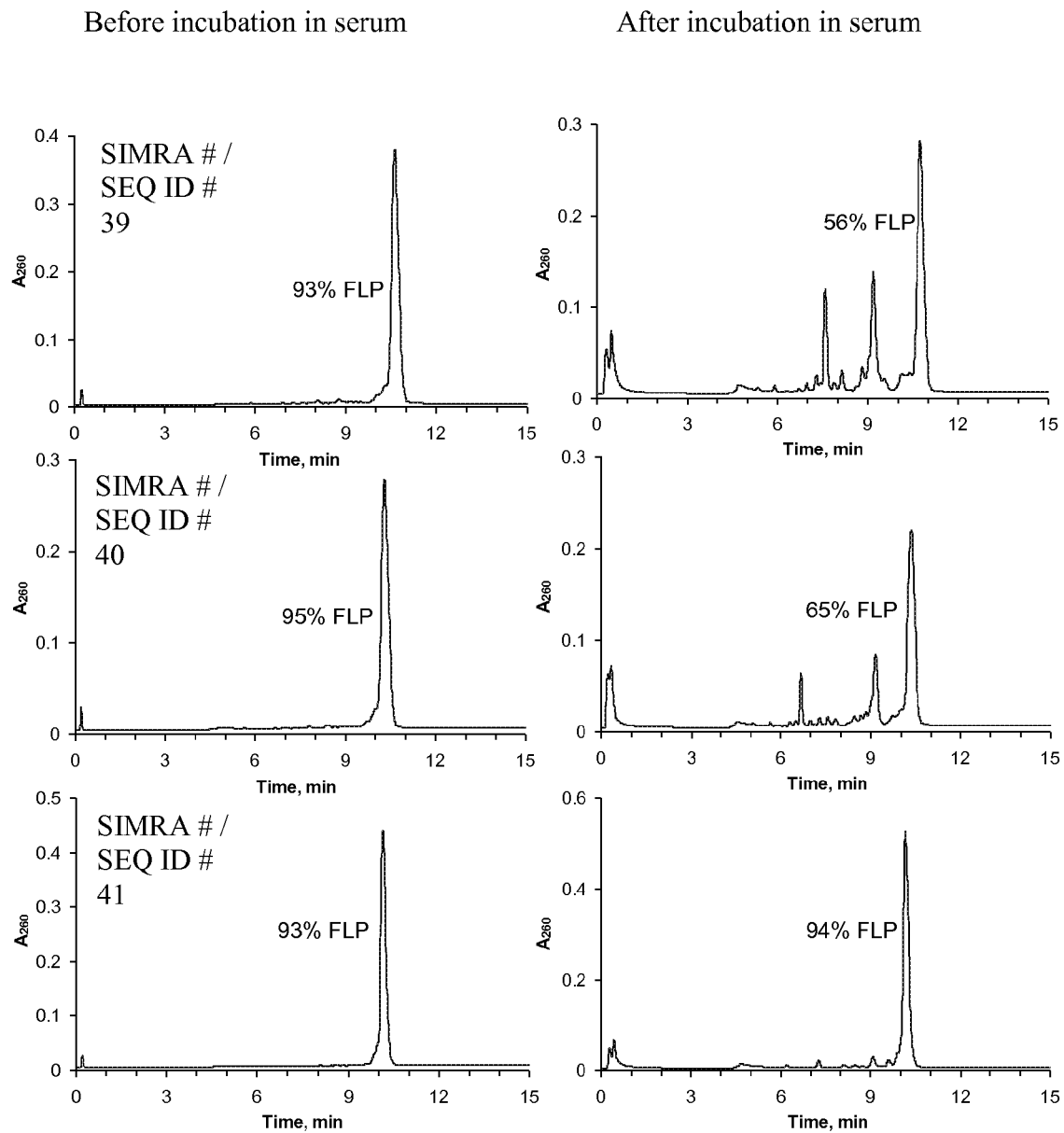
Figure 10D:
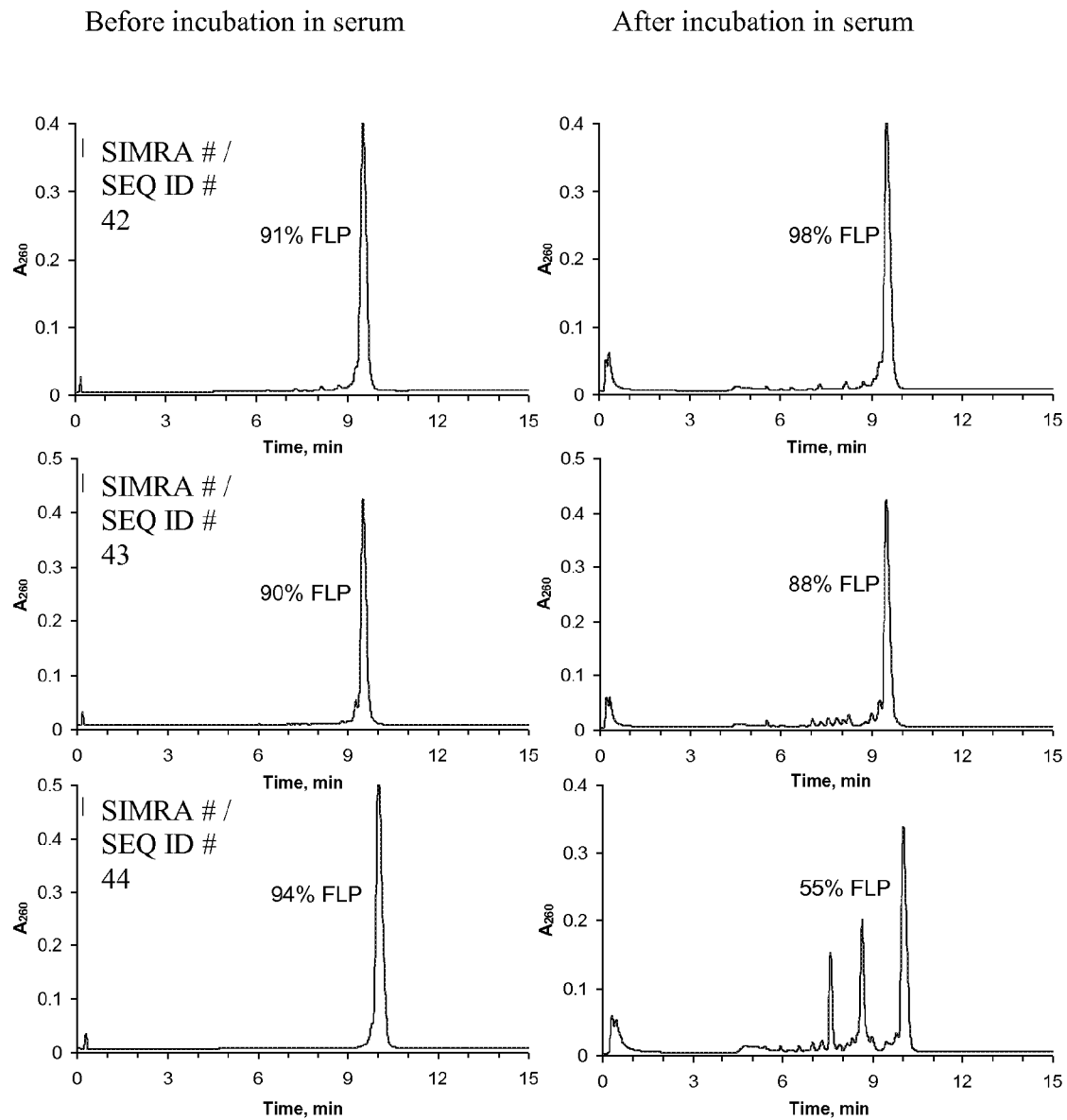
Figure 10E:
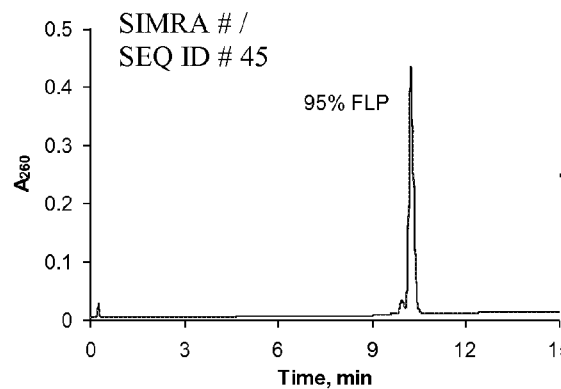
Figure 10E:
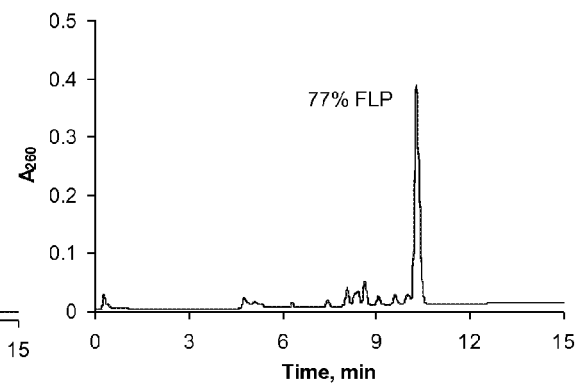
Figure 10E:
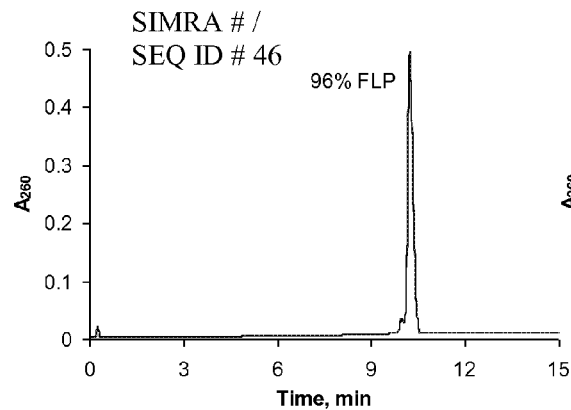
Figure 10E:
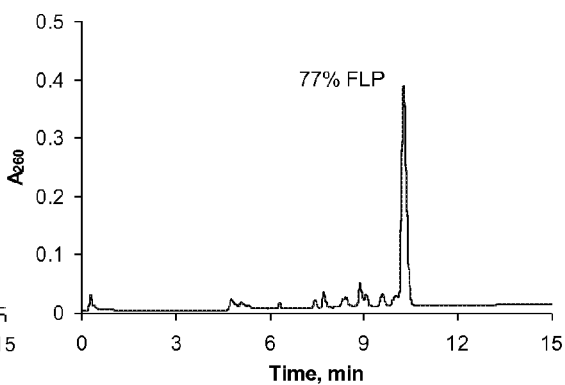
Figure 10E:
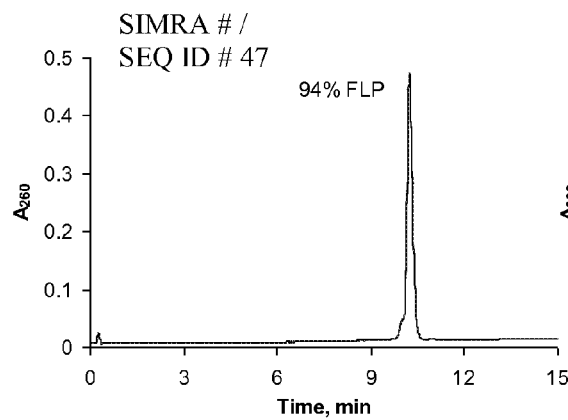
Figure 10E:
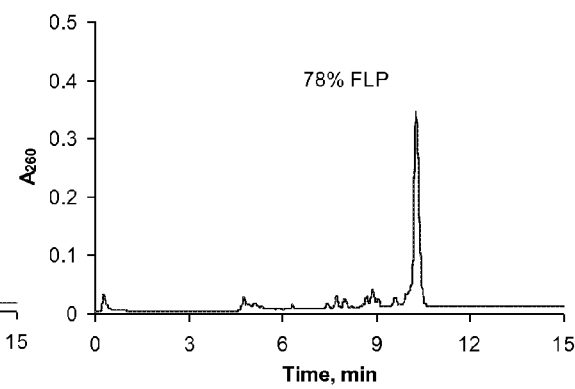
Figure 10F:
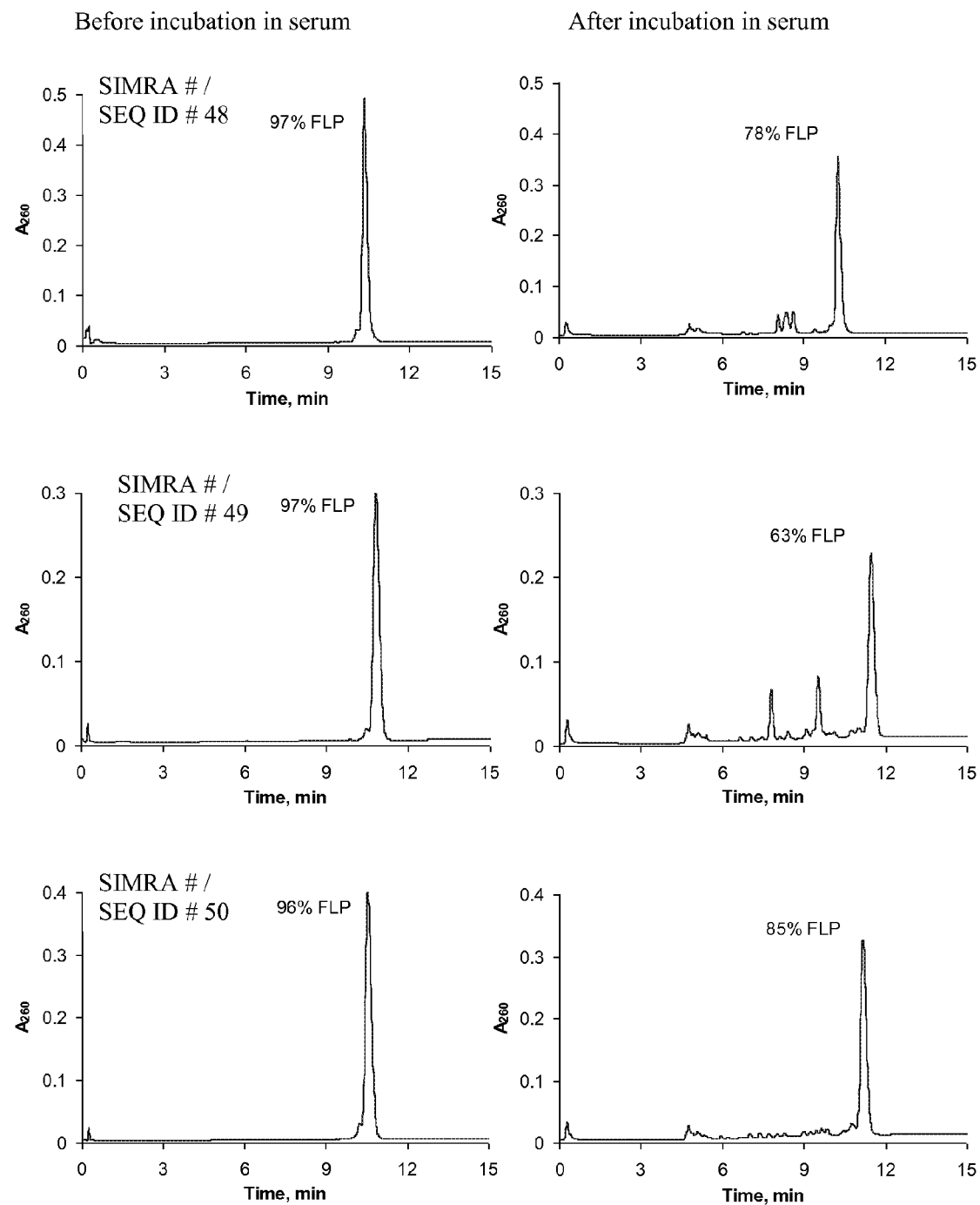
Figure 10G:
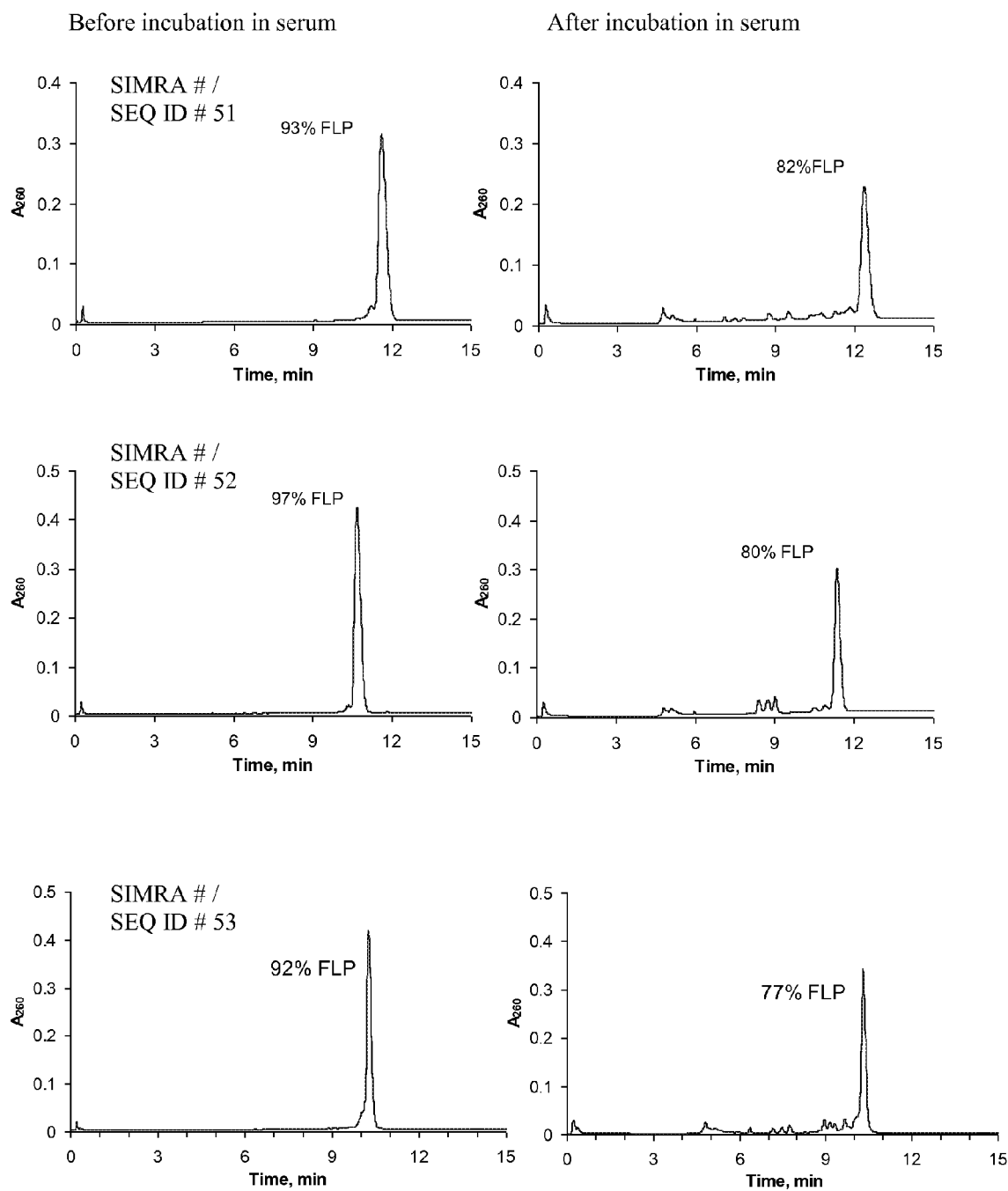
Figure 10H:
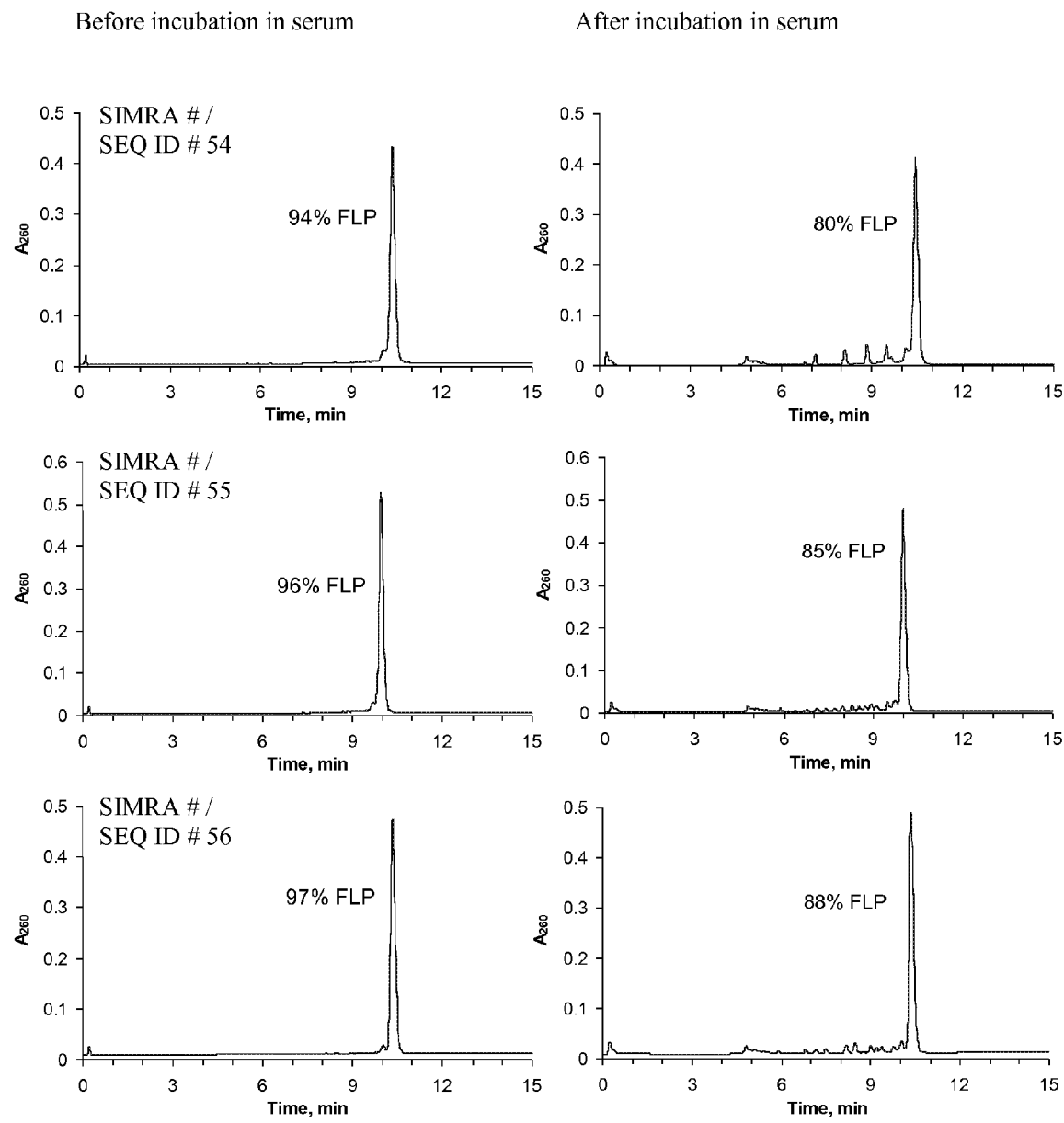

The invention relates to the therapeutic use of oligoribonucleotides as immune modulatory agents for immunotherapy applications. Specifically, the invention provides RNA-based oligonucleotides with improved in vivo stability that modulate the immune response through TLR7 alone, TLR7 and TLR8 or TLR8 alone (SIMRA compounds). By initiating diverse innate and acquired immune response mechanisms, for example through activation of dendritic cells and other antigen-presenting cells with stable agonists of TLR7 and/or TLR8, or SIMRA compounds, the resulting cytokine profile can lead to the destruction of pathogens, infected cells or tumor cells and development of antigen-specific antibody and CTL responses. Thus, the invention provides a diverse set of SIMRA compounds, each having its own unique immune regulatory characteristics. In this way, the scope and nature of the immune response can be customized for distinct medical indications by providing the SIMRA compound having the desired set of immune modulatory characteristics for that indication. The issued patents, patent applications, and references that are cited herein are hereby incorporated by reference to the same extent as if each was specifically and individually indicated to be incorporated by reference. In the event of inconsistencies between any teaching of any reference cited herein and the present specification, the latter shall prevail for purposes of the invention.

The invention provides methods for using SIMRA compounds to enhance the immune response. Such methods will find use in immunotherapy applications such as, but not limited to, treatment of cancer, autoimmune disorders, asthma, respiratory allergies, food allergies, skin allergies, and bacteria, parasitic, and viral infections in adult and pediatric human and veterinary applications. Thus, the invention further provides novel SIMRA compounds having optimal levels of immune modulatory effect for immunotherapy and methods for making and using such compounds. In addition, SIMRA compounds of the invention are useful as adjuvants or in combination with an agent useful for treating the disease or condition that does not diminish the immune modulatory effect of the SIMRA compound for prevention and treatment of diseases.

DEFINITIONS

The term "2'-substituted ribonucleoside" or "2'-substituted arabinoside" generally includes ribonucleosides or arabinonucleosides in which the hydroxyl group at the 2' position of the pentose moiety is substituted to produce a 2'-substituted or 2'-O-substituted ribonucleoside. In certain embodiments, such substitution is with a lower hydrocarbyl group containing 1-6 saturated or unsaturated carbon atoms, with a halogen atom, or with an aryl group having 6-10 carbon atoms, wherein such hydrocarbyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Arabinonucleosides of the invention include, but are not limited to, arabino-G, arabino-C, arabino-U, arabino-A. Examples of 2'-O-substituted ribonucleosides or 2'-O-substituted-arabinosides include, without limitation 2'-amino, 2'-fluoro, 2'-allyl, 2'-O-alkyl and 2'-propargyl ribonucleosides or arabinosides, 2'-O-methylribonucleosides or 2'-O-methylarabinosides and 2'-O-methoxyethoxyribonucleosides or 2'-O-methoxyethoxyarabinosides.

The term "3'", when used directionally, generally refers to a region or position in a polynucleotide or oligonucleotide 3' (toward the 3' position of the sugar) from another region or position in the same polynucleotide or oligonucleotide.

The term "5'", when used directionally, generally refers to a region or position in a polynucleotide or oligonucleotide 5' (toward the 5' position of the sugar) from another region or position in the same polynucleotide or oligonucleotide.

The term "about" generally means that the exact number is not critical. Thus, the number of ribonucleoside residues in the oligoribonucleotides is not critical, and oligoribonucleotides having one or two fewer ribonucleoside or arabinonucleoside residues, or from one to several additional ribonucleoside or arabinonucleoside residues are contemplated as equivalents of each of the embodiments described above.

The term "adjuvant" generally refers to a substance which, when added to an immunogenic agent such as vaccine or antigen, enhances or potentiates an immune response to the agent in the recipient host upon exposure to the mixture.

The term "airway inflammation" generally includes, without limitation, inflammation in the respiratory tract caused by infectious allergens, including asthma.

The term "allergen" generally refers to an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic (e.g., IgE) immune response upon exposure to the molecule.

The term "allergy" generally includes, without limitation, food allergies, respiratory allergies, and skin allergies.

The term "antigen" generally refers to a substance that is recognized and selectively bound by an antibody or by a T cell antigen receptor. Antigens may include but are not limited to peptides, proteins, nucleosides, nucleotides, and combinations thereof. Antigens may be natural or synthetic and generally induce an immune response that is specific for that antigen.

The term "autoimmune disorder" generally refers to disorders in which "self" antigen undergo attack by the immune system.

Blocking 3' or 5' degradation or "cap" or "capping" means that the 3' or 5' end of the oligoribonucleotide is attached to another molecule (e.g linker or other non-RNA nucleotide) to sufficiently inhibit nuclease degradation (e.g. 3' exonuclease degradation).

The term "carrier" generally encompasses any excipient, diluent, filler, salt, buffer, stabilizer, solubilizer, oil, lipid, lipid containing vesicle, microspheres, liposomal encapsulation, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, e.g., *Remington's Pharmaceutical Sciences,* 18th Edition, ed. A. Gennaro, Mack Publishing Co., Easton, Pa., 1990.

The term "co-administration" generally refers to the administration of at least two different substances sufficiently close in time to modulate an immune response. Co-administration includes simultaneous administration of at least two different substances.

The term "complementary" generally means having the ability to hybridize to a nucleic acid. Such hybridization is ordinarily the result of hydrogen bonding between complementary strands, preferably to form Watson-Crick or Hoogsteen base pairs, although other modes of hydrogen bonding, as well as base stacking can also lead to hybridization.

The term "immune modulatory oligoribonucleotide" generally refers to an oligoribonucleotide that induces or represses an immune response when administered to a vertebrate, such as a fish, fowl or mammal.

The term "in combination with" generally means in the course of treating the same disease in the same patient, and includes administering a SIMRA compound and an agent useful for treating the disease or condition that does not diminish the immune modulatory effect of the SIMRA compound in any order, including simultaneous administration or co-administration, as well as temporally spaced order from a few seconds up to several days apart. Such combination treatment may also include more than a single administration of a SIMRA compound, and/or independently the agent. The administration of the SIMRA compound and the agent may be by the same or different routes.

The term "individual" or "subject" generally refers to a mammal, such as a human. Mammals generally include, but are not limited to, humans, non-human primates, rats, mice, cats, dogs, horses, cattle, cows, pigs, sheep, and rabbits.

The term "linear synthesis" generally refers to a synthesis that starts at one end of the immune modulatory oligoribonucleotide and progresses linearly to the other end. Linear synthesis permits incorporation of either identical or non-identical (in terms of length, base composition and/or chemical modifications incorporated) monomeric units into the immune modulatory oligoribonucleotides.

The term "linker" generally refers to any moiety that can be attached to an oligoribonucleotide by way of covalent or non-covalent bonding through a sugar, a base, or the backbone. The linker can be used to attach two or more nucleosides or can be attached to the 5' and/or 3' terminal nucleotide in the oligoribonucleotide. Such linker can be either a non-nucleotidic linker or a nucleotidic linker.

The term "modified nucleoside" generally is a nucleoside that includes a modified heterocyclic base, a modified sugar moiety, or any combination thereof. In some embodiments, the modified nucleoside is a non-natural pyrimidine or purine nucleoside, as herein described. For purposes of the invention, a modified nucleoside, a pyrimidine or purine analog or non-naturally occurring pyrimidine or purine can be used interchangeably and refers to a nucleoside that includes a non-naturally occurring base and/or non-naturally occurring sugar moiety. For purposes of the invention, a base is considered to be non-natural if it is not guanine, cytosine, adenine or uracil. In some embodiments, the modified nucleoside is a 2'-substituted ribonucleoside an arabinonucleoside or a 2'-deoxy-2'-substituted-arabinoside that can be substituted into selected positions of the oligoribonucleotide to improve stability without interfering with TLR7 or TLR8 activity.

The term "modulation" or "stimulation" generally refers to change, such as an increase in a response or qualitative difference in a response, which can arise from eliciting and/or enhancement of a response.

The term "non-nucleotidic linker" generally refers to a chemical moiety other than a nucleotidic linkage that can be attached to an oligoribonucleotide by way of covalent or non-covalent bonding. Preferably such non-nucleotidic linker is from about 2 angstroms to about 200 angstroms in length, and may be either in a cis or trans orientation.

The term "nucleotidic linkage" generally refers to a chemical linkage to join two nucleosides through their sugars (e.g. 3'-3',2'-3',2'-5',3'-5') consisting of a phosphate, non-phosphate, charged, or neutral group (e.g., phosphodiester, phosphorothioate or phosphorodithioate) between adjacent nucleosides.

The term "peptide" generally refers to polypeptides that are of sufficient length and composition to affect a biological response, e.g., antibody production or cytokine activity whether or not the peptide is a hapten. The term "peptide" may include modified amino acids (whether or not naturally or non-naturally occurring), where such modifications include, but are not limited to, phosphorylation, glycosylation, pegylation, lipidization, and methylation.

The terms "pharmaceutically acceptable" or "physiologically acceptable" generally refer to a material that does not interfere with the effectiveness of a compound according to the invention and that is compatible with a biological system such as a cell, cell culture, tissue, or organism. Preferably, the biological system is a living organism, such as a vertebrate.

The term a "pharmaceutically effective amount" generally refers to an amount sufficient to affect a desired biological effect, such as a beneficial result. Thus, a "pharmaceutically effective amount" will depend upon the context in which it is being administered. A pharmaceutically effective amount may be administered in one or more prophylactic or therapeutic administrations.

The term "SIMRA" generally refers to stabilized immune modulatory RNA compounds which are recognized as ligands by TLR7 and/or TLR8, wherein the compounds may contain single-stranded RNA (ssRNA) and/or double-stranded RNA (dsRNA), and modifications to protect or stabilize its 3' ends (e.g. by blocking 3' degradation or by capping the 3' ends or by linking the 3' ends of two or more oligoribonucleotides), provided that the SIMRA is or would be more stable in vivo than an unmodified oligoribonucleotide and, thus, affect its immune modulatory capabilities. The SIMRA may contain modified oligoribonucleotides. The SIMRA compound may also contain modifications to protect its 5' ends (e.g., by blocking 5' degradation or capping the 5' ends) to further improve the stability of the oligoribonucleotide(s). The SIMRA can be linear or branched, with nucleic acids being polymers of ribonucleosides linked through, for example, phosphodiester, phosphorothioate, or alternate linkages. A SIMRA may consist of a purine (adenine (A) or guanine (G) or derivatives thereof (e.g. 7-deaza-G, arabino-G and arabino-A)) or pyrimidine (cytosine (C) or uracil (U), or derivatives thereof (e.g. arabino-C and arabino-U)) base covalently attached to a ribose sugar residue or a derivative thereof.

The term "treatment" generally refers to an approach intended to obtain a beneficial or desired result, which may include alleviation of symptoms, or delaying or ameliorating a disease progression.

The term "viral disease" generally refers to a disease that has a virus as its etiologic agent, including but not limited to hepatitis B, hepatitis C, influenza, acquired immunodeficiency syndrome (AIDS), and herpes zoster.

In a first aspect, the invention provides novel SIMRA compounds. The present inventors have discovered that modification of an immune modulatory oligoribonucleotide to protect its 3' end (e.g. by blocking 3' degradation or capping the 3' end or by linking the 3' ends of two or more oligoribonucleotides) surprisingly affects its immune modulatory capabilities. In addition, it has been determined that this protection surprisingly improves the stability of the oligoribonucleotides, removing the need for lipid association or other means of protection. Further, blocking 5' degradation or capping the 5' end in addition to or in combination with protecting the 3'-end can also improve the stability of the oligoribonucleotide.

In the present invention activation of TLR8 and induction of unique immune responses (e.g. changes in cytokine and/or chemokine profiles) with novel SIMRA compounds is demonstrated. Moreover, the incorporation of certain chemical modification(s) in such human TLR8 activating RNAs can also activate TLR7, resulting in distinct immune response(s) and a change in cytokine and/or chemokine profiles. Thus, the present inventors have surprisingly discovered that through activation of TLR8 and/or TLR7 cytokine and/or chemokine profiles associated therewith can be modulated by using modified chemical structures, including modified bases, modified sugars, backbone, linkers, linkages, and/or caps as part of an immune modulatory oligoribonucleotide.

In one embodiment, the invention provides an immune modulatory compound comprising at least two RNA-based oligonucleotides linked at their 3' ends, or an internucleoside linkage or a functionalized nucleobase or sugar to a non-nucleotidic linker. Such embodiment of the invention may have at least one accessible 5' end, which may be capped or uncapped. It has been determined that this structure provides further stability (e.g. inhibition of exonuclease activity) to the SIMRA compounds without the need for lipid association or other protection. An "accessible 5' end" means that the 5'-terminus of the SIMRA is not modified in such a way as to prevent the SIMRA compound from modulating an immune response through TLR7 and/or TLR8.

In another embodiment of this aspect of the invention comprises at least two oligoribonucleotides, wherein the immune modulatory compound has a structure including, but not limited to, those as detailed in Formulas I-X in Table 1.

TABLE 1

Oligoribonucleotide Formulas I-X

| Formula I | Domain A | Domain B |
|---|---|---|
| | 5'    3' | 3'    5' |
| | ▬▬▬X▬▬▬ | |

TABLE 1-continued

Oligoribonucleotide Formulas I-X

Formula II a

```
        Domain A       Domain B       Domain C
       5'     3'       5'     3'      3'     5'
       ━━━━━━━━━X━━━━━━━━━━━X━━━━━━━━━━
```

Formula II b

```
        Domain A       Domain B       Domain C
       3'     5'       5'     3'      3'     5'
       ━━━━━━━━━X━━━━━━━━━━━X━━━━━━━━━━
```

Formula III

```
    Domain A       Domain B       Domain C       Domain D
   5'     3'      5'     3'      5'     3'      3'     5'
   ━━━━━━━━X━━━━━━━━━━X━━━━━━━━━━X━━━━━━━━━━
```

Formula IV

```
              5'
               \ Domain A
                \
               3' 5' Domain B
                X━━━━━━━
                X━━━━━━
               3' 3' Domain C
                /
               / Domain D
              5'
```

Formula V

```
        Domain A       Domain B
       5'      3'      3'      5'
       ━━━━━━━━━X━━━━━━━━━━
                    |
                   ●
```

Formula VI

```
          5'          5'
           \  3'  3' /
            ━━━X━━━
            ━━━X━━━
           / 5'  3' \
          3'         5'
```

Formula VII

```
         5' Domain A 3'
              \    /
               \  / Domain B
              3' 5'
                X
                |
                3'
              Domain C
                |
                5'
```

Formula VIII

```
       5' ━━━━━━━X 3'
                    \ 5'
               3' X━━━━━━━
```

Formula IX

```
        Domain A       Domain B
       5'━━━━━━━X━━━━━━━━━3'
       3'━━━━━━━X━━━━━━━━━5'
        Domain B       Domain A
```

Formula X

```
      ⎡ Domain A   Domain B        Domain A   Domain B    ⎤
      ⎢5'━━━━━━X━━━━━━━3'  5'━━━━━━X━━━━━━━3'⎥
      ⎢          3'━━━━━━X━━━━━━5'                        ⎥
      ⎣          Domain B   Domain A                      ⎦ n
```

Domains A, B, C, and D may be independently from about 2 to about 35 ribonucleotides, and in some embodiments from about 2 to about 20, or from about 2 to about 12, or from about 2 to about 11 or from about 2 to about 8 ribonucleotides in length. Domains A, B, C, and/or D may or may not be identical. Domains A, B, C, and D may independently be 5'-3' or 2'-5' RNA having or not having a self-complementary domain, a homo or hetero ribonucleotide sequence, or a linker. "n" may be from 1 to an unlimited number.

"X" is a linker joining or capping Domains A, B, C, and/or D that may be through a 3' or 5' linkage, a phosphate group, a nucleobase, a non-RNA nucleotide, or a non-nucleotidic linker that may be aliphatic, aromatic, aryl, cyclic, chiral, achiral, a peptide, a carbohydrate, a lipid, a fatty acid, mono- tri- or hexapolyethylene glycol, or a heterocyclic moiety, or combinations thereof.

In a further embodiment, the invention provides a SIMRA compound comprising at least two oligoribonucleotides linked by a non-nucleotidic linker, wherein the sequences of the immune modulatory oligoribonucleotides may be at least partially self-complementary. As would be recognized by one skilled in the art, the complementary sequence of the oligoribonucleotides allows for intermolecular hydrogen bonding thereby giving the oligoribonucleotides secondary structure. Additional oligoribonucleotides can bind together thereby creating a chain, or multimers, of oligoribonucleotides according to the invention.

Similar considerations apply to intermolecular base pairing between immune modulatory oligoribonucleotides of different base sequence. Thus, where a plurality of immune modulatory oligoribonucleotides is used together, the plurality of immune modulatory oligoribonucleotides may, but need not, include sequences that are at least partially complementary to one another. In one embodiment the plurality of immune modulatory oligoribonucleotide includes an immune modulatory oligoribonucleotide having a first sequence and an immune modulatory oligoribonucleotide having a second sequence, wherein the first sequence and the second sequence are at least 50 percent complementary. For example, as between two 8-mers that are at least 50 percent complementary, they may form 4, 5, 6, 7, or 8 G-C, A-U, and/or G-U wobble basepairs. Such basepairs may, but need not necessarily, involve bases located at either end of the complementary immune modulatory oligoribonucleotides. The degree of complementarity may depend on the alignment between immune modulatory oligoribonucleotides, and such alignment may or may not include single- or multiple-nucleoside overhangs. In other embodiments, the degree of complementarity is at least 60 percent, at least 70 percent, at least 80 percent, at least 90 percent, or even 100 percent.

As would be recognized by one skilled in the art, the depicted immune modulatory compounds may have secondary structure because the sequences of the domains are complementary allowing for intermolecular hydrogen bonding. Moreover, as can be imagined from Formulas I through X, additional linked RNA-based oligonucleotides can bind through intermolecular hydrogen bonding thereby creating a chain, or multimers, wherein any number of linked RNA-based oligonucleotides may be incorporated.

In another embodiment, the invention provides an immune modulatory compound comprising at least two RNA-based oligonucleotides linked at their 3' or 5' ends, or through an internucleoside linkage or a functionalized nucleobase or sugar to a non-nucleotidic linker, and wherein a linker (e.g. cap) is attached to at least one 5' end. It has been determined that this structure provides further stability (e.g. inhibition of exonuclease activity) to the SIMRA compounds. The 5'-terminus of the SIMRA is not modified in such a way as to prevent the SIMRA compound from modulating an immune response through TLR7 and/or TLR8.

In some embodiments, the oligoribonucleotides each independently have from about 2 to about 35 ribonucleoside residues. Thus in certain embodiments the oligoribonucleotide can independently be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 ribonucleotides long. Preferably the oligoribonucleotide is from about 4 to about 30 ribonucleoside residues, more preferably from about 4 to about 20 ribonucleoside residues or from about 4 to about 11 ribonucleoside residues. In some embodiments, the immune modulatory oligoribonucleotides comprise oligoribonucleotides having from about 1 to about 18, or from about 1 to about 11, or from about 5 to about 14 ribonucleoside residues. In some embodiments, one or more of the oligoribonucleotides have 11 ribonucleotides or from about 8 to about 14 ribonucleotides or from about 10 to about 12 ribonucleotides. In the context of immune modulatory oligoribonucleotides, preferred embodiments have from about 1 to about 35 ribonucleotides, preferably from about 5 to about 26 ribonucleotides, more preferably from about 13 to about 26 ribonucleotides. Preferably, the immune modulatory oligoribonucleotide comprises at least one phosphodiester, phosphorothioate, or phosphorodithioate interribonucleoside linkage.

In exemplar embodiments each ribonucleoside unit includes a heterocyclic base and a pentofuranosyl, trehalose, arabinose, 2'-deoxy-2'-substituted arabinose, 2'-O-substituted ribose or arabinose, or hexose sugar group. The ribonucleoside residues can be coupled to each other by any of the numerous known interribonucleoside linkages. Such interribonucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone interribonucleoside linkages. Possible sites of conjugation for the ribonucleotide are indicated in Formula XI, below, wherein B represents a heterocyclic base.

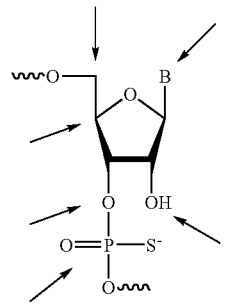

Formula XI

The SIMRA compounds of the invention can include naturally occurring ribonucleosides, modified ribonucleosides, or mixtures thereof.

In the present invention, novel SIMRA compounds are recognized by human TLR8 and incorporation of certain chemical modification(s) in such human TLR8 activating RNAs can causes them to be recognized by human TLR7 and induce immune responses. Such chemical modifications include, but are not limited to, guanine analogues such as 7-deaza-G, ara-G, 6-thio-G, Inosine, Iso-G, loxoribine, TOG (7-thio-8-oxo)-G, 8-bromo-G, 8-hydroxy-G, 5-aminoformycin B, Oxoformycin, 7-methyl-G, 9-p-chlorophenyl-8-aza-G, 9-phenyl-G, 9-hexyl-guanine, 7-deaza-9-benzyl-G, 6-Chloro-7-deazaguanine, 6-methoxy-7-deazaguanine, 8-Aza-7-deaza-G(PPG), 2-(Dimethylamino)guanosine, 7-Methyl-6-thioguanosine, 8-Benzyloxyguanosine, 9-Deazaguanosine, and 1-(B-D-ribofuranosyl)-2-oxo-7-deaza-8-methyl-purine. Chemical modifications also include, but are not limited to, adenine analogues such as 9-benzyl-8-hydroxy-2-(2-methoxyethoxy)adenine, 2-Amino-N2-O—, methyladenosine, 8-Aza-7-deaza-A, 7-deaza-A, ara-A, Vidarabine, 2-Aminoadenosine, N1-Methyladenosine, 8-Azaadenosine, 5-Iodotubercidin. Chemical modifications also include, but are not limited to, cytosine and uracil analogues such as pseudouridine, ara-C, ara-U, 5-methylcytidine, 4-thiouridine, N4-ethyluridine, zebularine, 5-aminoallyluridine, N3-methyluridine, 5-fluorouridine.

The "immune modulatory oligoribonucleotides" according to the invention are SIMRA compounds that comprise at least two oligoribonucleotides linked covalently or non-covalently at their 3'- or 2'-ends or functionalized ribose or functionalized ribonucleobase via a non-nucleotidic or a nucleotidic linker. Several examples of linkers are set forth below. Non-covalent linkages include, but are not limited to, electrostatic interaction, hydrophobic interactions, π-stacking interactions and hydrogen bonding.

In yet other embodiments, the non-nucleotidic linker is an organic moiety having functional groups that permit attachment to the oligoribonucleotide. Such attachment preferably is by a stable covalent linkage. As a non-limiting example, the linker may be attached to any suitable position on the nucleotide. In some preferred embodiments, the linker is attached to the 3'-hydroxyl. In such embodiments, the linker preferably comprises a hydroxyl functional group, which preferably is attached to the 3'-hydroxyl by means of a phosphate-based linkage like, phosphodiester, phosphorothioate, phosphorodithioate, methylphosphonate or non-phosphate-based linkages.

In some embodiments, the non-nucleotidic linker is a small molecule, macromolecule or biomolecule, including, without limitation, polypeptides, antibodies, lipids, antigens, allergens, and oligosaccharides. In some other embodiments, the non-nucleotidic linker is a small molecule. For purposes of the invention, a small molecule is an organic moiety having a molecular weight of less than 1,000 Da. In some embodiments, the small molecule has a molecular weight of less than 750 Da.

In some embodiments, the small molecule is an aliphatic or aromatic hydrocarbon, either of which optionally can include, either in the linear chain connecting the oligoribonucleotides or appended to it, one or more functional groups including, but not limited to, hydroxy, amino, thiol, thioether, ether, amide, thioamide, ester, urea, or thiourea. The small molecule can be cyclic or acyclic. Examples of small molecule linkers include, but are not limited to, amino acids, carbohydrates, cyclodextrins, adamantane, cholesterol, haptens and antibiotics. However, for purposes of describing the non-nucleotidic linker, the term "small molecule" is not intended to include a nucleoside.

In some embodiments, the non-nucleotidic linker is an alkyl linker or amino linker. The alkyl linker may be branched or unbranched, cyclic or acyclic, substituted or unsubstituted, saturated or unsaturated, chiral, achiral or racemic mixture. The alkyl linkers can have from about 2 to about 18 carbon atoms. In some embodiments such alkyl linkers have from about 3 to about 9 carbon atoms. Some alkyl linkers include one or more functional groups including, but not limited to, hydroxy, amino, thiol, thioether, ether, amide, thioamide, ester, urea, and thioether. Such alkyl linkers can include, but are not limited to, 1-propanol, 1,2 propanediol, 1,3 propanediol, 1,2,3, propanetriol, triethylene glycol, hexaethylene glycol, polyethylene glycol linkers (e.g. [—O—CH2-CH2-]$_n$ (n=1-9)), methyl linkers, ethyl linkers, propyl linkers, butyl linkers, or hexyl linkers. In some embodiments, such alkyl linkers may include peptides or amino acids.

In some embodiments, the non-nucleotidic linker may include, but are not limited to, those listed in Table 2.

TABLE 2

Representative Non-nucleotidic Linkers

Glycerol (1,2,3-Propanetriol)

1,1,1-Tris(hydroxymethyl)nitromethane 1,2,4-Butanetriol 1,1,1-Tris(hydroxymethyl)propane 2-(hydroxymethyl)-1,3-propanediol 1,2,6-Hexanetriol 2-(hydroxymethyl)1,4-butanediol 3-Methyl-1,3,5-pentanetriol 1,3,5-Pentanetriol 1,2,3-Heptanetriol TABLE 2-continued Representative Non-nucleotidic Linkers

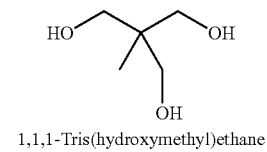
1,1,1-Tris(hydroxymethyl)ethane

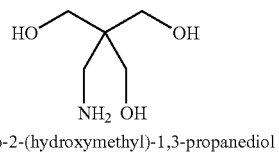
2-Amino-2-(hydroxymethyl)-1,3-propanediol

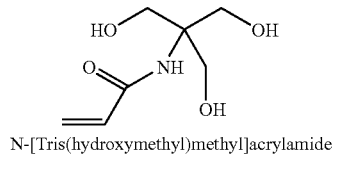
N-[Tris(hydroxymethyl)methyl]acrylamide

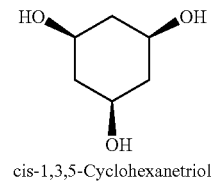
cis-1,3,5-Cyclohexanetriol

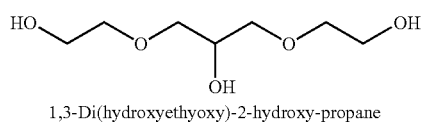
1,3-Di(hydroxyethyoxy)-2-hydroxy-propane

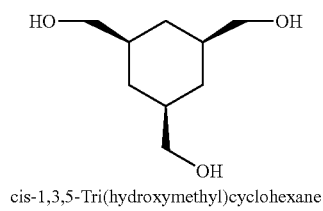
cis-1,3,5-Tri(hydroxymethyl)cyclohexane

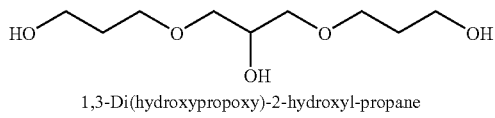
1,3-Di(hydroxypropoxy)-2-hydroxyl-propane

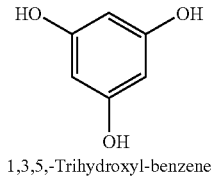
1,3,5,-Trihydroxyl-benzene

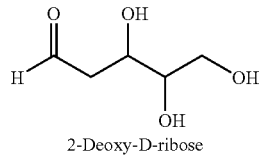
2-Deoxy-D-ribose

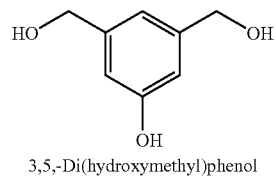
3,5,-Di(hydroxymethyl)phenol

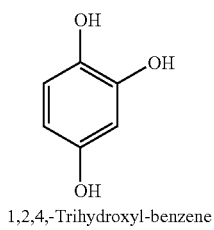
1,2,4,-Trihydroxyl-benzene

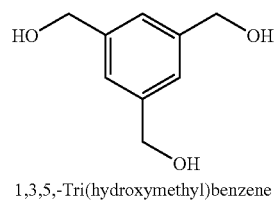
1,3,5,-Tri(hydroxymethyl)benzene

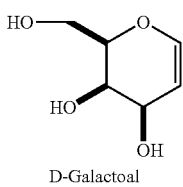
D-Galactoal

TABLE 2-continued
Representative Non-nucleotidic Linkers
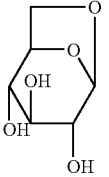
1,6-anhydro-β-D-Glucose
4,6-Nitropyrogallol
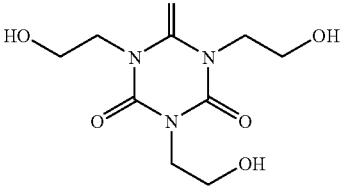
1,3,5-Tris(2-hydroxyethyl)-Cyanuric acid
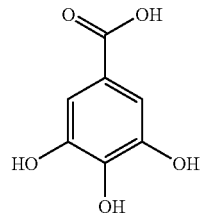
Gallic acid
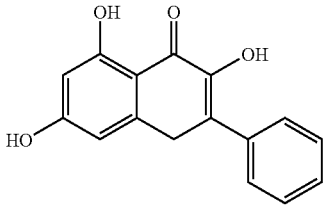
3,5,7-Trihydroxyflavone
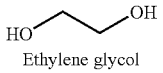
Ethylene glycol
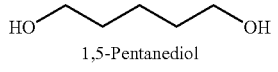
1,5-Pentanediol
1,3-Propanediol
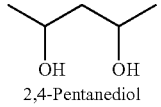
2,4-Pentanediol
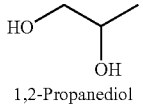
1,2-Propanediol
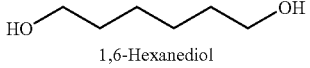
1,6-Hexanediol
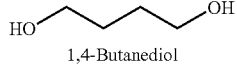
1,4-Butanediol
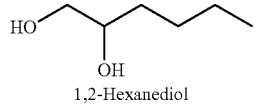
1,2-Hexanediol
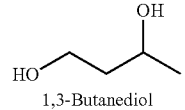
1,3-Butanediol
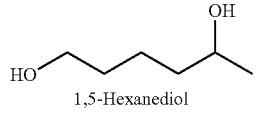
1,5-Hexanediol
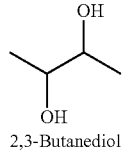
2,3-Butanediol
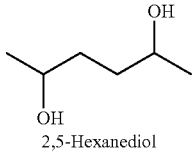
2,5-Hexanediol
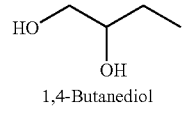
1,4-Butanediol TABLE 2-continued
Representative Non-nucleotidic Linkers
1,7-Heptanediol
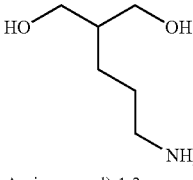
2-(1-Aminopropyl)-1,3-propanediol
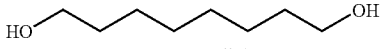
1,8-Octanediol
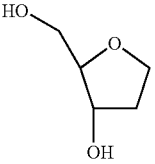
1,2-Dideoxyribose
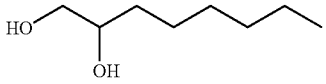
1,2-Octanediol
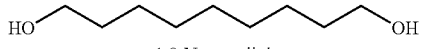
1,9-Nonanediol
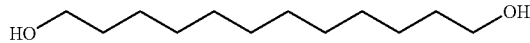
1,12-Dodecanediol
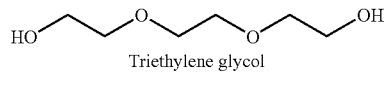
Triethylene glycol
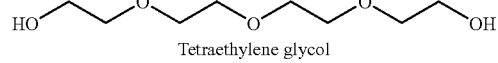
Tetraethylene glycol
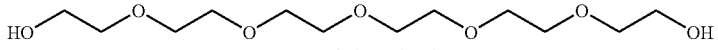
Hexaethylene glycol
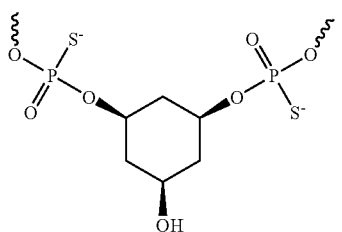
Cis, cis-cyclohexanetriol linker
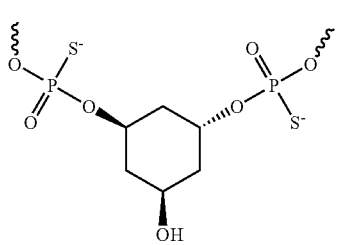
Cis, trans-cyclohexanetriol linker

TABLE 2-continued

Representative Non-nucleotidic Linkers

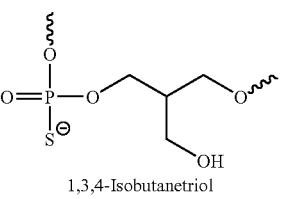
1,3,4-Isobutanetriol

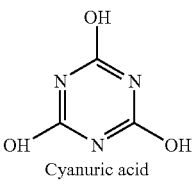
Cyanuric acid

In some embodiments, the small molecule linker is glycerol or a glycerol homolog of the formula HO—$(CH_2)_o$—CH(OH)—$(CH_2)_p$—OH, wherein o and p independently are integers from 1 to about 6, from 1 to about 4, or from 1 to about 3. In some other embodiments, the small molecule linker is a derivative of 1,3-diamino-2-hydroxypropane. Some such derivatives have the formula HO—$(CH_2)_m$—C(O)NH—$CH_2$—CH(OH)—$CH_2$—NHC(O)—$(CH_2)_m$—OH, wherein m is an integer from 0 to about 10, from 0 to about 6, from 2 to about 6, or from 2 to about 4.

Some non-nucleotidic linkers according to the invention permit attachment of more than two oligoribonucleotides, as depicted in Table 1. For example, the small molecule linker glycerol has three hydroxyl groups to which oligoribonucleotides may be covalently attached. Some immune modulatory oligoribonucleotides according to the invention, therefore, comprise more than two oligoribonucleotides (e.g., a Domain C and so on, the additional domains comprise oligoribonucleotides as defined above for Domains A, B, C, and D) linked at their 3' ends to a non-nucleotidic linker.

In a further embodiment of this aspect of the invention, a SIMRA may contain three or more oligoribonucleotides linked at their 3' or 5' ends, or through an internucleoside linkage or a functionalized nucleobase or sugar to two or more linkers, as depicted in Table 1. The oligoribonucleotides of this aspect of the invention may have the same or different sequences. The linkers of this aspect of the invention may be the same or different.

The immune modulatory oligoribonucleotides of the invention may conveniently be synthesized using an automated synthesizer and phosphoramidite approach. In some embodiments, the immune modulatory oligoribonucleotides are synthesized by a linear synthesis approach.

An alternative mode of synthesis is "parallel synthesis", in which synthesis proceeds outward from a central linker moiety (see FIG. 1). A solid support attached linker can be used for parallel synthesis, as is described in U.S. Pat. No. 5,912, 332. Alternatively, a universal solid support (such as phosphate attached controlled pore glass) support can be used.

Parallel synthesis of immune modulatory oligoribonucleotides has several advantages over linear synthesis: (1) parallel synthesis permits the incorporation of identical monomeric units; (2) unlike in linear synthesis, both (or all) the monomeric units are synthesized at the same time, thereby the number of synthetic steps and the time required for the synthesis is the same as that of a monomeric unit; and (3) the reduction in synthetic steps improves purity and yield of the final immune modulatory oligoribonucleotide product.

At the end of the synthesis by either linear synthesis or parallel synthesis protocols, the immune modulatory oligoribonucleotides may conveniently be deprotected with concentrated ammonia solution or as recommended by the phosphoramidite supplier, if a modified nucleoside is incorporated. The product immune modulatory oligoribonucleotide is preferably purified by reversed phase HPLC, detritylated, desalted and dialyzed.

Table 3 shows RNA-based immune modulatory oligoribonucleotides according to the invention. Unless otherwise specified, all nucleosides are ribonucleosides.

TABLE 3

Stabilized RNA-based Immune Modulatory Oligonucleotide (SIMRA) Sequences

| SIMRA# (SEQ ID NO.) | Sequences and Modification |
|---|---|
| 1 (1) | 5'-YUUCUG$_1$CUUCUG$_1$-X-G$_1$UCUUCG$_1$UCUUY-5' |
| 2 (2) | 5'-UG$_1$CUG$_1$CCUUUG$_1$-X-G$_1$UUUCCG$_1$UCG$_1$U-5' |
| 3 (3) | 5'-UG$_1$CUG$_1$CCUUUG$_1$-Z-G$_1$UUUCCG$_1$UCG$_1$U-5' |
| 4 (4) | 5'-G$_1$UCCUUUG$_1$CUG$_1$-X-G$_1$UCG$_1$UUUCCUG$_1$-5' |
| 5 (5) | 5'-L$_1$UGCUGCUUGUG-X-GUGUUCGUCGUL$_1$-5' |
| 6 (6) | 5'-LUGCUGCCUUUG-m-GUUUCCGUCGUL-5' |
| 7 (7) | 5'-G$_1$UCCUUG$_1$CUUG$_1$-M-G$_1$UUCG$_1$UUCCUG$_1$-5' |
| 8 (8) | 5'-UUCUG$_1$CUUCUG$_1$-M-G$_1$UCUUCG$_1$UCUU-5' |
| 9 (9) | 5'-G$_1$UCCUUUG$_1$CUG$_1$-m-G$_1$UCG$_1$UUUCCUG$_1$-5' |
| 10 (10) | 5'-YUUGACGUUGAC-m-CAGUUGCAGUUY-5' |

TABLE 3-continued

Stabilized RNA-based Immune Modulatory Oligonucleotide (SIMRA) Sequences

| SIMRA# (SEQ ID NO.) | Sequences and Modification |
|---|---|
| 11 (11) | 5'-YGUGCCUGAUGA-X-AGUAGUCCGUGY-5' |
| 12 (12) | 5'-AUGCUGCGCUG-M-GUCGCGUCGUA-5' |
| 13 (13) | 5'-UGCUGCUUG$_2$UG-X-GUG$_2$UUCGUCGU-5' |
| 14 (14) | 5'-UG$_2$CUGCUUGUG-X-GUGUUCGUCG$_2$U-5' |
| 15 (15) | 5'-UG$_2$CUG$_2$CUUG$_2$UG$_2$-X-G$_2$UG$_2$UUCG$_2$UCG$_2$U-5' |
| 16 (16) | 5'-UG$_2$CUG$_2$CUUG$_2$UG$_2$-m-G$_2$UG$_2$UUCG$_2$UCG$_2$U-5' |
| 17 (17) | 5'-UG$_2$CUG$_2$CUUG$_2$UG$_2$-M-G$_2$UG$_2$UUCG$_2$UCG$_2$U-5' |
| 18 (18) | 5'-UG$_2$CUG$_2$CCUUUG$_2$-M-G$_2$UUUCCG$_2$UCG$_2$U-5' |
| 19 (19) | 5'-UG$_2$CUG$_2$CCUUUG$_2$-m-G$_2$UUUCCG$_2$UCG$_2$U-5' |
| 20 (20) | 5'-UG$_2$CUG$_2$CCUUUG$_2$-X-G$_2$UUUCCG$_2$UCG$_2$U-5' |
| 21 (21) | 5'-UGC$_1$UGC$_1$UUGUG-X-GUGUUC$_1$GUC$_1$GU-5' |
| 22 (22) | 5'-UGC$_1$UGC$_1$UUGUG-m-GUGUUC$_1$GUC$_1$GU-5' |
| 23 (23) | 5'-UGC$_1$UGC$_1$UUGUG-M-GUGUUC$_1$GUC$_1$GU-5' |
| 24 (24) | 5'-UGC$_1$UGC$_1$UUC$_1$UG-X-GUC$_1$UUC$_1$GUC$_1$GU-5' |
| 25 (25) | 5'-UGC$_1$UGC$_1$C$_1$UUUG-M-GUUUC$_1$C$_1$GUC$_1$GU-5' |
| 26 (26) | 5'-UGC$_1$UGC$_1$C$_1$UUUG-m-GUUUC$_1$C$_1$GUC$_1$GU-5' |
| 27 (27) | 5'-UGC$_1$UGC$_1$C$_1$UUUG-X-GUUUC$_1$C$_1$GUC$_1$GU-5' |
| 28 (28) | 5'-UGCUGCU$_1$U$_1$CU$_1$G-X-GU$_1$CU$_1$U$_1$CGUCGU-5' |
| 29 (29) | 5'-YUGCUGCU$_1$U$_1$CU$_1$G-X-GU$_1$CU$_1$U$_1$CGUCGUY-5' |
| 30 (30) | 5'-UGUUGUGUGA$_1$C-X-CA$_1$GUGUGUUGU-5' |
| 31 (31) | 5'-UG$_2$CUG$_2$CUUG$_2$UG$_2$-m-G$_2$UG$_2$UUCG$_2$UCG$_2$U-5' |
| 32 (32) | 5'-UGC$_1$UGC$_1$UUGUG-m-GUGUUC$_1$GUC$_1$GU-5' |
| 33 (33) | 5'-UGC$_1$UGC$_1$C$_1$UUUG-X-GUUUC$_1$C$_1$GUC$_1$GU-5' |
| 34 (34) | 5'-GAUUGUGACGU-X-UGCAGUGUUAG-5' |
| 35 (35) | 5'-CUGAAGCUUGU-X-UGUUCGAAGUC-5' |
| 36 (36) | 5'-UG$_2$CUG$_2$CUUG$_2$UG$_2$-M-G$_2$UG$_2$UUCG$_2$UCG$_2$U-5' |
| 37 (37) | 5'-YUGCUGCUUGUG-X-GUGUUCGUCGUY-5' |
| 38 (38) | 5'-UG$_1$CUG$_1$CUUCUG$_1$-X-G$_1$UCUUCG$_1$UCG$_1$U-5' |
| 39 (39) | 5'-UG$_3$CUG$_3$CUUCUG$_3$-X-G$_3$UCUUCG$_3$UCG$_3$U-5' |
| 40 (40) | 5'-UG$_3$CUG$_3$CCUUUG$_3$-m-G$_3$UUUCCG$_3$UCG$_3$U-5' |
| 41 (41) | 5'-YUGACGAUGAGU-X-UGAGUAGCAGUY-5' |
| 42 (42) | 5'-UGCUGCU$_1$U$_1$CU$_1$G-X-GU$_1$CU$_1$U$_1$CGUCGU-5' |
| 43 (43) | 5'-UGC$_1$UGC$_1$C$_1$UUUG-m-GUUUC$_1$C$_1$GUC$_1$GU-5' |
| 44 (44) | 5'-UG$_1$CUG$_1$CUUCUG$_1$-6Eg-M-6Eg-G$_1$UCUUCG$_1$UCG$_1$U-5' |
| 45 (45) | 5'-YUGACGACGCUU-X-UUCGCAGCAGUY-5' |
| 46 (46) | 5'-YUGACGACUGCU-X-UCGUCAGCAGUY-5' |

TABLE 3-continued

Stabilized RNA-based Immune Modulatory Oligonucleotide (SIMRA) Sequences

| SIMRA# (SEQ ID NO.) | Sequences and Modification |
|---|---|
| 47 (47) | 5'-YUGACGACUUGC-X-CGUUCAGCAGUY-5' |
| 48 (48) | 5'-YUGCGCGAACUU-$X_3$-UUCAAGCGCGUY-5' |
| 49 (49) | 5'-AG$_1$UG$_1$UUUUCUG$_1$-X-G$_1$UCUUUUG$_1$UG$_1$A-5' |
| 50 (50) | 5'-UG$_1$CUG$_1$CUUUUG$_1$-X-G$_1$UUUUCG$_1$UCG$_1$U-5' |
| 51 (51) | 5'-UG$_1$UUG$_1$UUUG$_1$UG$_1$-X-G$_1$UG$_1$UUUG$_1$UUG$_1$U-5' |
| 52 (52) | 5'-UG$_1$AUG$_1$AAG$_1$CUU-X-UUCG$_1$AAG$_1$UAG$_1$U-5' |
| 53 (53) | 5'-YUGCUGCUUGAA-X-AAGUUCGUCGUY-5' |
| 54 (54) | 5'-YUUGACUGAUGA-X-AGUAGUCAGUUY-5' |
| 55 (55) | 5'-UGCUGCUUUUG-X-GUUUUCGUCGU-5' |
| 56 (56) | 5'-UGUUGUUUGUG-X-GUGUUUGUUGU-5' |
| 57 (57) | 5'-UGUUCGAACAC-X-CACAAGCUUGU-5' |
| 58 (58) | 5'-UUGACGUUGAC-X-CAGUUGCAGUU-5' |
| 59 (59) | 5'-UUGACGUUGAC-Z-CAGUUGCAGUU-5' |
| 60 (60) | 5'-UUGACGUUGAC-M-CAGUUGCAGUU-5' |
| 61 (61) | 5'-UUGACGUUGAC-m-CAGUUGCAGUU-5' |
| 62 (62) | 5'-GUGCCUGAUGA-X-AGUAGUCCGUG-5' |
| 63 (63) | 5'-CCGAUGCCGAC-X-CAGCCGUAGCC-5' |
| 64 (64) | 5'-CCGAUGCAUCG-X-GCUACGUAGCC-5' |
| 65 (65) | 5'-GUGCCUGAUGA-Z-AGUAGUCCGUG-5' |
| 66 (66) | 5'-GUGCCUGAUGA-M-AGUAGUCCGUG-5' |
| 67 (67) | 5'-GUGCCUGAUGA-m-AGUAGUCCGUG-5' |
| 68 (68) | 5'-CCGAUGCCGAC-Z-CAGCCGUAGCC-5' |
| 69 (69) | 5'-CCGAUGCCGAC-M-CAGCCGUAGCC-5' |
| 70 (70) | 5'-CCGAUGCCGAC-m-CAGCCGUAGCC-5' |
| 71 (71) | 5'-CCGAUGCAUCG-Z-GCUACGUAGCC-5' |
| 72 (72) | 5'-CCGAUGCAUCG-M-GCUACGUAGCC-5' |
| 73 (73) | 5'-CCGAUGCAUCG-m-GCUACGUAGCC-5' |
| 74 (74) | 5'-AGCACAACUGU-X-UGUCAACACGA-5' |
| 75 (75) | 5'-AAAAAAAAAA-X-AAAAAAAAAA-5' |
| 76 (76) | 5'-YCACUGUUGAGA-X-AGAGUUGUCACY-5' |
| 77 (77) | 5'-YAACUGUUGACC-X-CCAGUUGUCAAY-5' |
| 78 (78) | 5'-YCAACGACCUGU-X-UGUCCAGCAACY-5' |
| 79 (79) | 5'-CACUG$_1$UUG$_1$AG$_1$A-X-AG$_1$AG$_1$UUG$_1$UCAC-5' |
| 80 (80) | 5'-AACUG$_1$UUG$_1$ACC-X-CCAG$_1$UUG$_1$UCAA-5' |
| 81 (81) | 5'-CAACG$_1$ACCUG$_1$U-X-UG$_1$UCCAG$_1$CAAC-5' |
| 82 (82) | 5'-AUGCUGCGCUG-X-GUCGCGUCGUA-5' |
| 83 (83) | 5'-AUGCUGCGCUG-Z-GUCGCGUCGUA-5' |

TABLE 3-continued

Stabilized RNA-based Immune Modulatory Oligonucleotide (SIMRA) Sequences

| SIMRA# (SEQ ID NO.) | Sequences and Modification |
|---|---|
| 84 (84) | 5'-AUGCUGCGCUG-m-GUCGCGUCGUA-5' |
| 85 (85) | 5'-AACUGUUGACC-X-CCAGUUGUCAA-5' |
| 86 (86) | 5'-CACUGUUGAGA-X-AGAGUUGUCAC-5' |
| 87 (87) | 5'-GCACACUUGUU-X-UUGUUCACACG-5' |
| 88 (88) | 5'-UGUUGUGUGAC-X-CAGUGUGUUGU-5' |
| 89 (89) | 5'-CCGAUGCAUCG-X-GCUACGUAGCC-5' |
| 90 (90) | 5'-AACGAACCGAC-X-CAGCCAAGCAA-5' |
| 91 (91) | 5'-YCAACGACCUGU-X-UGUCCAGCAACY-5' |
| 92 (92) | 5'-LCAACGACCUGU-X-UGUCCAGCAACL-5' |
| 93 (93) | 5'-CGUUGUGAUGA-X-AGUAGUGUUGC-5' |
| 94 (94) | 5'-ACGAUUGUGAC-X-CAGUGUUAGCA-5' |
| 95 (95) | 5'-ACUUUGACGAU-X-UAGCAGUUUCA-5' |
| 96 (96) | 5'-CGAUGCGAUGA-X-AGUAGCGUAGC-5' |
| 97 (97) | 5'-ACGUCUGACGA-X-AGCAGUCUGCA-5' |
| 98 (98) | 5'-AACUGCUGGAU-X-UAGGUCGUCAA-5' |
| 99 (99) | 5'-UUGGACUCCAG-X-GACCUCAGGUU-5' |
| 100 (100) | 5'-UCGACUUCCAG-X-GACCUUCAGCU-5' |
| 101 (101) | 5'-CCGACUUGGAC-X-CAGGUUCAGCC-5' |
| 102 (102) | 5'-AAGACUGAACU-X-UCAAGUCAGAA-5' |
| 103 (103) | 5'-YUG$_2$CUG$_2$CCUUUG$_2$-X-G$_2$UUUCCG$_2$UCG$_2$UY-5' |
| 104 (104) | 5'-YUG$_2$CUG$_2$CCUUUG$_2$-M-G$_2$UUUCCG$_2$UCG$_2$UY-5' |
| 105 (105) | 5'-YUG$_2$CUG$_2$CCUUUG$_2$-m-G$_2$UUUCCG$_2$UCG$_2$UY-5' |
| 106 (106) | 5'-LUG$_2$CUG$_2$CCUUUG$_2$-X-G$_2$UUUCCG$_2$UCG$_2$UL-5' |
| 107 (107) | 5'-LUG$_2$CUG$_2$CCUUUG$_2$-M-G$_2$UUUCCG$_2$UCG$_2$UL-5' |
| 108 (107) | 5'-LUG$_2$CUG$_2$CCUUUG$_2$-m-G$_2$UUUCCG$_2$UCG$_2$UL-5' |
| 109 (109) | 5'-L$_1$UG$_2$CUG$_2$CCUUUG$_2$-X-G$_2$UUUCCG$_2$UCG$_2$UL$_1$-5' |
| 110 (110) | 5'-L$_1$UG$_2$CUG$_2$CCUUUG$_2$-M-G$_2$UUUCCG$_2$UCG$_2$UL$_1$-5' |
| 111 (111) | 5'-L$_1$UG$_2$CUG$_2$CCUUUG$_2$-m-G$_2$UUUCCG$_2$UCG$_2$UL$_1$-5' |
| 112 (112) | 5'-G$_1$UCCUUG$_1$CUUG$_1$-m-G$_1$UUCG$_1$UUCCUG$_1$-5' |
| 113 (113) | 5'-UUCUG$_1$CUUCUG$_1$-m-G$_1$UCUUCG$_1$UCUU-5' |
| 114 (114) | 5'-UG$_1$CUG$_1$CCUUUG$_1$-M-G$_1$UUUCCG$_1$UCG$_1$U-5' |
| 115 (115) | 5'-UG$_1$CCUUUG$_1$CUG$_1$-M-G$_1$UCG$_1$UUUCCG$_1$U-5' |
| 116 (116) | 5'-UG$_1$CUG$_1$CUUCUG$_1$-M-G$_1$UCUUCG$_1$UCG$_1$U-5' |
| 117 (117) | 5'-UG$_1$C$_1$UG$_1$C$_1$C$_1$UUUG$_1$-X-G$_1$UUUC$_1$C$_1$G$_1$UC1G1U-5' |
| 118 (118) | 5'-UG$_1$C$_1$UG$_1$C$_1$UUC$_1$UG$_1$-X-G$_1$UC$_1$UUC$_1$G$_1$UC1G1U-5' |
| 119 (119) | 5'-YUGCUGCUUCUG-6Eg-M-6Eg-GUCUUCGUCGUY-5' |

TABLE 3-continued

Stabilized RNA-based Immune Modulatory Oligonucleotide (SIMRA) Sequences

| SIMRA# (SEQ ID NO.) | Sequences and Modification |
|---|---|
| 120 (120) | 5'-UGGCUUGACGC-X-CGCAGUUCGGU-5' |
| 121 (121) | 5'-UGCUGCUUGAA-X-AAGUUCGUCGU-5' |
| 122 (122) | 5'-UGACGAUGAGU-X-UGAGUAGCAGU-5' |
| 123 (123) | 5'-UGAUGAGGACU-X-UCAGGAGUAGU-5' |
| 124 (124) | 5'-UGUUGAGGAAC-X-CAAGGAGUUGU-5' |
| 125 (125) | 5'-UGCGAGACUGC-X-CGUCAGAGCGU-5' |
| 126 (126) | 5'-GUUGAACGACU-X-UCAGCAAGUUG-5' |
| 127 (127) | 5'-UGACUGAUGAC-X-CAGUAGUCAGU-5' |
| 128 (128) | 5'-UGUUGAACGAC-X-CAGCAAGUUGU-5' |
| 129 (129) | 5'-UGAGCGUGAAC-X-CAAGUGCGAGU-5' |
| 130 (130) | 5'-UG$_1$G$_1$CUUG$_1$ACG$_1$C-X-CG$_1$CAG$_1$UUCG$_1$G$_1$U-5' |
| 131 (131) | 5'-UG$_1$ACG$_1$AUG$_1$AG$_1$U-X-UG$_1$AG$_1$UAG$_1$CAG$_1$U-5' |
| 132 (132) | 5'-UG$_1$UUG$_1$AG$_1$G$_1$AAC-X-CAAG$_1$G$_1$AG$_1$UUG$_1$U-5' |
| 133 (133) | 5'-UG$_1$UUG$_1$AACG$_1$AC-X-CAG$_1$CAAG$_1$UUG$_1$U-5' |
| 134 (134) | 5'-YUGCGAGACUGC-X-CGUCAGAGCGUY-5' |
| 135 (135) | 5'-YUGAGCGUGAAC-X-CAAGUGCGAGUY-5' |
| 136 (136) | 5'-YUUGAGCUGGAC-X-CAGGUCGAGUUY-5' |
| 137 (137) | 5'-YGUUGAGGAACU-X-UCAAGGAGUUGY-5' |
| 138 (138) | 5'-YUGAUGAAGCUU-X-UUCGAAGUAGUY-5' |
| 139 (139) | 5'-YUUGACGAUGAG-X-GAGUAGCAGUUY-5' |
| 140 (140) | 5'-YUUGUUGAACGA-X-AGCAAGUUGUUY-5' |
| 141 (141) | 5'-YUUGAACGACUU-X-UUCAGCAAGUUY-5' |
| 142 (142) | 5'-YUGAUGGAACGA-X-AGCAAGGUAGUY-5' |
| 143 (143) | 5'-UG$_1$CUG$_1$CCUUUG$_1$-M-G$_1$UUUCCG$_1$UCG$_1$U-5' |
| 144 (144) | 5'-UG$_1$CUG$_1$CCUUUG$_1$-Y-M-Y-G$_1$UUUCCG$_1$UCG$_1$U-5' |
| 145 (145) | 5'-UG$_1$CUG$_1$CCUUUG$_1$-3Eg-M-3Eg-G$_1$UUUCCG$_1$UCG$_1$U-5' |
| 146 (146) | 5'-UG$_1$CUG$_1$CCUUUG$_1$-4Eg-M-4Eg-G$_1$UUUCCG$_1$UCG$_1$U-5' |
| 147 (147) | 5'-UG$_1$CUG$_1$CCUUUG$_1$-6Eg-M-6Eg-G$_1$UUUCCG$_1$UCG$_1$U-5' |
| 148 (148) | 5'-YUGCUGCUUGUG-Y-M-Y-GUGUUCGUCGUY-5' |
| 149 (149) | 5'-YUGCUGCUUGUG-3Eg-M-3Eg-GUGUUCGUCGUY-5' |
| 150 (150) | 5'-YUGCUGCUUGUG-4Eg-M-4Eg-GUGUUCGUCGUY-5' |
| 151 (151) | 5'-CAACGAACCCU-X-UCCCAAGCAAC-5' |
| 152 (152) | 5'-UGCUGCUGCUG-X-GUCGUCGUCGU-5' |
| 153 (153) | 5'-UGAAGCUUGAA-X-AAGUUCGAAGU-5' |
| 154 (154) | 5'-UGAACGUGAAC-X-CAAGUGCAAGU-5' |
| 155 (155) | 5'-YUGC$_4$UGC$_4$UUGUG-X-GUGUUC$_4$GUC$_4$GUY-5' |
| 156 (156) | 5'-UG$_1$C$_4$UG$_1$C$_4$UUC$_4$UG$_1$-X-G$_1$UC$_4$UUC$_4$G$_1$UC$_4$G$_1$U-5' |

TABLE 3-continued

Stabilized RNA-based Immune Modulatory Oligonucleotide (SIMRA) Sequences

| SIMRA# (SEQ ID NO.) | Sequences and Modification |
|---|---|
| 157 (157) | 5'-YUG$_1$ACG$_1$AUG$_1$AG$_1$U-X-UG$_1$AG$_1$UAG$_1$CAG$_1$UY-5' |
| 158 (158) | 5'-G$_1$UCCUUG$_1$CUUG$_1$-X$_1$-G$_1$UUCG$_1$UUCCUG$_1$-5' |
| 159 (159) | 5'-UUCUG$_1$CUUCUG$_1$-X$_1$-G$_1$UCUUCG$_1$UCUU-5' |
| 160 (160) | 5'-UG$_1$CCUUUG$_1$CUG$_1$-X$_2$-G$_1$UCG$_1$UUUCCG$_1$U-5' |
| 161 (161) | 5'-UG$_1$CUG$_1$CUUCUG$_1$-X$_2$-G$_1$UCUUCG$_1$UCG$_1$U-5' |
| 162 (162) | 5'-PUUCUG$_1$CUUCUG$_1$-m-G$_1$UCUUCG$_1$UCUUP-5' |
| 163 (163) | 5'-PUG$_1$CCUUUG$_1$CUG$_1$-M-G$_1$UCG$_1$UUUCCG$_1$UP-5' |
| 164 (164) | 5'-UG$_1$CUG$_1$CUUC$_1$UG$_1$-X$_1$-G$_1$UC$_1$UUCG$_1$UCG$_1$U-5' |
| 165 (165) | 5'-UG$_1$CUG$_1$CUUC$_1$UG$_1$-X$_3$-G$_1$UC$_1$UUCG$_1$UCG$_1$U-5' |
| 166 (166) | 5'-C$_2$UGAAGC$_2$UUGU-X-UGUUC$_2$GAAGUC$_2$-5' |
| 167 (167) | 5'-CU$_2$GAAGCU$_2$U$_2$GU$_2$-X-U$_2$GU$_2$U$_2$CGAAGU$_2$C-5' |
| 168 (168) | 5'-YAACUG$_2$UUG$_2$ACC-X-CCAG$_2$UUG$_2$UCAAY-5' |
| 169 (169) | 5'-L$_1$UG$_2$G$_2$CUUG$_2$ACG$_2$C-X-CG$_2$CAG$_2$UUCG$_2$G$_2$UL$_1$-5' |
| 170 (170) | 5'-YUGACGCUGACU-X-UCAGUCGCAGUY-5' |
| 171 (171) | 5'-YUGACUGCGACU-X-UCAGCGUCAGUY-5' |
| 172 (172) | 5'-YUGCGAACGCUU-X-UUCGCAAGCGUY-5' |
| 173 (173) | 5'-YUGCGACUGACU-X$_3$-UCAGUCAGCGUY-5' |
| 174 (174) | 5'-YUGCGCUGAACU-X$_3$-UCAAGUCGCGUY-5' |
| 175 (175) | 5'-YUGCUGACGACU-X$_3$-UCAGCAGUCGUY-5' |
| 176 (176) | 5'-YUGCUUGAACGC-X$_3$-CGCAAGUUCGUY-5' |
| 177 (177) | 5'-YUUGCUGAACGC-X$_3$-CGCAAGUCGUUY-5' |
| 178 (178) | 5'-UG$_1$CUG$_1$CCUUUG$_1$-Y-X-Y-G$_1$UUCCG$_1$UCG$_1$U-5' |
| 179 (179) | 5'-YUGUUGUGUGAC-X-CAGUGUGUUGUY-5' |
| 180 (180) | 5'-YUGCUGCCUUUG-X-GUUUCCGUCGUY-5' |
| 181 (181) | 5'-YUGCUGCUGCUG-X-GUCGUCGUCGUY-5' |
| 182 (182) | 5'-YUGUUGUGUGAC-Z-CAGUGUGUUGUY-5' |
| 183 (183) | 5'-EUUGAACGACUU-X-UUCAGCAAGUUE-5' |
| 184 (184) | 5'-EUGUUGUGUGAC-X-CAGUGUGUUGUE-5' |
| 185 (185) | 5'-EUGCUGCCUUUG-X-GUUUCCGUCGUE-5' |
| 186 (186) | 5'-EUGCUGCUGCUG-X-GUCGUCGUCGUE-5' |
| 187 (187) | 5'-U$_1$GCUGCUUGUG-X-GUGUUCGUCGU$_1$-5' |
| 188 (188) | 5'-U$_1$GCU$_1$GCUUGUG-X-GUGUUCGU$_1$CGU$_1$-5' |
| 189 (189) | 5'-U$_1$GCU$_1$GCU$_1$U$_1$GU$_1$G-X-GU$_1$GU$_1$U$_1$CGU$_1$CGU$_1$-5' |

In a second aspect, the invention provides pharmaceutical formulations comprising a SIMRA compound according to the invention and a pharmaceutically acceptable carrier.

In a third aspect, the invention provides methods for generating TLR7 and/or TLR8 mediated immune responses in a vertebrate, such methods comprising administering to the vertebrate a SIMRA compound according to the invention. In some embodiments, the vertebrate is a mammal. In preferred embodiments, SIMRA compound is administered to a vertebrate in need of immune modulation.

In a fourth aspect, the invention provides methods for therapeutically treating a patient having a disease or disorder, such methods comprising administering to the patient a SIMRA compound according to the invention. In various embodiments, the disease or disorder to be treated is one in which an immune modulation may be desirable. For example, but not limited to, cancer, an autoimmune disorder, infectious disease, airway inflammation, inflammatory disorders, allergy, asthma, or a disease caused by a pathogen. Pathogens include bacteria, parasites, fungi, viruses, viroids and prions.

In a fifth aspect, the invention provides methods for preventing a disease or disorder, such methods comprising administering to the patient SIMRA compound according to the invention. In various embodiments, the disease or disorder to be prevented is one in which an immune modulation may be desirable. For example, but not limited to, cancer, an autoimmune disorder, airway inflammation, inflammatory disorders, infectious disease, allergy, asthma, or a disease caused by a pathogen. Pathogens include bacteria, parasites, fungi, viruses, viroids, and prions.

In a sixth aspect the invention provides a method of preventing or treating a disorder, such methods comprises isolating cells capable of producing cytokines or chemokines including, but not limited to, immune cells, B cells, T-regulatory cells, B-cells, PBMCs, pDCs and lymphoid cells; culturing such cells under standard cell culture conditions, treating such cells ex vivo with a SIMRA such that the isolated cells produce or secrete increased levels of cytokines or chemokines, and administering or re-administering the treated cells to a patient in need of cytokine or chemokine therapy for the prevention or treatment of disease. This aspect of the invention would be in accordance with standard adoptive cellular immunotherapy techniques to produce activated immune cells.

In some embodiments of this aspect of the invention, the cells capable of producing cytokines or chemokines may be isolated from subjects with or without a disease or disorder. Such isolation may include identification and selection and could be performed using standard cell isolation procedures, including those set forth in the specific examples below. Such isolated cells are cultured according to standard cell culturing procedures and using standard cell culture conditions, which may include the culturing procedures and conditions set forth in the specific examples below. In a further aspect of this embodiment of the invention, the isolated cells are cultured in the presence of at least one SIMRA, in an amount and for a time period sufficient to induce, increase or enhance the production and/or secretion of cytokines and/or chemokines as compared to the isolated cells cultured in the absence of such one or more SIMRA. Such time may be from minutes, to hours, to days. Such isolated, SIMRA-treated cells may find use following re-administration to the donor or administration to a second histologically compatible patient, wherein such donor or second patient are in need of induced, increased or enhanced production and/or secretion of cytokines and/or chemokines. For example, re-administration to a donor or administration to a second patient having cancer, an autoimmune disorder, airway inflammation, inflammatory disorders, infectious disease, allergy, asthma, or a disease caused by a pathogen. Such re-administration or administration may be accomplished using various modes, including catheter or injection administration or any other effective route. This aspect of the invention may also find use in patients who may have a limited or incomplete ability to mount an immune response or are immune compromised (e.g. patient infected with HIV and bone marrow transplant patients). This aspect of the invention may also find use in combination with SIMRA administration to the patient administered or re-administered the isolated, SIMRA-treated cells.

In any of the methods according to the invention, the SIMRA compound can variously act by producing direct immune modulatory effects alone or in combination with any other agent useful for treating or preventing the disease or condition that does not diminish the immune modulatory effect of the SIMRA compound. In any of the methods according to the invention, the agent(s) useful for treating or preventing the disease or condition includes, but is not limited to, vaccines, antigens, antibodies, preferably monoclonal antibodies, cytotoxic agents, allergens, antibiotics, siRNA, microRNA, antisense oligonucleotides, TLR agonist (e.g. agonists of TLR9 and/or agonists of TLR7 and/or agonists of TLR8), chemotherapeutic agents (both traditional chemotherapy and modern targeted therapies), targeted therapeutic agents, activated cells, peptides, proteins, gene therapy vectors, peptide vaccines, protein vaccines, DNA vaccines, adjuvants, and co-stimulatory molecules (e.g. cytokines, chemokines, protein ligands, trans-activating factors, peptides or peptides comprising modified amino acids), or combinations thereof. For example, in the treatment of cancer, it is contemplated that the SIMRA compound may be administered in combination with one or more chemotherapeutic compound, targeted therapeutic agent and/or monoclonal antibody. Alternatively, the agent can include DNA vectors encoding for antigen or allergen. Alternatively, the SIMRA compounds can be administered in combination with other adjuvants to enhance the specificity or magnitude of the immune response to the SIMRA compound.

In any of the methods according to the invention, administration of SIMRA compound, alone or in combination with any other agent, can be by any suitable route, including, without limitation, parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form. Administration of the therapeutic compositions of SIMRA compound can be carried out using known procedures using a pharmaceutically effective amount and for periods of time effective to reduce symptoms or surrogate markers of the disease. For example, a pharmaceutically effective amount of a SIMRA compound for treating a disease and/or disorder could be that amount necessary to alleviate or reduce the symptoms, or delay or ameliorate a tumor, cancer, or bacterial, viral or fungal infection. A pharmaceutically effective amount for use as a vaccine adjuvant could be that amount useful for boosting a subject's immune response to a vaccine or antigen. In the context of administering a composition that modulates an immune response to a co-administered antigen, a pharmaceutically effective amount of a SIMRA compound and antigen is an amount sufficient to achieve the desired modulation as compared to the immune response obtained when the antigen is administered alone. The effective amount for any particular application can vary depending on such factors as the disease or condition being treated, the particular oligonucleotide being administered, the size of the subject, or the severity of the disease or condition. One of ordinary skill in the art can empirically determine the pharmaceutically effective amount of a particular oligonucleotide without necessitating undue experimentation.

When administered systemically, the therapeutic composition is preferably administered at a sufficient dosage to attain a blood level of SIMRA compound from about 0.0001 micromolar to about 10 micromolar. For localized administration, much lower concentrations than this may be effective, and much higher concentrations may be tolerated. Preferably, a total dosage of SIMRA compound ranges from about 0.001 mg per patient per day to about 200 mg per kg body weight per day. It may be desirable to administer simultaneously, or sequentially a therapeutically effective amount of one or more of the therapeutic compositions of the invention to an individual as a single treatment episode.

The SIMRA compound may optionally be linked to one or more allergens and/or antigens (self or foreign), an immunogenic protein or peptide, such as keyhole limpet hemocyanin (KLH), cholera toxin B subunit, or any other immunogenic carrier protein. SIMRA can also be used in combination with other compounds (e.g. adjuvants) including, without limitation, TLR agonists (e.g. TLR2 agonists and TLR9 agonists), Freund's incomplete adjuvant, KLH, monophosphoryl lipid A (MPL), alum, and saponins, including QS-21 and imiquimod, or combinations thereof.

The methods according to this aspect of the invention are useful for model studies of the immune system. The methods are also useful for the prophylactic or therapeutic treatment of human or animal disease. For example, the methods are useful for pediatric and veterinary vaccine applications.

The examples below are intended to further illustrate certain exemplar embodiments of the invention, and are not intended to limit the scope of the invention.

EXAMPLES

Example 1

Immune Modulatory Oligoribonucleotide Synthesis

The immune modulatory oligoribonucleotides were chemically synthesized using phosphoramidite chemistry on automated DNA/RNA synthesizer. N-acetyl protected (Except U) 2'-O-TBDMS RNA monomers, A, G, C and U, were purchased from Sigma-Aldrich. 7-deaza-G, inosine was purchased from ChemGenes Corporation. 0.25M 5-ethylthio-1H-tetrazole, PAC-anhydride Cap A and Cap B were purchased from Glen Research. 3% trichloroacetic acid (TCA) in dichloromethane (DCM) and 5% 3H-1,2-Benzodithiole-3-one-1,1-dioxide (Beaucage reagent) were made in house.

Immune modulatory oligoribonucleotides were synthesized at 1-2 µM scale using a standard RNA synthesis protocol.

Cleavage and Base Deprotection

Immune modulatory oligoribonucleotides were cleaved from solid support and the protecting groups of exo-cyclic-amines were removed in methylamine and ammonium hydroxide solution. The resulting solution was dried completely in a SpeedVac.

IE HPLC Purification

Immune modulatory oligoribonucleotides were purified by ion exchange HPLC. Using Dionex DNAPac 100 column. Crude immune modulatory oligoribonucleotide solution was injected into HPLC. Above gradient is performed and the fractions were collected. All fractions containing more than 90% desired product were mixed, and then the solution was concentrated to almost dry by RotoVap. RNAse-free water was added to make final volume of 10 ml.

C-18 Reversed Phase Desalting tC-18 Sep-Pak cartridge purchased from Waters was washed by passing with 10 ml of acetonitrile followed by 10 ml of 0.5 M sodium acetate through the cartridge. Then 10 ml of immune modulatory oligoribonucleotide solution was loaded on to the cartridge. Then 15 ml of water was used to wash out the salt. The immune modulatory oligoribonucleotide was finally eluted using 1 ml of 50% acetonitrile in water. The solution was placed in SpeedVac for 30 minutes. The remaining solution was filtered through a 0.2 micron filter and then was lyophilized. The solid was then re-dissolved in RNAse free water to make the desired concentration. The final solution was stored below 0° C. Oligoribonucleotides were analyzed for purity by Capillary Electrophoresis, Ion Exchange HPLC and PAGE analysis, and for molecular mass by MALDI-ToF mass spectrometry.

Example 2

Protocols for Assays with HEK293 Cells Expressing TLRs

HEK293 or HEK293XL/human TLR7 or HEK293 or HEK293XL/human TLR8 cells (Invivogen, San Diego, Calif.) were cultured in 48-well plates in 250 µl/well DMEM supplemented with 10% heat-inactivated FBS in a 5% $CO_2$ incubator.

Reporter Gene Transformation

HEK293 or HEK293XL cells stably expressing human TLR7 or TLR8 (Invivogen, San Diego, Calif.) were cultured in 48-well plates in 250 µl/well DMEM supplemented with 10% heat-inactivated FBS in a 5% $CO_2$ incubator. At 80% confluence, cultures were transiently transfected with 400 ng/ml of SEAP (secreted form of human embryonic alkaline phosphatase) reporter plasmid (pNifty2-Seap) (Invivogen) in the presence of 4 µl/ml of lipofectamine (Invitrogen, Carlsbad, Calif.) in culture medium. Plasmid DNA and lipofectamine were diluted separately in serum-free medium and incubated at room temperature for 5 minutes. After incubation, the diluted DNA and lipofectamine were mixed and the mixtures were incubated at room temperature for 20 minutes. Aliquots of 25 µl of the DNA/lipofectamine mixture containing 100 ng of plasmid DNA and 1 µl of lipofectamine were added to each well of the cell culture plate, and the cultures were continued for 4 hours.

IMO-Treatment

After transfection, medium was replaced with fresh culture medium. The HEK293 or HEK29XL cells expressing human TLR7 or TLR8 were stimulated with 0, 20, 50, 100, 150, 200, or 300 µg/ml of agonists of TLR7 or TLR8, SIMRAs, and the cultures were continued for 18 hours-20 hours. At the end of SIMRA treatment, 30 µl of culture supernatant was taken from each treatment and used for SEAP assay following manufacturer's protocol (Invivogen).

SEAP (Secreted Form of Human Embryonic Alkaline Phosphatase) Assay

Briefly, culture supernatants were incubated with p-nitrophynyl phosphate substrate and the yellow color generated was measured by a plate reader at 405 nm. The data are shown as fold increase in NF-κB activity over PBS control. (Putta M R et al, Nucleic Acids Res., 2006, 34:3231-8).

Example 3

Human Cell Culture Protocols

Human PBMC Isolation

Peripheral blood mononuclear cells (PBMCs) from freshly drawn, healthy volunteer blood (CBR Laboratories, Boston, Mass.) were isolated by Ficoll density gradient centrifugation method (Histopaque-1077, Sigma).

Human pDC Isolation

Peripheral blood mononuclear cells (PBMCs) from freshly drawn healthy volunteer blood (CBR Laboratories, Boston, Mass.) were isolated by Ficoll density gradient centrifugation method (Histopaque-1077, Sigma). pDCs were isolated from PBMCs by positive selection using the BDCA4 cell isolation kits (Miltenyi Biotec) according to the manufacturer's instructions.

Human mDC Isolation

Peripheral blood mononuclear cells (PBMCs) from freshly drawn healthy volunteer blood (CBR Laboratories, Boston, Mass.) were isolated by Ficoll density gradient centrifugation method (Histopaque-1077, Sigma). Myeloid dendritic cells (mDCs) were isolated from PBMCs by positive selection using the BDCA4 cell isolation kits (Miltenyi Biotec) according to the manufacturer's instructions.

Multiplex Cytokine Assays

Human PBMCs were plated in 48-well plates using $5 \times 10^6$ cells/ml. pDCs were plated in 96-well dishes using $1 \times 10^6$ cells/ml. The SIMRAs dissolved in DPBS (pH 7.4; Mediatech) were added to a final concentration of 20, 50, 100, 200 or 300 μg/ml or as indicated in the figures to the cell cultures. The cells were then incubated at 37° C. for 24 hr and the supernatants were collected for luminex multiplex or ELISA assays. The experiments were performed in triplicate wells. The levels of IFN-α, IL-6, or TNF-α were measured by sandwich ELISA. The required reagents, including cytokine antibodies and standards, were purchased from PharMingen.

Luminex multiplex assays were performed using Biosource human multiplex cytokine assay kits on Luminex 100/200 instrument and the data were analyzed using StarStation software supplied by Applied Cytometry Systems (Sacramento, Calif.).

Example 4

In Vivo Cytokine Secretion in Mouse Model Treated with TLR7/8 Agonist Compounds

C57BL/6 mice and BALB/c mice, 5-6 weeks old, were obtained from Taconic Farms, Germantown, N.Y. and maintained in accordance with Idera Pharmaceutical's IACUC approved animal protocols. Mice (n=3) were injected subcutaneously (s.c) with individual stabilized immune modulatory RNA-based oligonucleotides from Table 3 at 25 mg/kg (single dose). Serum was collected by retro-orbital bleeding 2 hr after immune modulatory oligonucleotide administration and cytokine and chemokine levels were determined by sandwich ELISA or Luminex multiplex assays. The results are shown in FIGS. 8A, 8B, 9A and 9B and demonstrate that in vivo administration of SIMRA oligonucleotides according to the invention generates unique cytokine and chemokine profiles. All reagents, including cytokine and chemokine antibodies and standards were purchased from PharMingen. (San Diego, Calif.).

Example 5

Serum Stability Assay

Approximately 0.5 OD of exemplar SIMRA compounds from Table 3 was individually incubated in 1% human serum in PBS for 30 minute at 37° C. Following 30 minutes of incubation in 1% human serum, the SIMRA compound was analyzed on anion-exchange HPLC to determine the percentage of full-length SIMRA compound that remained as compared to the amount of SIMRA compound present before serum treatment. The results are shown in FIGS. 10A-10H and demonstrate that chemical modifications according to the invention made to RNA-based compounds can enhance their stability.

EQUIVALENTS

While the foregoing invention has been described in some detail for purposes of clarity and understanding, it will be appreciated by one skilled in the art from a reading of this disclosure that various changes in form and detail can be made without departing from the true scope of the invention and appended claims.

---

What is claimed:

1. A SIMRA compound having the sequence:
    (a) 5'-UGC$_1$UGC$_1$C$_1$UUUG-m-GUUUC$_1$C$_1$GUC$_1$GU-5' (5'-SEQ ID NO: 43-3'-m-3'-SEQ ID NO: 43-5'); or
    (b) 5'-UG$_1$CUG$_1$CCUUUG$_1$-Y-X-Y-G$_1$UUUCCG$_1$UCG$_1$U-5'(5'-SEQ ID NO: 178-3'-Y-X-Y-3'-SEQ ID NO: 178-5');
    wherein G$_1$ is 7-deaza-rG, C$_1$ is ara-C, m is cis,trans-cyclohexanetriol, X is a glycerol linker, and Y is 1,3-propanediol.

2. A composition comprising the SIMRA compound of claim 1 and a physiologically acceptable carrier.

3. A method for generating a TLR7-mediated, TLR8-mediated, or TLR7/8-mediated immune response in a mammal, the method comprising administering to the mammal the SIMRA compound according to claim 1.

4. The composition according to claim 2, further comprising one or more chemotherapeutic compounds, a targeted therapeutic agent, an antibody, a DNA vaccine, a protein vaccine, a peptide vaccine, an antigen, or an adjuvant.

5. The composition according to claim 4, wherein the adjuvant is an alum-based adjuvant.

* * * * *

SEQUENCE LISTING

```
<160> NUMBER OF SEQ ID NOS: 192

<210> SEQ ID NO 1
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 1
uucugcuucu g                                                          11

<210> SEQ ID NO 2
<211> LENGTH: 11
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 2
ugcugccuuu g                                                              11

<210> SEQ ID NO 3
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 3
ugcugccuuu g                                                              11

<210> SEQ ID NO 4
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 7-deaza-rG
<220> FEATURE:
<221> NAME/KEY: modified_base
<222> LOCATION: (8)..(8)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 4
guccuuugcu g                                                              11

<210> SEQ ID NO 5
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 5
ugcugcuugu g                                                        11

<210> SEQ ID NO 6
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ugcugccuuu g                                                        11

<210> SEQ ID NO 7
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 7-deaza-rG
<220> FEATURE:
<221> NAME/KEY: modified_base
<222> LOCATION: (7)..(7)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 7
guccuugcuu g                                                        11

<210> SEQ ID NO 8
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 8
uucugcuucu g                                                        11

<210> SEQ ID NO 9
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 7-deaza-rG
<220> FEATURE:
<221> NAME/KEY: modified_base
<222> LOCATION: (8)..(8)
<223> OTHER INFORMATION: 7-deaza-rG
<220> FEATURE:
```

```
<221> NAME/KEY: modified_base
<222> LOCATION: (11)..(11)
<223> OTHER INFORMATION: 7-deaza-rG

<400> SEQUENCE: 9
guccuuugcu g                                                          11

<210> SEQ ID NO 10
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uugacguuga c                                                          11

<210> SEQ ID NO 11
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gugccugaug a                                                          11

<210> SEQ ID NO 12
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
augcugcgcu g                                                          11

<210> SEQ ID NO 13
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: Ara-G

<400> SEQUENCE: 13
ugcugcuugu g                                                          11

<210> SEQ ID NO 14
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Ara-G

<400> SEQUENCE: 14
ugcugcuugu g                                                          11
```

-continued

```
<210> SEQ ID NO 15
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Ara-G
<220> FEATURE:
<221> NAME/KEY: modified_base
<222> LOCATION: (5)..(5)
<223> OTHER INFORMATION: Ara-G
<220> FEATURE:
<221> NAME/KEY: modified_base
<222> LOCATION: (9)..(9)
<223> OTHER INFORMATION: Ara-G
<220> FEATURE:
<221> NAME/KEY: modified_base
<222> LOCATION: (11)..(11)
<223> OTHER INFORMATION: Ara-G

<400> SEQUENCE: 15
ugcugcuugu g                                                            11

<210> SEQ ID NO 16
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Ara-G
<220> FEATURE:
<221> NAME/KEY: modified_base
<222> LOCATION: (5)..(5)
<223> OTHER INFORMATION: Ara-G
<220> FEATURE:
<221> NAME/KEY: modified_base
<222> LOCATION: (9)..(9)
<223> OTHER INFORMATION: Ara-G
<220> FEATURE:
<221> NAME/KEY: modified_base
<222> LOCATION: (11)..(11)
<223> OTHER INFORMATION: Ara-G

<400> SEQUENCE: 16
ugcugcuugu g                                                            11

<210> SEQ ID NO 17
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Ara-G
<220> FEATURE:
<221> NAME/KEY: modified_base
<222> LOCATION: (5)..(5)
<223> OTHER INFORMATION: Ara-G
<220> FEATURE:
<221> NAME/KEY: modified_base
<222> LOCATION: (9)..(9)
<223> OTHER INFORMATION: Ara-G
<220> FEATURE:
```

```
<221> NAME/KEY: modified_base
<222> LOCATION: (11)..(11)
<223> OTHER INFORMATION: Ara-G

<400> SEQUENCE: 17
ugcugcuugu g                                                          11

<210> SEQ ID NO 18
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Ara-G
<220> FEATURE:
<221> NAME/KEY: modified_base
<222> LOCATION: (5)..(5)
<223> OTHER INFORMATION: Ara-G
<220> FEATURE:
<221> NAME/KEY: modified_base
<222> LOCATION: (11)..(11)
<223> OTHER INFORMATION: Ara-G

<400> SEQUENCE: 18
ugcugccuuu g                                                          11

<210> SEQ ID NO 19
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Ara-G
<220> FEATURE:
<221> NAME/KEY: modified_base
<222> LOCATION: (5)..(5)
<223> OTHER INFORMATION: Ara-G
<220> FEATURE:
<221> NAME/KEY: modified_base
<222> LOCATION: (11)..(11)
<223> OTHER INFORMATION: Ara-G

<400> SEQUENCE: 19
ugcugccuuu g                                                          11

<210> SEQ ID NO 20
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Ara-G
<220> FEATURE:
<221> NAME/KEY: modified_base
<222> LOCATION: (5)..(5)
<223> OTHER INFORMATION: Ara-G
<220> FEATURE:
<221> NAME/KEY: modified_base
<222> LOCATION: (11)..(11)
<223> OTHER INFORMATION: Ara-G

<400> SEQUENCE: 20
```
ugcugccuuu g                                                                     11

<210> SEQ ID NO 21
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: Ara-C
<220> FEATURE:
<221> NAME/KEY: modified_base
<222> LOCATION: (6)..(6)
<223> OTHER INFORMATION: Ara-C

<400> SEQUENCE: 21
ugcugcuugu g                                                                     11

<210> SEQ ID NO 22
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: Ara-C
<220> FEATURE:
<221> NAME/KEY: modified_base
<222> LOCATION: (6)..(6)
<223> OTHER INFORMATION: Ara-C

<400> SEQUENCE: 22
ugcugcuugu g                                                                     11

<210> SEQ ID NO 23
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: Ara-C
<220> FEATURE:
<221> NAME/KEY: modified_base
<222> LOCATION: (6)..(6)
<223> OTHER INFORMATION: Ara-C

<400> SEQUENCE: 23
ugcugcuugu g                                                                     11

<210> SEQ ID NO 24
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: Ara-C
<220> FEATURE:
<221> NAME/KEY: modified_base

```
<222> LOCATION: (6)..(6)
<223> OTHER INFORMATION: Ara-C
<220> FEATURE:
<221> NAME/KEY: modified_base
<222> LOCATION: (9)..(9)
<223> OTHER INFORMATION: Ara-C

<400> SEQUENCE: 24
ugcugcuucu g                                                              11

<210> SEQ ID NO 25
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: Ara-C
<220> FEATURE:
<221> NAME/KEY: modified_base
<222> LOCATION: (6)..(7)
<223> OTHER INFORMATION: Ara-C

<400> SEQUENCE: 25
ugcugccuuu g                                                              11

<210> SEQ ID NO 26
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: Ara-C
<220> FEATURE:
<221> NAME/KEY: modified_base
<222> LOCATION: (6)..(7)
<223> OTHER INFORMATION: Ara-C

<400> SEQUENCE: 26
ugcugccuuu g                                                              11

<210> SEQ ID NO 27
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: Ara-C
<220> FEATURE:
<221> NAME/KEY: modified_base
<222> LOCATION: (6)..(7)
<223> OTHER INFORMATION: Ara-C

<400> SEQUENCE: 27
ugcugccuuu g                                                              11

<210> SEQ ID NO 28
<211> LENGTH: 11
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: Ara-U
<220> FEATURE:
<221> NAME/KEY: modified_base
<222> LOCATION: (10)..(10)
<223> OTHER INFORMATION: Ara-U

<400> SEQUENCE: 28
ugcugcuucu g                                                            11

<210> SEQ ID NO 29
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: Ara-U
<220> FEATURE:
<221> NAME/KEY: modified_base
<222> LOCATION: (10)..(10)
<223> OTHER INFORMATION: Ara-U

<400> SEQUENCE: 29
ugcugcuucu g                                                            11

<210> SEQ ID NO 30
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: Ara-A

<400> SEQUENCE: 30
uguuguguga c                                                            11

<210> SEQ ID NO 31
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Ara-G
<220> FEATURE:
<221> NAME/KEY: modified_base
<222> LOCATION: (5)..(5)
<223> OTHER INFORMATION: Ara-G
<220> FEATURE:
<221> NAME/KEY: modified_base
<222> LOCATION: (9)..(9)
<223> OTHER INFORMATION: Ara-G
<220> FEATURE:
<221> NAME/KEY: modified_base
<222> LOCATION: (11)..(11)
<223> OTHER INFORMATION: Ara-G

<400> SEQUENCE: 31
```
ugcugcuugu g                                                                 11

<210> SEQ ID NO 32
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: Ara-C
<220> FEATURE:
<221> NAME/KEY: modified_base
<222> LOCATION: (6)..(6)
<223> OTHER INFORMATION: Ara-C

<400> SEQUENCE: 32
ugcugcuugu g                                                                 11

<210> SEQ ID NO 33
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: Ara-C
<220> FEATURE:
<221> NAME/KEY: modified_base
<222> LOCATION: (6)..(7)
<223> OTHER INFORMATION: Ara-C

<400> SEQUENCE: 33
ugcugccuuu g                                                                 11

<210> SEQ ID NO 34
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
gauugugacg u                                                                 11

<210> SEQ ID NO 35
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
cugaagcuug u                                                                 11

<210> SEQ ID NO 36
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (2)..(2)
<223> OTHER INFORMATION: Ara-G
<220> FEATURE:
<221> NAME/KEY: modified_base
<222> LOCATION: (5)..(5)
<223> OTHER INFORMATION: Ara-G
<220> FEATURE:
<221> NAME/KEY: modified_base
<222> LOCATION: (9)..(9)
<223> OTHER INFORMATION: Ara-G
<220> FEATURE:
<221> NAME/KEY: modified_base
<222> LOCATION: (11)..(11)
<223> OTHER INFORMATION: Ara-G

<400> SEQUENCE: 36
ugcugcuugu g                                                           11

<210> SEQ ID NO 37
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
ugcugcuugu g                                                           11

<210> SEQ ID NO 38
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 38
ugcugcuucu g                                                           11

<210> SEQ ID NO 39
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-ara-G
<220> FEATURE:
<221> NAME/KEY: modified_base
<222> LOCATION: (5)..(5)
<223> OTHER INFORMATION: 7-deaza-ara-G
<220> FEATURE:
<221> NAME/KEY: modified_base
<222> LOCATION: (11)..(11)
<223> OTHER INFORMATION: 7-deaza-ara-G

<400> SEQUENCE: 39
```
ugcugcuucu g                                                        11

<210> SEQ ID NO 40
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-ara-G
<220> FEATURE:
<221> NAME/KEY: modified_base
<222> LOCATION: (5)..(5)
<223> OTHER INFORMATION: 7-deaza-ara-G
<220> FEATURE:
<221> NAME/KEY: modified_base
<222> LOCATION: (11)..(11)
<223> OTHER INFORMATION: 7-deaza-ara-G

<400> SEQUENCE: 40
ugcugccuuu g                                                        11

<210> SEQ ID NO 41
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
ugacgaugag u                                                        11

<210> SEQ ID NO 42
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: Ara-U
<220> FEATURE:
<221> NAME/KEY: modified_base
<222> LOCATION: (10)..(10)
<223> OTHER INFORMATION: Ara-U

<400> SEQUENCE: 42
ugcugcuucu g                                                        11

<210> SEQ ID NO 43
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: Ara-C
<220> FEATURE:
<221> NAME/KEY: modified_base
<222> LOCATION: (6)..(7)
<223> OTHER INFORMATION: Ara-C

<400> SEQUENCE: 43
ugcugccuuu g                                                              11

<210> SEQ ID NO 44
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 44
ugcugcuucu g                                                              11

<210> SEQ ID NO 45
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
ugacgacgcu u                                                              11

<210> SEQ ID NO 46
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
ugacgacugc u                                                              11

<210> SEQ ID NO 47
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
ugacgacuug c                                                              11

<210> SEQ ID NO 48
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
ugcgcgaacu u                                                              11

```
<210> SEQ ID NO 49
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (4)..(4)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 49
aguguuuucu g                                                              11

<210> SEQ ID NO 50
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 50
ugcugcuuuu g                                                              11

<210> SEQ ID NO 51
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (9)..(9)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 51
uguuguuugu g                                                              11

<210> SEQ ID NO 52
```

```
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (8)..(8)
<223> OTHER INFORMATION: 7-deaza-rG

<400> SEQUENCE: 52
ugaugaagcu u                                                            11

<210> SEQ ID NO 53
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
ugcugcuuga a                                                            11

<210> SEQ ID NO 54
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
uugacugaug a                                                            11

<210> SEQ ID NO 55
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
ugcugcuuuu g                                                            11

<210> SEQ ID NO 56
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
uguuguuugu g                                                            11

<210> SEQ ID NO 57
<211> LENGTH: 11
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 57
uguucgaaca c                                                              11

<210> SEQ ID NO 58
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
uugacguuga c                                                              11

<210> SEQ ID NO 59
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
uugacguuga c                                                              11

<210> SEQ ID NO 60
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
uugacguuga c                                                              11

<210> SEQ ID NO 61
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
uugacguuga c                                                              11

<210> SEQ ID NO 62
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
gugccugaug a                                                              11

<210> SEQ ID NO 63
<211> LENGTH: 11
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 63
ccgaugccga c                                                          11

<210> SEQ ID NO 64
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
ccgaugcauc g                                                          11

<210> SEQ ID NO 65
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
gugccugaug a                                                          11

<210> SEQ ID NO 66
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
gugccugaug a                                                          11

<210> SEQ ID NO 67
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
gugccugaug a                                                          11

<210> SEQ ID NO 68
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
ccgaugccga c                                                          11

<210> SEQ ID NO 69
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 69
ccgaugccga c                                                        11

<210> SEQ ID NO 70
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
ccgaugccga c                                                        11

<210> SEQ ID NO 71
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
ccgaugcauc g                                                        11

<210> SEQ ID NO 72
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
ccgaugcauc g                                                        11

<210> SEQ ID NO 73
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
ccgaugcauc g                                                        11

<210> SEQ ID NO 74
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
agcacaacug u                                                        11

<210> SEQ ID NO 75
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
```

-continued aaaaaaaaaa a                                                             11

<210> SEQ ID NO 76
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
cacuguugag a                                                             11

<210> SEQ ID NO 77
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
aacuguugac c                                                             11

<210> SEQ ID NO 78
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
caacgaccug u                                                             11

<210> SEQ ID NO 79
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (8)..(8)
<223> OTHER INFORMATION: 7-deaza-rG
<220> FEATURE:
<221> NAME/KEY: modified_base
<222> LOCATION: (10)..(10)
<223> OTHER INFORMATION: 7-deaza-rG

<400> SEQUENCE: 79
cacuguugag a                                                             11

<210> SEQ ID NO 80
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base

```
<222> LOCATION: (8)..(8)
<223> OTHER INFORMATION: 7-deaza-rG

<400> SEQUENCE: 80
aacuguugac c                                                          11

<210> SEQ ID NO 81
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (10)..(10)
<223> OTHER INFORMATION: 7-deaza-rG

<400> SEQUENCE: 81
caacgaccug u                                                          11

<210> SEQ ID NO 82
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
augcugcgcu g                                                          11

<210> SEQ ID NO 83
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
augcugcgcu g                                                          11

<210> SEQ ID NO 84
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
augcugcgcu g                                                          11

<210> SEQ ID NO 85
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
aacuguugac c                                                          11
```

<210> SEQ ID NO 86
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
cacuguugag a                                                          11

<210> SEQ ID NO 87
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
gcacacuugu u                                                          11

<210> SEQ ID NO 88
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
uguuguguga c                                                          11

<210> SEQ ID NO 89
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
ccgaugcauc g                                                          11

<210> SEQ ID NO 90
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
aacgaaccga c                                                          11

<210> SEQ ID NO 91
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
caacgaccug u                                                          11

<210> SEQ ID NO 92

<211> LENGTH: 11
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 92
caacgaccug u                                                          11

<210> SEQ ID NO 93
<211> LENGTH: 11
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 93
cguugugaug a                                                          11

<210> SEQ ID NO 94
<211> LENGTH: 11
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 94
acgauuguga c                                                          11

<210> SEQ ID NO 95
<211> LENGTH: 11
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 95
acuuugacga u                                                          11

<210> SEQ ID NO 96
<211> LENGTH: 11
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 96
cgaugcgaug a                                                          11

<210> SEQ ID NO 97
<211> LENGTH: 11
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 97
acgucugacg a                                                          11

<210> SEQ ID NO 98
<211> LENGTH: 11
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 98
aacugcugga u                                                              11

<210> SEQ ID NO 99
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
uuggacucca g                                                              11

<210> SEQ ID NO 100
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
ucgacuucca g                                                              11

<210> SEQ ID NO 101
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
ccgacuugga c                                                              11

<210> SEQ ID NO 102
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
aagacugaac u                                                              11

<210> SEQ ID NO 103
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Ara-G
<220> FEATURE:
<221> NAME/KEY: modified_base
<222> LOCATION: (5)..(5)
<223> OTHER INFORMATION: Ara-G
<220> FEATURE:
<221> NAME/KEY: modified_base
<222> LOCATION: (11)..(11)

-continued

<223> OTHER INFORMATION: Ara-G

<400> SEQUENCE: 103
ugcugccuuu g                                                          11

<210> SEQ ID NO 104
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Ara-G
<220> FEATURE:
<221> NAME/KEY: modified_base
<222> LOCATION: (5)..(5)
<223> OTHER INFORMATION: Ara-G
<220> FEATURE:
<221> NAME/KEY: modified_base
<222> LOCATION: (11)..(11)
<223> OTHER INFORMATION: Ara-G

<400> SEQUENCE: 104
ugcugccuuu g                                                          11

<210> SEQ ID NO 105
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Ara-G
<220> FEATURE:
<221> NAME/KEY: modified_base
<222> LOCATION: (5)..(5)
<223> OTHER INFORMATION: Ara-G
<220> FEATURE:
<221> NAME/KEY: modified_base
<222> LOCATION: (11)..(11)
<223> OTHER INFORMATION: Ara-G

<400> SEQUENCE: 105
ugcugccuuu g                                                          11

<210> SEQ ID NO 106
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Ara-G
<220> FEATURE:
<221> NAME/KEY: modified_base
<222> LOCATION: (5)..(5)
<223> OTHER INFORMATION: Ara-G
<220> FEATURE:
<221> NAME/KEY: modified_base
<222> LOCATION: (11)..(11)
<223> OTHER INFORMATION: Ara-G

<400> SEQUENCE: 106
ugcugccuuu g                                                          11

```
<210> SEQ ID NO 107
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Ara-G
<220> FEATURE:
<221> NAME/KEY: modified_base
<222> LOCATION: (5)..(5)
<223> OTHER INFORMATION: Ara-G
<220> FEATURE:
<221> NAME/KEY: modified_base
<222> LOCATION: (11)..(11)
<223> OTHER INFORMATION: Ara-G

<400> SEQUENCE: 107
ugcugccuuu g                                                            11

<210> SEQ ID NO 108
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Ara-G
<220> FEATURE:
<221> NAME/KEY: modified_base
<222> LOCATION: (5)..(5)
<223> OTHER INFORMATION: Ara-G
<220> FEATURE:
<221> NAME/KEY: modified_base
<222> LOCATION: (11)..(11)
<223> OTHER INFORMATION: Ara-G

<400> SEQUENCE: 108
ugcugccuuu g                                                            11

<210> SEQ ID NO 109
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Ara-G
<220> FEATURE:
<221> NAME/KEY: modified_base
<222> LOCATION: (5)..(5)
<223> OTHER INFORMATION: Ara-G
<220> FEATURE:
<221> NAME/KEY: modified_base
<222> LOCATION: (11)..(11)
<223> OTHER INFORMATION: Ara-G

<400> SEQUENCE: 109
ugcugccuuu g                                                            11

<210> SEQ ID NO 110
<211> LENGTH: 11
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Ara-G
<220> FEATURE:
<221> NAME/KEY: modified_base
<222> LOCATION: (5)..(5)
<223> OTHER INFORMATION: Ara-G
<220> FEATURE:
<221> NAME/KEY: modified_base
<222> LOCATION: (11)..(11)
<223> OTHER INFORMATION: Ara-G

<400> SEQUENCE: 110
ugcugccuuu g                                                            11

<210> SEQ ID NO 111
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Ara-G
<220> FEATURE:
<221> NAME/KEY: modified_base
<222> LOCATION: (5)..(5)
<223> OTHER INFORMATION: Ara-G
<220> FEATURE:
<221> NAME/KEY: modified_base
<222> LOCATION: (11)..(11)
<223> OTHER INFORMATION: Ara-G

<400> SEQUENCE: 111
ugcugccuuu g                                                            11

<210> SEQ ID NO 112
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 7-deaza-rG
<220> FEATURE:
<221> NAME/KEY: modified_base
<222> LOCATION: (7)..(7)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 112
guccuugcuu g                                                            11

<210> SEQ ID NO 113
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 113
uucugcuucu g                                                           11

<210> SEQ ID NO 114
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 114
ugcugccuuu g                                                           11

<210> SEQ ID NO 115
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (8)..(8)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 115
ugccuuugcu g                                                           11

<210> SEQ ID NO 116
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base

```
<222> LOCATION: (11)..(11)
<223> OTHER INFORMATION: 7-deaza-rG

<400> SEQUENCE: 116
ugcugcuucu g                                                              11

<210> SEQ ID NO 117
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (3)..(3)
<223> OTHER INFORMATION: Ara-C
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (6)..(7)
<223> OTHER INFORMATION: Ara-C
<220> FEATURE:
<221> NAME/KEY: modified_base
<222> LOCATION: (11)..(11)
<223> OTHER INFORMATION: 7-deaza-rG

<400> SEQUENCE: 117
ugcugccuuu g                                                              11

<210> SEQ ID NO 118
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (3)..(3)
<223> OTHER INFORMATION: Ara-C
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (6)..(6)
<223> OTHER INFORMATION: Ara-C
<220> FEATURE:
<221> NAME/KEY: modified_base
<222> LOCATION: (9)..(9)
<223> OTHER INFORMATION: Ara-C
<220> FEATURE:
<221> NAME/KEY: modified_base
<222> LOCATION: (11)..(11)
<223> OTHER INFORMATION: 7-deaza-rG

<400> SEQUENCE: 118
ugcugcuucu g                                                              11

<210> SEQ ID NO 119
<211> LENGTH: 11
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
ugcugcuucu g                                                              11

<210> SEQ ID NO 120
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
uggcuugacg c                                                              11

<210> SEQ ID NO 121
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
ugcugcuuga a                                                              11

<210> SEQ ID NO 122
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
ugacgaugag u                                                              11

<210> SEQ ID NO 123
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
ugaugaggac u                                                              11

<210> SEQ ID NO 124
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
uguugaggaa c                                                              11

<210> SEQ ID NO 125
<211> LENGTH: 11
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 125
ugcgagacug c                                                              11

<210> SEQ ID NO 126
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
guugaacgac u                                                              11

<210> SEQ ID NO 127
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
ugacugauga c                                                              11

<210> SEQ ID NO 128
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
uguugaacga c                                                              11

<210> SEQ ID NO 129
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
ugagcgugaa c                                                              11

<210> SEQ ID NO 130
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: 7-deaza-rG
<220> FEATURE:
<221> NAME/KEY: modified_base
<222> LOCATION: (7)..(7)
<223> OTHER INFORMATION: 7-deaza-rG
<220> FEATURE:
<221> NAME/KEY: modified_base
<222> LOCATION: (10)..(10)
<223> OTHER INFORMATION: 7-deaza-rG
```

<400> SEQUENCE: 130
uggcuugacg c                                                                 11

<210> SEQ ID NO 131
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (8)..(8)
<223> OTHER INFORMATION: 7-deaza-rG
<220> FEATURE:
<221> NAME/KEY: modified_base
<222> LOCATION: (10)..(10)
<223> OTHER INFORMATION: 7-deaza-rG

<400> SEQUENCE: 131
ugacgaugag u                                                                 11

<210> SEQ ID NO 132
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (7)..(8)
<223> OTHER INFORMATION: 7-deaza-rG

<400> SEQUENCE: 132
uguugaggaa c                                                                 11

<210> SEQ ID NO 133
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (9)..(9)
<223> OTHER INFORMATION: 7-deaza-rG

```
<400> SEQUENCE: 133
uguugaacga c                                                          11

<210> SEQ ID NO 134
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
ugcgagacug c                                                          11

<210> SEQ ID NO 135
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
ugagcgugaa c                                                          11

<210> SEQ ID NO 136
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
uugagcugga c                                                          11

<210> SEQ ID NO 137
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
guugaggaac u                                                          11

<210> SEQ ID NO 138
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
ugaugaagcu u                                                          11

<210> SEQ ID NO 139
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
```
uugacgauga g								11

<210> SEQ ID NO 140
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
uuguugaacg a								11

<210> SEQ ID NO 141
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
uugaacgacu u								11

<210> SEQ ID NO 142
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
ugauggaacg a								11

<210> SEQ ID NO 143
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 143
ugcugccuuu g								11

<210> SEQ ID NO 144
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base

```
<222> LOCATION: (5)..(5)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 144
ugcugccuuu g                                                          11

<210> SEQ ID NO 145
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 145
ugcugccuuu g                                                          11

<210> SEQ ID NO 146
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 146
ugcugccuuu g                                                          11

<210> SEQ ID NO 147
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (11)..(11)
```

<223> OTHER INFORMATION: 7-deaza-rG

<400> SEQUENCE: 147
ugcugccuuu g                                                              11

<210> SEQ ID NO 148
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
ugcugcuugu g                                                              11

<210> SEQ ID NO 149
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
ugcugcuugu g                                                              11

<210> SEQ ID NO 150
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
ugcugcuugu g                                                              11

<210> SEQ ID NO 151
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
caacgaaccc u                                                              11

<210> SEQ ID NO 152
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
ugcugcugcu g                                                              11

<210> SEQ ID NO 153
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
ugaagcuuga a                                                             11

<210> SEQ ID NO 154
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
ugaacgugaa c                                                             11

<210> SEQ ID NO 155
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-methyl-C
<220> FEATURE:
<221> NAME/KEY: modified_base
<222> LOCATION: (6)..(6)
<223> OTHER INFORMATION: 5-methyl-C

<400> SEQUENCE: 155
ugcugcuugu g                                                             11

<210> SEQ ID NO 156
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (3)..(3)
<223> OTHER INFORMATION: 5-methyl-C
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (6)..(6)
<223> OTHER INFORMATION: 5-methyl-C
<220> FEATURE:
<221> NAME/KEY: modified_base
<222> LOCATION: (9)..(9)
<223> OTHER INFORMATION: 5-methyl-C
<220> FEATURE:
<221> NAME/KEY: modified_base
<222> LOCATION: (11)..(11)
<223> OTHER INFORMATION: 7-deaza-rG

<400> SEQUENCE: 156
ugcugcuucu g                                                             11

<210> SEQ ID NO 157
<211> LENGTH: 11
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (8)..(8)
<223> OTHER INFORMATION: 7-deaza-rG
<220> FEATURE:
<221> NAME/KEY: modified_base
<222> LOCATION: (10)..(10)
<223> OTHER INFORMATION: 7-deaza-rG

<400> SEQUENCE: 157
ugacgaugag u                                                              11

<210> SEQ ID NO 158
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 7-deaza-rG
<220> FEATURE:
<221> NAME/KEY: modified_base
<222> LOCATION: (7)..(7)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 158
guccuugcuu g                                                              11

<210> SEQ ID NO 159
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 159
uucugcuucu g                                                              11

<210> SEQ ID NO 160
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (2)..(2)
<223> OTHER INFORMATION: 7-deaza-rG
<220> FEATURE:
<221> NAME/KEY: modified_base
<222> LOCATION: (8)..(8)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 160
ugccuuugcu g                                                            11

<210> SEQ ID NO 161
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 161
ugcugcuucu g                                                            11

<210> SEQ ID NO 162
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 162
uucugcuucu g                                                            11

<210> SEQ ID NO 163
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (8)..(8)
<223> OTHER INFORMATION: 7-deaza-rG
<220> FEATURE:
<221> NAME/KEY: modified_base
<222> LOCATION: (11)..(11)
```

```
<223> OTHER INFORMATION: 7-deaza-rG

<400> SEQUENCE: 163
ugccuuugcu g                                                              11

<210> SEQ ID NO 164
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (9)..(9)
<223> OTHER INFORMATION: Ara-C
<220> FEATURE:
<221> NAME/KEY: modified_base
<222> LOCATION: (11)..(11)
<223> OTHER INFORMATION: 7-deaza-rG

<400> SEQUENCE: 164
ugcugcuucu g                                                              11

<210> SEQ ID NO 165
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (9)..(9)
<223> OTHER INFORMATION: Ara-C
<220> FEATURE:
<221> NAME/KEY: modified_base
<222> LOCATION: (11)..(11)
<223> OTHER INFORMATION: 7-deaza-rG

<400> SEQUENCE: 165
ugcugcuucu g                                                              11

<210> SEQ ID NO 166
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-F-C
<220> FEATURE:
<221> NAME/KEY: modified_base
<222> LOCATION: (7)..(7)
<223> OTHER INFORMATION: 2'-F-C
```

<400> SEQUENCE: 166
cugaagcuug u                                                                    11

<210> SEQ ID NO 167
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-F-U
<220> FEATURE:
<221> NAME/KEY: modified_base
<222> LOCATION: (8)..(9)
<223> OTHER INFORMATION: 2'-F-U
<220> FEATURE:
<221> NAME/KEY: modified_base
<222> LOCATION: (11)..(11)
<223> OTHER INFORMATION: 2'-F-U

<400> SEQUENCE: 167
cugaagcuug u                                                                    11

<210> SEQ ID NO 168
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Ara-G
<220> FEATURE:
<221> NAME/KEY: modified_base
<222> LOCATION: (8)..(8)
<223> OTHER INFORMATION: Ara-G

<400> SEQUENCE: 168
aacuguugac c                                                                    11

<210> SEQ ID NO 169
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: Ara-G
<220> FEATURE:
<221> NAME/KEY: modified_base
<222> LOCATION: (7)..(7)
<223> OTHER INFORMATION: Ara-G
<220> FEATURE:
<221> NAME/KEY: modified_base
<222> LOCATION: (10)..(10)
<223> OTHER INFORMATION: Ara-G

<400> SEQUENCE: 169
uggcuugacg c                                                                    11

<210> SEQ ID NO 170
<211> LENGTH: 11
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 170
ugacgcugac u                                                              11

<210> SEQ ID NO 171
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
ugacugcgac u                                                              11

<210> SEQ ID NO 172
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
ugcgaacgcu u                                                              11

<210> SEQ ID NO 173
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
ugcgacugac u                                                              11

<210> SEQ ID NO 174
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
ugcgcugaac u                                                              11

<210> SEQ ID NO 175
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
ugcugacgac u                                                              11

<210> SEQ ID NO 176
<211> LENGTH: 11
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 176
ugcuugaacg c                                                              11

<210> SEQ ID NO 177
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
uugcugaacg c                                                              11

<210> SEQ ID NO 178
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (11)..(11)
<223> OTHER INFORMATION: 7-deaza-rG

<400> SEQUENCE: 178
ugcugccuuu g                                                              11

<210> SEQ ID NO 179
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
uguuguguga c                                                              11

<210> SEQ ID NO 180
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
ugcugccuuu g                                                              11

<210> SEQ ID NO 181
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 181
ugcugcugcu g                                                          11

<210> SEQ ID NO 182
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
uguuguguga c                                                          11

<210> SEQ ID NO 183
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
uugaacgacu u                                                          11

<210> SEQ ID NO 184
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
uguuguguga c                                                          11

<210> SEQ ID NO 185
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
ugcugccuuu g                                                          11

<210> SEQ ID NO 186
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
ugcugcugcu g                                                          11

<210> SEQ ID NO 187
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
```

<223> OTHER INFORMATION: Ara-U

<400> SEQUENCE: 187
ugcugcuugu g                                                           11

<210> SEQ ID NO 188
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Ara-U
<220> FEATURE:
<221> NAME/KEY: modified_base
<222> LOCATION: (4)..(4)
<223> OTHER INFORMATION: Ara-U

<400> SEQUENCE: 188
ugcugcuugu g                                                           11

<210> SEQ ID NO 189
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Ara-U
<220> FEATURE:
<221> NAME/KEY: modified_base
<222> LOCATION: (4)..(4)
<223> OTHER INFORMATION: Ara-U
<220> FEATURE:
<221> NAME/KEY: modified_base
<222> LOCATION: (7)..(8)
<223> OTHER INFORMATION: Ara-U
<220> FEATURE:
<221> NAME/KEY: modified_base
<222> LOCATION: (10)..(10)
<223> OTHER INFORMATION: Ara-U

<400> SEQUENCE: 189
ugcugcuugu g                                                           11

<210> SEQ ID NO 190
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
uugacuguug a                                                           11

<210> SEQ ID NO 191
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191

-continued ucagucgcag u                                                    11

<210> SEQ ID NO 192
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 7-deaza-rG
<220> FEATURE:
<221> NAME/KEY: modified_base
<222> LOCATION: (5)..(5)
<223> OTHER INFORMATION: 7-deaza-rG
<220> FEATURE:
<221> NAME/KEY: modified_base
<222> LOCATION: (10)..(10)
<223> OTHER INFORMATION: 7-deaza-rG

<400> SEQUENCE: 192
ugcugccuug                                                      10